United States Patent
Lu et al.

(10) Patent No.: US 9,244,061 B2
(45) Date of Patent: Jan. 26, 2016

(54) METHODS AND COMPOSITIONS FOR DIAGNOSTIC ASSAYS FOR MEASURING CELL MEDIATED IMMUNE RESPONSE

(75) Inventors: Yichen Lu, Wellesley, MA (US); Neal Touzjian, Belmont, MA (US); Huishan Guo, Hainan (CN); Wenbiao Zheng, Fujian (CN)

(73) Assignee: Vaccine Technologies, Incorporated, Wellesley, MA (US)

( * ) Notice: Subject to any disclaimer, the term of this patent is extended or adjusted under 35 U.S.C. 154(b) by 0 days.

(21) Appl. No.: 13/377,752

(22) PCT Filed: Jun. 11, 2010

(86) PCT No.: PCT/US2010/038312
§ 371 (c)(1),
(2), (4) Date: Feb. 8, 2012

(87) PCT Pub. No.: WO2010/144799
PCT Pub. Date: Dec. 16, 2010

(65) Prior Publication Data
US 2012/0172254 A1    Jul. 5, 2012

Related U.S. Application Data

(60) Provisional application No. 61/186,437, filed on Jun. 12, 2009.

(51) Int. Cl.
*C40B 40/10* (2006.01)
*G01N 33/50* (2006.01)
(Continued)

(52) U.S. Cl.
CPC .......... *G01N 33/5091* (2013.01); *G01N 33/505* (2013.01); *G01N 33/5047* (2013.01); *G01N 33/56972* (2013.01); *G01N 33/6863* (2013.01); *C40B 40/10* (2013.01); *G01N 2800/24* (2013.01)

(58) Field of Classification Search
CPC ............ G01N 33/5047; G01N 33/505; G01N 33/56972; G01N 33/6863; G01N 33/5091; C12Q 1/025
See application file for complete search history.

(56) References Cited

U.S. PATENT DOCUMENTS 5,591,631 A    1/1997 Leppla et al.
5,674,698 A    10/1997 Zarling et al.
(Continued)

FOREIGN PATENT DOCUMENTS

WO    94/18332 A2    8/1994
WO    94/18332 A3    8/1994
(Continued)

OTHER PUBLICATIONS

Lightbody, K. et al 2008 Journal of Biological Chemistry 283: 17681-17690.*
(Continued)

*Primary Examiner* — Christian Boesen
(74) *Attorney, Agent, or Firm* — Nixon Peabody LLP

(57) ABSTRACT

Described are compositions and methods for detecting or monitoring the ability of an individual to mount a cell mediated immune response to a target antigen. Methods rely in part upon the physical association, e.g., by fusion, of a Lethal Factor (LF) polypeptide with a target antigen. The LF polypeptide moiety, including, for example, an LFn polypeptide moiety, serves as a transport factor to deliver target antigens, including full length target polypeptides, to the cytosol of an intact, living immune cell from an individual. Measurement of a cytokine response by the immune cell from the individual provides a read out of a cell mediated immune response. The methods and compositions described provide diagnostic as well as prognostic information and can guide the direction of therapy.

11 Claims, 17 Drawing Sheets

(51) Int. Cl.
   G01N 33/569    (2006.01)
   G01N 33/68     (2006.01)

(56)                References Cited

U.S. PATENT DOCUMENTS 5,677,274  A     10/1997  Leppla et al.
   6,592,872  B1     7/2003  Klimpel et al.
   2003/0190332 A1  10/2003  Gilad et al.
   2004/0057963 A1*  3/2004  Andersen et al. .......... 424/190.1
   2004/0166120 A1   8/2004  Thomas et al.
   2005/0220807 A1* 10/2005  Lu et al. .................... 424/190.1

FOREIGN PATENT DOCUMENTS

WO         97/23236  A3     7/1997
   WO        02/079417  A2    10/2002
   WO        02/079417  A3    10/2002
   WO      2008/048289  A2     4/2008
   WO      2008/048289  A3     4/2008

OTHER PUBLICATIONS

Combet C et al 2000 TIBS 25: 147-150. MULTALIN multiple alignment tool [online]. Alignment of SEQIDNO 3 of U.S. Appl. No. 13/377,752 and SEQIDNO 2 of U.S. PG-Pub 2005/0220807. Retrieved from the Internet: <http://npsa-pbil.ibcp.fr/cgi-bin/npsa_automat.pl?page=npsa_multalin.html>.*
Chen, Min et al., "Characteristics of Circulating T Cell Receptor γσ T Cells from Individuals Chronically Infected with Hepatitis B Virus (HBV): An Association Between Vσ2 Subtype and Chronic HBV Infection", The Journal of Infectious Diseases, vol. 198, No. 11, Dec. 1, 2008, pp. 1643-1650.
Della Bella, Silvia et al., "Decrease and Dysfunction of Dendritic Cells Correlate with Impaired Hepatitis C Virus-Specific CD4+ T-Cell Proliferation in Patients with Hepatitis C Virus Infection", Immunology, vol. 121, No. 2, Jun. 1, 2007, pp. 283-292.
Löhr, H. F. et al., "Reduced Virus Specific T Helper Cell Induction by Autologous Dendritic Cells in Patients with Chronic Hepatitis B—Restoration by Exogenous Interleukin-12", Clinical and Experimental Immunology, vol. 130, No. 1, Oct. 1, 2002, pp. 107-114.
Matsumura, S. et al., "High Frequency of Circulating HBcAg-Specific CD8 T Cells in Hepatitis B Infection: A Flow Cytometric Analysis". Clinical & Experimental Immunology, vol. 124, No. 3, Jun. 1, 2001, pp. 435-444.
Cao, H., et al., "Delivery of exogenous protein antigens to major histocompatibility complex class I pathway in cytosol," Journal of Infectious Diseases, University of Chicago Press, Chicago, IL, vol. 185, No. 2, Jan. 15, 2002 pp. 244-251.
Kushner, N. et al., "A fragment of anthrax lethal factor delivers proteins to the cytosol without requiring protective antigen," Proceedings of the National Academy of Sciences of the United States (PNAS), vol. 100, No. 11, May 27, 2003, pp. 6652-6657.
Shu, L. et al., "Recombinant hepatitus B large surface antigen, successfully produced in Escherichia coli, stimulates T-cell response in mice," Vaccine, vol. 24, No. 20, May 15, 2006, pp. 4409-4416.
Anderson, K. S. et al., "Intracellular Transport of class I MHC Molecules in Antigen Processing Mutant Cell Lines" Journal of Immunology. 151:3407-3419 (1993).
Androlewicz, M. J. et al., "Evidence that transporters associated with antigen processing translocate a major histocompatibility complex class I-binding peptide into the endoplasmic reticulum in an ATP-dependent manner" Proc. Natl. Acad. Sci. USA, 90:9130-9134 (1993).
Ballard, J. D., et al., "Anthrax Toxin-Mediated Delivery In Vivo and In Vitro of a Cytotoxic T-Lymphocyte Epitope from Ovalbumin" Infection and Immunity. 66:615-619 (1998).
Borrow, P. et al., "Virus-Specific CD8+ Cytotoxic T-Lymphocyte Activity Associated with Control of Viremia in Primary Human Immunodeficiency Virus Type 1 Infection" J. Virol. 68, No. 9:6103-6110 (1994).

Borrow, P. et al., "Antiviral pressure exerted by HIV-1-specific cytotoxic T lymphocytes (CTLs) during primary infection demonstrated by rapid selection of CTL escape virus" Nature Medicine. 3:205-211 (1997).
Brodie et al., "In vivo migration and function of transferred HIV-1-specific cytotoxic T cells" Nat. Med. 5:34-41 (1999).
Cao, H. et al., "Cytotoxic T-Lymphocyte Cross-Reactivity among Different Human Immunodeficiency Virus Type 1 Clades: Implications for Vaccine Development" J. Virol. 71:8615-8623 (1997).
Cao, H. et al., "Cellular Immunity to Human Immunodeficiency Virus Type 1 (HIV-1) Clades: Relevance to HIV-1 Vaccine Trials in Uganda" J. Infec Dis. 182:1350-1356 (2000).
Cao, H. et al., "Delivery of Exogenous Protein Antigens to Major Histocompatibility Complex Class I Pathway in cytosol" J. Infect. Dis. 185: 244-251 (2002).
Doling, A. et al., "Cytotoxic T-Lymphocyte Epitopes Fused to Anthrax Toxin Induce Protective Antiviral Immunity" Infection & Immunity. 67:3290-3296 (1999).
Falk, K. et al., "Identification of Naturally Processed Viral Nonapeptides Allows their Quantification in Infected Cells and Suggests an Allele-specific T Cell Epitope Forecast" J. Exp. Med. 174:425-434 (1991).
Finbloom, D. S. et al. "Endocytosis of particulate and soluble IgG immune complexes: differential effects of cytoskeletal modulating agents" Clinical & Experimental Immunology. 67:205-210 (1987).
Geisow, M. J. et al., "Temporal Changes of Lysosome and Phagosome pH during Phagolysosome Formation in Macrophages: Studies by Fluorescence Spectroscopy" Journal of Cell Biology. 89:645-652 (1981).
Goldberg, A. L. et al., "Proteolysis, proteasomes and antigen presentation" Nature. 357:375-379 (1992).
Hanna, P. C. et al., "On the role of macrophages in anthrax" Proc. Natl. Acad. Sci. USA. 90:10198-10201 (1993).
Letvin, "Progress in the Development of an HIV-1 Vaccine" Science 280:1875-1880 (1998).
Ogg, C. S. et al., "Quantitation of HIV-1-Specific Cytotoxic T Lymphocytes and Plasma Load of Viral RNA" Science 279:2103-2106 (1998).
Schmitz, J. et al., "Control of Viremia in Simian Immunodeficiency Virus Infection by CD8+ Lymphocytes" Science 283:857-860 (1999).
Arora, N. "Site directed mutagenesis of histidine residues in anthrax toxin lethal factor binding domain reduces toxicity" Molecular and Cellular Biochemistry; 177(1-2):7-14 (1997).
Barth, H. et al. "The N-Terminal Part of the enzyme Component (C2I) of the Binary Clostridium botulinum C2 Toxin Interacts with the Binding Component C2II and Functions as a Carrier System for a Rho ADP-Ribosylating C3-Like Fusion Toxin" Infection and Immunity; 66(4):1364-1369 (1998).
Falnes, P. O. et al. "Penetration of protein toxins into cells" Current Opinion in Cell Biology; 12(4):407-413 (2000).
Guidi-Rontani, C. et al. "Translocation of Bacillus anthracis lethal and oedema factors across endosome membranes" Cellular Microbiology; 2(3):259-264 (2000).
Gupta, P. et al. "Involvement of Residues 147VYYEIGK153 in Binding of Lethal Factor to Protective Antigen of Bacillus anthracis" Biochemical and Biophysical Research Communications; 280:158-163 (2001).
Kushner, N. et al. "A fragment of anthrax lethal factor delivers proteins to the cytosol without requiring protective antigen" PNAS; 100(11):6652-6657 (2003).
Stenmark, H. et al. "Peptides Fused to the amino-Terminal End of Diphtheria Toxin Are Translocated to the Cytosol" The Journal of Cell Biology; 113(5):1025-1032 (1991).
Goletz, T. et al., "Targeting HIV proteins to the major histocompatibility complex class I processing pathway with a novel gp120-anthrax toxin fusion protein" Proceedings of the National Academy of Sciences, USA, 94: 12059-12064 (1997).
Bowie et al., "Deciphering the Message in Protein Sequences: Tolerance to Amino Acid Substitutions" Science, 247: 1306-1310 (1990).
Bragg, T. et al., "Nucleotide sequence and analysis of the lethal factor gene (lef) from Bacillus anthracis," Gene, 81: 45-54 (1989).

(56) References Cited

OTHER PUBLICATIONS

Fayolle, C. et al., "In vivo induction of CTL responses by recombinant adenylate cyclase of Bordetella pertussis carrying viral CD8+ T cell epitopes," Journal of Immunology, 156:4697-4706 (1996).
Robertson, D. L., et al., "Molecular Cloning and expression in *Escherichia coli* of the lethal factor gene of *Bacillus anthracis*," Gene, 44:71-78 (1986).
Robinson, E. et al., "Lymphocyte Stimulation by Phytohemagglutinin and Tumor Cells of Malignant Effusions" Cancer Research, 34:1548-1551 (1974).
Arora, N. et al., "Residues 1-254 of Anthrax Toxin Lethal Factor Are Sufficient to Cause Cellular Uptake of Fused Polypeptides" The Journal of Biological Chemistry, 268(5):3334-3341 (1993).
Arora, N. et al., "Cytotoxic Effects of a Chimeric Protein Consisting of Tetanus Toxin Light Chain and Anthrax Toxin Lethal Factor in Non-neuronal Cells" The Journal of Biological Chemistry, 269(42);26165-26171 (1994).
Figueiredo, D. et al., "Characterization of Recombinant Tetanus Toxin Derivatives Suitable for Vaccine Development" Infection and Immunity, 63(8):3218-3221, (1995).
Leppla, S. H. et al., "Anthrax toxin fusion proteins for intracellular delivery of macromolecules" Journal of Applied Microbiology, 87:284 (1999).
Tang, G. et al., "Proteasome Activity Is Required for anthrax Lethal Toxin to Kill Macrophages" Infection and Immunity, 67(6):3055-3060 (1999).
Lu, Y. et al., "Genetically modified anthrax lethal toxin safely delivers whole HIV protein antigens into the cytosol to induce T cell immunity" PNAS, 97(14):8027-8032 (2000).
Ballard, J. D. et al., "Anthrax toxin-mediated delivery of a cytotoxic T-cell epitope in vivo" Pro. Natl. Acad. Sci. USA 93:12531-12534 (1996).
Lacy, D. B. et al., "Mapping the Anthrax Protective Antigenn Binding Site on the Lethal and Edema Factors" The Journal of Biological Chemistry, 277(4):3006-3010 (2002).
Milne, J. C. et al., "Protective antigen-binding domain of anthrax lethal factor mediates translocation of a heterologous protein fused to its amino- or carboxy-terminus" Molecular Microbiology 15(4):661-666 (1995).

\* cited by examiner

| SAMPLE ID | SEX | AGE | X-RAY | SPUTUM SMEAR | BCG | HISTORY | TB ANTIBODY | QFT (IU/ml) | RESULT AT (IU/ml) | WESTERN |
|---|---|---|---|---|---|---|---|---|---|---|
| T06-02-2 | M | 60 | TYPE III:RIGHT LUNG:SHADOW SEEN ON TOP/LEFT LUNG: SHADOW SEEN ON MIDDLE | N | N | BLOOD IN SPUTUM FOR 3 DAYS | P | P (0.35) | N (0.30) | N |
| T06-04-3 | M | 50 | TYPE III:RIGHT LUNG: SHADOW SEEN ON TOP-MIDDLE-BOTTOM/ LEFT LUNG:SHADOW SEEN ON TOP-MIDDLE-BOTTOM | 4+ | N | COUGH FOR MORE THAN 1 YEAR | N/A | P (0.53) | N (0.22) | N |
| T06-06-2 | M | 60 | OLD TB | N | N | TB WAS DISCOVERED FOR 1 DAY AFTER PHYSICAL EXAMINATION | P | N (-0.01) | P (0.70) | N |
| T06-13-3 | F | 52 | TYPE III: RIGHT LUNG: SHADOW SEEN ON TOP-MIDDLE-BOTTOM, A HOLE SEEN ON TOP/LEFT LUNG: SHADOW SEEN ON TOP-MIDDLE-BOTTOM, A HOLE SEEN ON TOP | 1+ | N | COUGH FOR 8 MONTHS | N/A | P (2.64) | N (0.30) | TBD |
| T06-13-4 | M | 46 | TYPE III: RIGHT LUNG:SHADOW SEEN ON TOP/LEFT: SHADOW SEEN ON TOP-MIDDLE | N | Y | COUGH FOR 1 MONTH, BLOOD IN SPUTUM ONCE | N/A | P (0.84) | N (0.20) | N |
| T06-16-2 | M | 15 | TYPE III: RIGHT LUNG: SHADOW SEEN ON TOP/LEFT: NEGATIVE | N | Y | N/A | N/A | N (0.00) | P (3.09) | N |
| T06-19-1 | M | 29 | TYPE III: RIGHT LUNG: SHADOW SEEN ON TOP-MIDDLE, A HOLE SEEN ON TOP/LEFT LUNG: NEGATIVE | N | Y | COUGH AND SPUTUM FOR 2+ MONTHS | N/A | P (5.48) | N (0.20) | TBD |
| T06-20-2 | M | 35 | TYPE III: RIGHT LUNG: SHADOW SEEN ON TOP/LEFT: NEGATIVE | N | Y | COUGH FOR 3 WEEKS | N/A | P (3.17) | N (0.29) | P |

FIG. 4

| | | QuantiFERON TB GOLD | | TOTAL |
|---|---|---|---|---|
| | | P | N | |
| ASACIR TB | P | 11 | 20 | 31 |
| | N | 0 | 9 | 9 |
| | TOTAL | 11 | 29 | 40 |

| SAMPLE ID | SEX | AGE | OCCUPATION | X-RAY | RESULT | | |
|---|---|---|---|---|---|---|---|
| | | | | | QFT (IU/ml) | AT (IU/ml) | WESTERN |
| T06-05-5 | M | 26 | N/A | N | N (0.00) | P (1.69) | P |
| T06-05-8 | F | 50 | N/A | N | N (0.00) | P (0.57) | ? |
| T06-10-8 | M | 27 | ENGINEER | N | N (-0.14) | P (0.73) | P |
| T06-05-10 | F | 41 | MANAGEMENT | N | N (-0.01) | P (0.51) | P |
| T06-13-6 | M | 24 | ENGINEER | N | N (0.00) | P (1.24) | P |
| T06-12-6 | M | 20 | SOLIDER | N | N (0.01) | P (2.23) | N |
| T06-12-8 | M | 28 | CAPTAIN | N | N (-0.01) | P (1.76) | P |
| T06-12-11 | M | 27 | CAPTAIN | N | N (0.00) | P (0.46) | ? |
| T06-12-12 | M | 20 | SOLIDER | N | N (0.04) | P (4.49) | N |
| T06-12-13 | M | 19 | SOLIDER | N | N (0.01) | P (0.85) | ? |
| T06-12-14 | M | 25 | CAPTION | N | N (-0.02) | P (1.17) | N |
| T06-03-7 | N/A | N/A | N/A | N/A | N (0.17) | P (9.11) | ? |
| T06-03-10 | M | 40 | ENGINEER | N | N (-0.02) | P (3.99) | P |
| T06-04-6 | F | 34 | CLEANER | N/A | N (0.01) | P (0.74) | P |
| T06-04-7 | M | 30 | ENGINEER | N | N (-0.01) | P (0.52) | P |
| T06-04-8 | F | 45 | ENGINEER | N | N (0.03) | P (1.50) | P |
| T06-04-9 | M | 30 | ENGINEER | N | N (0.01) | P (0.47) | P |
| T06-04-10 | M | 28 | ENGINEER | N | N (0.03) | P (2.81) | P |
| T06-16-6 | M | 28 | HOSPITAL STAFF | N | N (-0.01) | P (4.08) | P |
| T06-16-7 | M | 38 | HOSPITAL STAFF | N | N (0.06) | P (2.12) | ? |

| ASACIR | | TB GOLD | | |
|---|---|---|---|---|
| | | P | N | TOTAL |
| | P | 51 | 2 | 53 |
| | N | 0 | 7 | 7 |
| | TOTAL | 51 | 9 | 60 |

FIG. 12A

| VTI KIT | TB CULTURE | |
|---|---|---|
| | + | - |
| + | 7 | 13 |
| - | 0 | 1 |

FIG. 12B

| VTI KIT | TB SMEAR | |
|---|---|---|
| | + | - |
| + | 20 | 0 |
| - | 1 | 0 |

FIG. 12C

| TB SMEAR | TB CULTURE | |
|---|---|---|
| | + | - |
| + | 7 | 14 |
| - | 0 | 0 |

SEQUENCE LISTING

<160> NUMBER OF SEQ ID NOS: 47

<210> SEQ ID NO 1
<211> LENGTH: 809
<212> TYPE: PRT
<213> ORGANISM: Bacillus anthracis

<400> SEQUENCE: 1

```
Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205
```

```
Thr Ile Lys Asn Ala Ser Asp Ser Asp Gly Gln Asp Leu Leu Phe Thr
    210                 215                 220
Asn Gln Leu Lys Glu His Pro Thr Asp Phe Ser Val Glu Phe Leu Glu
225                 230                 235                 240
Gln Asn Ser Asn Glu Val Gln Glu Val Phe Ala Lys Ala Phe Ala Tyr
                245                 250                 255
Tyr Ile Glu Pro Gln His Arg Asp Val Leu Gln Leu Tyr Ala Pro Glu
                260                 265                 270
Ala Phe Asn Tyr Met Asp Lys Phe Asn Glu Gln Glu Ile Asn Leu Ser
            275                 280                 285
Leu Glu Glu Leu Lys Asp Gln Arg Met Leu Ser Arg Tyr Glu Lys Trp
290                 295                 300
Glu Lys Ile Lys Gln His Tyr Gln His Trp Ser Asp Ser Leu Ser Glu
305                 310                 315                 320
Glu Gly Arg Gly Leu Leu Lys Lys Leu Gln Ile Pro Ile Glu Pro Lys
                325                 330                 335
Lys Asp Asp Ile Ile His Ser Leu Ser Gln Glu Glu Lys Glu Leu Leu
                340                 345                 350
Lys Arg Ile Gln Ile Asp Ser Ser Asp Phe Leu Ser Thr Glu Glu Lys
            355                 360                 365
Glu Phe Leu Lys Lys Leu Gln Ile Asp Ile Arg Asp Ser Leu Ser Glu
370                 375                 380
Glu Glu Lys Glu Leu Leu Asn Arg Ile Gln Val Asp Ser Ser Asn Pro
385                 390                 395                 400
Leu Ser Glu Lys Glu Lys Glu Phe Leu Lys Lys Leu Lys Leu Asp Ile
                405                 410                 415
Gln Pro Tyr Asp Ile Asn Gln Arg Leu Gln Asp Thr Gly Gly Leu Ile
                420                 425                 430
Asp Ser Pro Ser Ile Asn Leu Asp Val Arg Lys Gln Tyr Lys Arg Asp
            435                 440                 445
Ile Gln Asn Ile Asp Ala Leu Leu His Gln Ser Ile Gly Ser Thr Leu
            450                 455                 460
Tyr Asn Lys Ile Tyr Leu Tyr Glu Asn Met Asn Ile Asn Asn Leu Thr
465                 470                 475                 480
Ala Thr Leu Gly Ala Asp Leu Val Asp Ser Thr Asp Asn Thr Lys Ile
                485                 490                 495
Asn Arg Gly Ile Phe Asn Glu Phe Lys Lys Asn Phe Lys Tyr Ser Ile
                500                 505                 510
Ser Ser Asn Tyr Met Ile Val Asp Ile Asn Glu Arg Pro Ala Leu Asp
            515                 520                 525
Asn Glu Arg Leu Lys Trp Arg Ile Gln Leu Ser Pro Asp Thr Arg Ala
530                 535                 540
Gly Tyr Leu Glu Asn Gly Lys Leu Ile Leu Gln Arg Asn Ile Gly Leu
545                 550                 555                 560
Glu Ile Lys Asp Val Gln Ile Ile Lys Gln Ser Glu Lys Glu Tyr Ile
                565                 570                 575
Arg Ile Asp Ala Lys Val Val Pro Lys Ser Lys Ile Asp Thr Lys Ile
                580                 585                 590
Gln Glu Ala Gln Leu Asn Ile Asn Gln Glu Trp Asn Lys Ala Leu Gly
            595                 600                 605
Leu Pro Lys Tyr Thr Lys Leu Ile Thr Phe Asn Val His Asn Arg Tyr
610                 615                 620
```

```
Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
            645                 650                 655

Asp Gly Asn Gly Arg Phe Val Phe Thr Asp Ile Thr Leu Pro Asn Ile
        660                 665                 670

Ala Glu Gln Tyr Thr His Gln Asp Glu Ile Tyr Gln Val His Ser
    675                 680                 685

Lys Gly Leu Tyr Val Pro Glu Ser Arg Ser Ile Leu Leu His Gly Pro
690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
            725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
            755                 760                 765

Phe Phe Ala Glu Ala Phe Arg Leu Met His Ser Thr Asp His Ala Glu
770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
            805

<210> SEQ ID NO 2
<211> LENGTH: 776
<212> TYPE: PRT
<213> ORGANISM: Bacillus anthracis

<400> SEQUENCE: 2

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190
```

```
Gln Leu Lys Glu His Pro Thr Asp Phe Ser Val Glu Phe Leu Glu Gln
            195                 200                 205

Asn Ser Asn Glu Val Gln Glu Val Phe Ala Lys Ala Phe Ala Tyr Tyr
        210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
            260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
    290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
            340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
    370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415

Gln Asn Ile Asp Ala Leu Leu His Gln Ser Ile Gly Ser Thr Leu Tyr
            420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
    450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
            500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
    530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575

Pro Lys Tyr Thr Lys Leu Ile Thr Phe Asn Val His Asn Arg Tyr Ala
            580                 585                 590

Ser Asn Ile Val Glu Ser Ala Tyr Leu Ile Leu Asn Glu Trp Lys Asn
        595                 600                 605
```

```
Asn Ile Gln Ser Asp Leu Ile Lys Lys Val Thr Asn Tyr Leu Val Asp
    610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
                645                 650                 655

Gly Leu Tyr Val Pro Glu Ser Arg Ser Ile Leu Leu His Gly Pro Ser
                660                 665                 670

Lys Gly Val Glu Leu Arg Asn Asp Ser Glu Gly Phe Ile His Glu Phe
                675                 680                 685

Gly His Ala Val Asp Asp Tyr Ala Gly Tyr Leu Leu Asp Lys Asn Gln
690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
                725                 730                 735

Phe Ala Glu Ala Phe Arg Leu Met His Ser Thr Asp His Ala Glu Arg
                740                 745                 750

Leu Lys Val Gln Lys Asn Ala Pro Lys Thr Phe Gln Phe Ile Asn Asp
                755                 760                 765

Gln Ile Lys Phe Ile Ile Asn Ser
770                 775

<210> SEQ ID NO 3
<211> LENGTH: 288
<212> TYPE: PRT
<213> ORGANISM: Bacillus anthracis

<400> SEQUENCE: 3

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
                20                  25                  30

Gly Ala Gly Gly His Gly Asp Val Gly Met His Val Lys Glu Lys Glu
                35                  40                  45

Lys Asn Lys Asp Glu Asn Lys Arg Lys Asp Glu Glu Arg Asn Lys Thr
50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
                100                 105                 110

Lys Ile Tyr Ile Val Asp Gly Asp Ile Thr Lys His Ile Ser Leu Glu
                115                 120                 125

Ala Leu Ser Glu Asp Lys Lys Lys Ile Lys Asp Ile Tyr Gly Lys Asp
130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
                180                 185                 190

Leu Ser Lys Ile Asn Gln Pro Tyr Gln Lys Phe Leu Asp Val Leu Asn
                195                 200                 205
```

Thr Ile Lys Asn Ala Ser Asp Ser Asp Gly Gln Asp Leu Leu Phe Thr
                210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
                260                 265                 270

Ala Phe Asn Tyr Met Asp Lys Phe Asn Glu Gln Glu Ile Asn Leu Ser
                275                 280                 285

<210> SEQ ID NO 4
<211> LENGTH: 255
<212> TYPE: PRT
<213> ORGANISM: Bacillus anthracis

<400> SEQUENCE: 4

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
                20                  25                  30

Glu Glu His Leu Lys Glu Ile Met Lys His Ile Val Lys Ile Glu Val
                35                  40                  45

Lys Gly Glu Glu Ala Val Lys Lys Glu Ala Ala Glu Lys Leu Leu Glu
50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
                100                 105                 110

Leu Leu His Glu His Tyr Val Tyr Ala Lys Glu Gly Tyr Glu Pro Val
                115                 120                 125

Leu Val Ile Gln Ser Ser Glu Asp Tyr Val Glu Asn Thr Glu Lys Ala
                130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
                180                 185                 190

Gln Leu Lys Glu His Pro Thr Asp Phe Ser Val Glu Phe Leu Glu Gln
                195                 200                 205

Asn Ser Asn Glu Val Gln Glu Val Phe Ala Lys Ala Phe Ala Tyr Tyr
210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser
                245                 250                 255

<210> SEQ ID NO 5
<211> LENGTH: 104
<212> TYPE: PRT
<213> ORGANISM: Bacillus anthracis

<400> SEQUENCE: 5

```
Gly Lys Ile Leu Ser Arg Asp Ile Leu Ser Lys Ile Asn Gln Pro Tyr
1               5                   10                  15

Gln Lys Phe Leu Asp Val Leu Asn Thr Ile Lys Asn Ala Ser Asp Ser
            20                  25                  30

Asp Gly Gln Asp Leu Leu Phe Thr Asn Gln Leu Lys Glu His Pro Thr
        35                  40                  45

Asp Phe Ser Val Glu Phe Leu Glu Gln Asn Ser Asn Glu Val Gln Glu
50                  55                  60

Val Phe Ala Lys Ala Phe Ala Tyr Tyr Ile Glu Pro Gln His Arg Asp
65                  70                  75                  80

Val Leu Gln Leu Tyr Ala Pro Glu Ala Phe Asn Tyr Met Asp Lys Phe
                85                  90                  95

Asn Glu Gln Glu Ile Asn Leu Ser
            100

<210> SEQ ID NO 6
<211> LENGTH: 95
<212> TYPE: PRT
<213> ORGANISM: Mycobacterium tuberculosis

<400> SEQUENCE: 6

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 7
<211> LENGTH: 100
<212> TYPE: PRT
<213> ORGANISM: Mycobacterium tuberculosis

<400> SEQUENCE: 7

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Ala Leu Ser Ser
                85                  90                  95

Gln Met Gly Phe
            100

<210> SEQ ID NO 8
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Pro Met Thr Glu Gln Gln Trp Asn Phe Ala Gly Ile Glu Ala
1               5                   10                  15

<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Glu Gln Gln Trp Asn Phe Ala Gly Ile Glu Ala Ala Ala Ser Ala
1               5                   10                  15

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Phe Ala Gly Ile Glu Ala Ala Ala Ser Ala Ile Gln Gly Asn
1               5                   10                  15

<210> SEQ ID NO 11
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Glu Ala Ala Ala Ser Ala Ile Gln Gly Asn Val Thr Ser Ile
1               5                   10                  15

<210> SEQ ID NO 12
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Ser Ala Ile Gln Gly Asn Val Thr Ser Ile His Ser Leu Leu
1               5                   10                  15

<210> SEQ ID NO 13
<211> LENGTH: 16
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 13

Ile Gln Gly Asn Val Thr Ser Ile His Ser Leu Leu Asp Glu Gly Lys
1               5                   10                  15

<210> SEQ ID NO 14
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Thr Ser Ile His Ser Leu Leu Asp Glu Gly Lys Gln Ser Leu Thr
1               5                   10                  15

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Leu Leu Asp Glu Gly Lys Gln Ser Leu Thr Lys Leu Ala Ala
1               5                   10                  15

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Gly Lys Gln Ser Leu Thr Lys Leu Ala Ala Ala Trp Gly Gly
1               5                   10                  15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Leu Thr Lys Leu Ala Ala Ala Trp Gly Gly Ser Gly Ser Glu
1               5                   10                  15

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 18

Leu Ala Ala Ala Trp Gly Gly Ser Gly Ser Glu Ala Tyr Gln Gly
1               5                   10                  15

<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Trp Gly Gly Ser Gly Ser Glu Ala Tyr Gln Gly Val Gln Gln Lys
1               5                   10                  15

<210> SEQ ID NO 20
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Ser Glu Ala Tyr Gln Gly Val Gln Gln Lys Trp Asp Ala Thr
1               5                   10                  15

<210> SEQ ID NO 21
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Tyr Gln Gly Val Gln Gln Lys Trp Asp Ala Thr Ala Thr Glu Leu
1               5                   10                  15

<210> SEQ ID NO 22
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Val Gln Gln Lys Trp Asp Ala Thr Ala Thr Glu Leu Asn Asn Ala Leu
1               5                   10                  15

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Ala Thr Ala Thr Glu Leu Asn Asn Ala Leu Gln Asn Leu Ala
1               5                   10                  15
```

```
<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Thr Glu Leu Asn Asn Ala Leu Gln Asn Leu Ala Arg Thr Ile Ser
1               5                   10                  15

<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asn Ala Leu Gln Asn Leu Ala Arg Thr Ile Ser Glu Ala Gly Gln
1               5                   10                  15

<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Leu Ala Arg Thr Ile Ser Glu Ala Gly Gln Ala Met Ala Ser
1               5                   10                  15

<210> SEQ ID NO 27
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Thr Ile Ser Glu Ala Gly Gln Ala Met Ala Ser Thr Glu Gly Asn
1               5                   10                  15

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Gly Gln Ala Met Ala Ser Thr Glu Gly Asn Val Thr Gly Met
1               5                   10                  15

<210> SEQ ID NO 29
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Met Ala Ser Thr Glu Gly Asn Val Thr Gly Met Phe Ala Leu Glu
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Arg Pro Leu Lys Asn Asp Ala Ala Thr Leu Ala Gln Glu Ala Gly
1               5                   10                  15

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asn Asp Ala Ala Thr Leu Ala Gln Glu Ala Gly Asn Phe Glu Arg
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Thr Leu Ala Gln Glu Ala Gly Asn Phe Glu Arg Ile Ser Gly Asp
1               5                   10                  15

<210> SEQ ID NO 33
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Glu Ala Gly Asn Phe Glu Arg Ile Ser Gly Asp Leu Lys Thr Gln
1               5                   10                  15

<210> SEQ ID NO 34
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 34

Phe Glu Arg Ile Ser Gly Asp Leu Lys Thr Gln Ile Asp Gln Val
1               5                   10                  15

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Gly Asp Leu Lys Thr Gln Ile Asp Gln Val Glu Ser Thr Ala
1               5                   10                  15

<210> SEQ ID NO 36
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Lys Thr Gln Ile Asp Gln Val Glu Ser Thr Ala Gly Ser Leu Gln
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asp Gln Val Glu Ser Thr Ala Gly Ser Leu Gln Ala Gln Trp Arg
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ser Thr Ala Gly Ser Leu Gln Ala Gln Trp Arg Gly Ala Ala Gly
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39
```

```
Ser Leu Gln Ala Gln Trp Arg Gly Ala Ala Gly Thr Ala Ala Gln
1               5                   10                  15
```

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

```
Ala Gln Trp Arg Gly Ala Ala Gly Thr Ala Ala Gln Ala Ala Val Val
1               5                   10                  15
```

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

```
Ala Ala Gly Thr Ala Ala Gln Ala Ala Val Val Arg Phe Gln Glu
1               5                   10                  15
```

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

```
Ala Ala Gln Ala Ala Val Val Arg Phe Gln Glu Ala Ala Asn Lys
1               5                   10                  15
```

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

```
Ala Val Val Arg Phe Gln Glu Ala Ala Asn Lys Gln Lys Ala Glu
1               5                   10                  15
```

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

```
Phe Gln Glu Ala Ala Asn Lys Gln Lys Ala Glu Leu Asp Glu Ile
1               5                   10                  15
```

```
<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Asn Lys Gln Lys Ala Glu Leu Asp Glu Ile Ser Thr Asn Ile
1               5                   10                  15

<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Lys Ala Glu Leu Asp Glu Ile Ser Thr Asn Ile Arg Leu Glu
1               5                   10

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 47

His His His His His His
1               5
```

METHODS AND COMPOSITIONS FOR DIAGNOSTIC ASSAYS FOR MEASURING CELL MEDIATED IMMUNE RESPONSE

CROSS REFERENCE TO RELATED APPLICATION

This Application is a 35 U.S.C. §371 National Phase Entry Application of International Application No. PCT/US2010/038312 filed Jun. 11, 2010, which designates the U.S., and which claims benefit under 35 U.S.C. §119(e) to U.S. Provisional Application 61/186,437, filed, Jun. 12, 2009, the entire contents of which is incorporated herein by reference.

FIELD OF THE INVENTION

The present application generally relates to a diagnostic assay, and more particularly an assay for measuring cell mediated immune (CMI) reactivity in a biological sample. More particularly, the present invention provides an assay and kit to measure a cell-mediated response to a target antigen in a biological sample using a transport factor to deliver the target antigen to a cell in a biological sample.

BACKGROUND OF THE INVENTION

Epidemiological surveys suggest that one-third of the world's population is infected with Mycobacterium tuberculosis. Primary infection leads to active tuberculosis (A-TB) in a minority (c. 10%) of infected individuals, usually within 2 years. In the remaining cases, the immune system contains the infection, and the individual is non-infectious and symptom-free. This clinical latency can persist throughout an individual's lifetime. However, in some circumstances, the host immune response is perturbed and latent tuberculosis infection (LTBI) may develop into post-primary A-TB. This process can occur, for example, following infection with human immunodeficiency virus (HIV), malnutrition, use of steroids or other immunosuppressive medications, or because of advanced age.

Development of new diagnostic tools would improve the control of tuberculosis (TB) by improving diagnosis of A-TB and by allowing a more accurate identification of LTBI. One such test is the tuberculin skin test (TST), which has been the only widely used tool available for diagnosing TB infection. However, this test is limited by its low sensitivity (75-90%) in diagnosing A-TB, and its low specificity, caused by the fact that the purified protein derivative (PPD) used for skin testing contains >200 antigens that are shared widely among environmental mycobacteria and the Mycobacterium bovis BCG strain used for vaccination. Lastly, TST does not allow discrimination between A-TB and LTBI.

For the detection of viral pathogens, existing diagnostic test kits detect viral proteins and some measure antibody against the viral antigens. Some assays allow for a more quantitative measure of the virus in the blood stream. However, none of these tests measure the T-cell response to the pathogenic infection. Studies have demonstrated that the T-cell response (or ability to elicit a CMI response to a target antigen expressed by a pathogen) can determine if the infection can be controlled by the immune system.

Other diagnostic tests have been developed which measure the cell-mediated immune (CMI) response to a pathogenic protein. Current methods for detecting CMI responses include skin tests measuring both immediate and delayed type hypersensitivity, lymphocyte proliferation assays and measurement of cytokines produced by purified mononuclear cells cultured with antigen.

Older established methods for determining a CMI response include a proliferation assay, use the uptake of radioactive isotopes by dividing T-cells as a marker for CMI reactivity. More recently, techniques such as a single cell assay (ELISpot) have been used to detect the number of T-cells producing certain cytokines in response to the antigenic stimulation. Furthermore, most in vitro methods for detecting CMI responses involve the purification of lymphocytes from whole blood, culturing these lymphocytes with an antigen for periods from 12 hours to 6 days and then detecting T-cell reactivity to the antigen.

Some CMI assays have been developed which detect a CMI response to a peptide of a target antigen, or overlapping peptides of a target antigen. Commercially available tests to measure a CMI response to a TB target antigen include the QuantiFERON® TB Gold test (from Cellestis Ltd) and the T SPOT TB test (from Oxford Immunotec). These tests detect a CMI response to overlapping peptides of the TB target antigen. In addition to diagnosis of pathogenic infections, such as TB, CMI diagnostic tests are also useful for immune diagnosis of many diseases and disorders, including infectious and autoimmune diseases, as well as markers for immunocompetence, and for detection of T-cell responses to endogenous and exogenous antigens (i.e. vaccines).

SUMMARY OF THE INVENTION

The present invention relates to methods for measuring CMI responses in a subject by incubating a biological sample from the subject which comprises T-cells or other cells of the immune system with a fusion protein, where the fusion protein comprises a polypeptide fragment of a Lethal Factor (LF) polypeptide fused to a target antigen. By measuring the cytokine response of the immune cells to the fusion protein, the level of the cytokine response as compared to a reference cytokine response is indicative of the level of a cell mediated immune (CMI) response of the subject to the antigen.

The present invention relates to the discovery that a polypeptide fragment of a Lethal factor (LF) fused to a target antigen can be used to deliver the target antigen to the cell in vitro, which can be used in a diagnostic test to determine the level of CMI responsiveness of a subject. The inventors have discovered by fusing the target antigen to a polypeptide fragment of LF, such as LFn, the diagnostic test can determine the CMI responsiveness of a subject to large antigens, in particular to whole antigens, rather than to antigen fragments as has been done previously. Furthermore, the inventors discovered that such coupling of a target antigen to a fragment of LF such as LFn resulted in a much higher accuracy of CMI responsiveness of the subject to the antigen than was previously possible when a diagnostic test was done when the target antigen was not coupled to a polypeptide fragment of LF.

Without wishing to be bound by theory, the inventors have previously demonstrated that LFn which was fused or coupled to a target antigen was able to deliver target antigens to the cytosol of a cell (in the absence of PA). Herein, the inventors have discovered that LFn coupled to a target antigen can be used in a diagnostic assay to determine if a subject has a cell mediated immune (CMI) response to the target antigen in the absence of PA. Also without wishing to be bound by theory, it is believed that the delivery of target antigen to the cytosol of an intact cell in a biological sample permits the cell to process and display the target antigen on its surface with MHC molecules, where the processed fragments can interact with antigen-specific cells, e.g., antigen-specific T cells, that may be present in the biological sample. Accordingly, the present invention relates to methods to measure a CMI response in a subject and compositions therefor, where the methods comprise incubating a biological sample from a subject which comprises cells capable of processing and presenting target antigen and immune cells, with a fragment of LF such as LFn or a fragment thereof which is coupled to a target antigen, for example an LFn-target antigen fusion protein, in order to deliver a target antigen to the cytosol of a cell in the biological sample. If immune cells that recognize the processed, displayed target antigen are present, they will, upon such recognition, release one or more cytokines indicative of a CMI response. The CMI response indicates exposure of the subject to the target antigen, e.g., infection with a pathogen or other exposure.

One aspect of the present invention provides a method and compositions for the detection of a CMI response of a subject to a target antigen which is fused to LFn, where the target antigen is a whole antigen protein, e.g., TB1 antigen. By being fused to LF, the target antigen is delivered to the cytoplasm of a cell, such as an antigen presenting cell (APC) in a biological sample obtained from a subject, for example a blood sample. If the subject has immune cells such as T cells which have been previously sensitized to the antigen (i.e. by exposure to a pathogen or infection with the pathogen which expresses the target antigen), the immune cell, such as a T-cell will release at least one cytokine, but likely a unique or characteristic panel or plurality of antigens, for e.g., IFN-g. The released cytokine(s) can be measured and the level of the cytokine(s) released and/or a specific profile of cytokines released will indicate that the subject has been infected, or previously exposed to the pathogen which expressed the target antigen. Any method to detect the level of one or more cytokines can be used; As a non-limiting example, the level of IFN-γ can be measured using a commercial IFN-γ ELISA assay as described herein in the Examples.

In particular embodiments, measurement of a unique or characteristic profile of cytokines increases the specificity and qualitative assessment of the CMI response to the target antigen. For example one can distinguish between a chronic infected subject vs. a carrier infected subject, or a subject infected with one subtype (or variant) of a pathogen vs. a different subtype (i.e. variant) of pathogen based on the release of a unique or characteristic profile or set of cytokines from the T-cells. By way of example, the cytokine profile of a chronically infected subject will be different from the cytokine profile of a carrier subject, and similarly a subject infected with one pathogen subtype will be different from the cytokine profile of a subject infected with a different pathogen subtype (i.e. variant).

A target antigen which can be fused to LFn can be any antigen associated with an infectious disease, or cancer or immune disease. In some embodiments, a target antigen fused to LFn can be expressed by a variety of infectious agents, including a pathogen, virus, bacterium, fungus or parasite.

Because an entire or whole target antigen can be fused to LFn and delivered via the LFN to the cytosol of an intact, living cell, the present invention enables detection of a CMI response to a whole or intact target polypeptide antigen. Previously developed CMI assays use peptides which can efficiently gain entry to the cell, rather than whole antigen protein, which cannot. Accordingly, the methods described herein provide as an advantage that the full range of epitopes for a given antigen can be employed, rather than just a single or selected few peptide epitopes. The target antigens for use in the present methods and compositions to detect a CMI response are not HLA restricted epitopes. Accordingly, described herein are methods and compositions for an assay to detect or monitor a CMI response which is more sensitive, in that it can diagnose exposure to antigen regardless of which epitope was instrumental in the individual's immune response.

In some embodiments, to avoid false positives associated with the increased sensitivity, one can also break the target antigen down into fragments of the whole target antigen, e.g., 3 or 4, depending on size of the protein. A positive CMI response to a whole target antigen fused to LFn can be confirmed by assessing a CMI response to a panel of target antigens fused to LFn which are fragments of the whole target antigen. A true CMI response is confirmed if one or two of the fragments to give a positive response, but not all fragments. If a positive CMI response is detected for all fragments, it is likely that the positive CMI response to a whole target antigen fused to LFn was a false positive.

In another aspect, the methods and compositions of the CMI assay are useful for prognosis evaluations of subjects. For example, as discussed above, one can use the CMI assay to distinguish between chronic infected subjects, carrier subjects or latently infected subjects. Alternatively, one can distinguish between subjects infected with different variants of a pathogen. In another embodiment, one can use the CMI assay as disclosed herein to identify which epitope of the target antigen is useful in the diagnosis and/or prognosis. This is useful to aid in the treatment of subjects, for example the CMI assay can be used to determine which epitope is predominant, and therefore can be used as a target to stimulate cells that respond to that epitope.

The present invention provides many advantages over existing cell mediated immune (CMI) assays. For example, the present invention provides a method to detect a CMI response to a panel of target antigens which are overlapping proteins or polypeptides of the target antigen, rather than overlapping peptides of the target antigen. The present approach using overlapping proteins of the target antigen fused to LFn enables less expensive and quicker production of the fusion proteins and increased stability which significantly decreases the cost of the assay. Furthermore, using overlapping proteins of a target antigen fused to LFn increases the specificity of the CMI response. For example, the CMI assay as disclosed herein enables one to distinguish the difference between a subject which has been immunized against a pathogen and a subject who is infected with or has been exposed to a pathogen. In another example, the CMI assay as disclosed herein can distinguish between the T cell target. Accordingly, the diagnostic methods and CMI assay as disclosed herein provide a simple, cheap and rapid method to detect a CMI response to a target antigen and/or detect a subject affected with a pathology (such as a pathogen infection).

Another advantage of the diagnostic methods and CMI assay as disclosed herein allows for earlier detection of the CMI response to a target antigen. For example, a CMI response can be detected a week or less from exposure to a pathogen or target antigen, whereas an antibody response can take months to reach measurable levels depending on the level and extent of exposure and/or infection. Another advantage of the diagnostic methods and CMI assay as disclosed herein is that a CMI response to a target antigen can be detected to a target antigen which is difficult to produce in bacteria.

In one embodiment, the methods described herein provide early asymptomatic screening system for a pathogenic infection by using the diagnostic assay as disclosed herein. Such screening can be performed, for example on a biological sample taken from the subject, including, but not limited to a blood sample, where the subject has been exposed to a pathogen, or where a subject is at risk of being infected with a pathogen infection. For example, where the subject is suspected of having a pathogenic infection, for instance the subject is showing symptoms characteristic to a particular pathogenic infection, or alternatively, the subject has been exposed to a pathogen (i.e. a subject has been in contact with a sample which comprises infective agent, or the subject been in contact with a person who has a pathogenic infection) a biological sample can be obtained from the subject and assessed for ability to elicit a CMI response to a target antigen which is expressed by the pathogen that the subject has been exposed to, or is at risk of being infected with the pathogen using the methods and compositions as disclosed herein. Because early detection of a pathogen infection or cancer is crucial for efficient treatment, identification of a pathogenic infection or the presence of cancer (e.g., as identified through a CMI response to a tumor marker) as disclosed herein vastly improves the chances of effective treatment.

Described herein are compositions for detecting or monitoring a CMI response in a subject, for example a mammalian subject such as a human subject. The present invention relates to compositions and methods of using the same to detect a CMI response in a subject, consisting essentially of a fragment of LF, such as a N-terminal Lethal Factor (LFn) of a bipartate exotoxin, or a carboxyl fragment thereof, where LFn is fused to or otherwise physically associated with the target antigen and the composition does not comprise a protective antigen (PA) of a bipartate exotoxin.

One aspect of the compositions and methods described herein relates to a method of measuring a cell mediated immune response (CMI) to a target antigen in a subject, the method comprising the steps of: (a) incubating a biological sample from the subject with at least one fusion polypeptide, the fusion polypeptide comprising a portion of a LF polypeptide, lacking LF enzymatic activity but sufficient to promote transmembrane delivery of the fusion polypeptide to a cell, fused to a target antigen polypeptide or to a fragment thereof, wherein the biological sample comprises cells of the immune system that release at least one cytokine in response to an antigen; (b) measuring the level of at least one cytokine released in the biological sample; and (c) comparing the level of the cytokine in the biological sample with a reference level of the same cytokine, wherein an increase in the level of the cytokine in the biological sample from the subject as compared to the cytokine reference level indicates a cell mediated immune response (CMI) to the target antigen.

Another aspect relates to a method of detecting a pathology of interest in a subject, the method comprising the steps of: (a) incubating a biological sample from the subject with at least one fusion polypeptide, the fusion polypeptide comprising a portion of a LF polypeptide lacking LF enzymatic activity but sufficient to promote transmembrane delivery of the fusion polypeptide to a cell, fused to a target antigen polypeptide or to a fragment thereof, wherein the target antigen is expressed in a tissue affected by the pathology, and wherein the biological sample comprises cells of the immune system that release at least one cytokine in response to an antigen; (b) measuring the level of at least one cytokine released in the biological sample; and (c) comparing the level of the cytokine in the biological sample with a reference level of the same cytokine, wherein an increase in the level of the cytokine in the biological sample from the subject as compared to the cytokine reference level identifies the subject as having, or having an increased risk of having said pathology.

Another aspect relates to a method of measuring a cell mediated immune response (CMI) to a target antigen in a subject, the method comprising the steps of: (a) incubating a biological sample from the subject with at least one target antigen, wherein the biological sample comprises cells of the immune system that release at least one cytokine following stimulation by the target antigen; (b) measuring the presence or level of a cytokine released in the biological sample wherein the presence or level of the cytokine indicates the presence of a cell mediated immune response (CMI) to the target antigen in the biological sample from the subject, wherein the improvement comprises, in incubating step (a), incubating the biological sample with at least one target antigen polypeptide or a fragment thereof fused to a portion of a LF polypeptide lacking LF enzymatic activity but sufficient to promote transmembrane delivery of the fusion polypeptide to a cell.

In some embodiments, the method comprises use of a portion of a LF polypeptide which is at least the 60 carboxy-terminal amino acids of SEQ ID NO: 3, or a conservative substitution variant thereof, including a conservative substitution variant that promotes transmembrane delivery. In some embodiments, the LF polypeptide fragment comprises at least the 80 carboxy-terminal amino acids of SEQ ID NO: 3, or a conservative substitution variant thereof, including a conservative substitution variant that promotes transmembrane delivery, or at least the 104 carboxy-terminal amino acids of SEQ ID NO: 3, or a conservative substitution variant thereof, including a conservative substitution variant that promotes transmembrane delivery. In some embodiments, the portion of a LF polypeptide comprises the amino acid sequence corresponding to SEQ ID NO: 3 or a conservative substitution variant thereof, including a conservative substitution variant that promotes transmembrane delivery. In some embodiments, the LF polypeptide does not bind to a PA polypeptide.

In another embodiment, a portion of a LF polypeptide used in the methods and compositions as disclosed herein substantially lacks amino acids 1-33 of SEQ ID NO: 3. As used in this context, the term "substantially lacks" means that the LF polypeptide lacks a signal peptide function.

In another embodiment, a portion of a LF polypeptide used in the methods and compositions as disclosed herein consists of SEQ ID NO: 4, or a conservative substitution variant thereof that promotes transmembrane delivery.

One some embodiments, a LF polypeptide fragment as used in the methods and compositions as disclosed herein is coupled to a target antigen, for example a target antigen polypeptide or a fragment thereof of at least 15 amino acids in length. In some embodiments, such a target antigen polypeptide or a fragment thereof is folded in its native conformation. In some embodiments, the target antigen polypeptide or a fragment thereof is part of a multi-molecular polypeptide complex, or alternatively is a subunit polypeptide of a multi-molecular polypeptide target antigen. In another embodiment, a target antigen polypeptide is substantially one half the size of the full length target antigen, or alternatively substantially one third, or one quarter of the size of the full length target antigen, or less than one quarter of the size of the full length target antigen and wherein said fragment is at least 15 amino acids in length.

In some embodiments, the methods and compositions as disclosed herein measure the CMI response in a biological sample, for example but not limited to a whole blood sample, or a plasma or lymph node biological sample. Typically, the biological sample comprises immune cells, including, but not limited to NK cells; T-cells; B-cells; Th cells; Th1 cells; Th2 cells; Tc cells; stromal cells; endothelial cells; leukocytes; lympocytes; dendritic cells; macrophages; mast cells and monocytes. The biological sample comprises cells capable of processing and displaying the target antigen.

In some embodiments, the methods and compositions as disclosed herein measure the level of cytokines released from the immune cells in response to the target antigen, for example, such cytokines can be any one of the following, or any combination of cytokines including but not limited to: GM-CSF; IL-1α; IL-1β; IL-2; IL-3; IL-4; IL-5; IL-6; IL-7; IL-8; IL-10; IL-12; IFN-α; IFN-β; IFN-γ; MIP-1α; MIP-1β; TGF-β; TNFα and TNFβ. In particular embodiments, where a T-cell cytokine is measured, the cytokine can be any one or a combination of the following cytokines: IFN-g; TGFβ; TNFβ; IL-10; GM-CSF; IL-3; IL-4 and IL-5. In particular embodiments, a cytokine which is measured is IFN-γ.

One aspect of the present invention relates to the detection of a CMI response and/or the diagnosis of a subject as having a pathology of interest, including, but not limited to a pathogenic infection, or cancer or an autoimmune disease.

An antigen associated with an infectious disease can be derived from any of a variety of infectious agents, including a pathogen, virus, bacterium, fungus or parasite. Non-limiting examples of pathogens of interest include Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus, Rinderpest, Rhinovirus, Echovirus, Papova virus, Echinovirus, Arbovirus, Human Immunodeficiency virus type I or type II and Simian Immunodeficiency virus.

Examples of bacteria for which immune detection can be provided include, but are not limited to, *M. tuberculosis, mycobacterium, mycoplasma, neisseria* and *legionella*. Examples of parasites include, but are not limited to, rickettsia and chlamydia.

One example of an infectious disease antigen is TbH9 (also known as Mtb 39A), a tuberculosis antigen. Other tuberculosis antigens include, but are not limited to DPV (also known as Mtb8.4), 381, Mtb41, Mtb40, Mtb32A, Mtb9.9A, Mtb9.8, Mtb16, Mtb72f, Mtb59f, Mtb88f, Mtb71f, Mtb46f and Mtb31f Cr indicates that it is a fusion or two or more proteins).

Accordingly, in such embodiments where diagnosis or detection is of a subject with a CMI response to a pathology of interest, the target antigen polypeptide or fragment thereof is an antigen of a pathogen, for example, a TB-specific antigen. An example of a TB-specific antigen includes a TB1 (CFP or CFP-10) polypeptide comprising SEQ ID NO: 7 or a fragment thereof such as polypeptide sequences SEQ ID NO: 30 to SEQ ID NO: 46. Another TB-specific antigen which can be used is a TB2 (ESAT or ESAT-6) polypeptide comprising SEQ ID NO: 6 or a fragment thereof, such as polypeptide sequences SEQ ID NO: 8 to SEQ ID NO: 29.

In some embodiments, a cytokine is measured at the level of protein expression, using any method commonly known by persons of ordinary skill in the art, for example, using an antibody, antibody fragment, recombinant antibody, chimeric antibody, aptamer, peptide or analogue thereof. Alternatively, one can measure a cytokine using a method selected from the group consisting of: an immunoassay, a radioimmunoassay (RIA), an immunoradiometric assay (IRMA), an enzyme-linked immunosorbent assay (ELISA); an ELISpot; CELISA [cellular enzyme-linked immunosorbent assay]; a RHPA (reverse hemolytic plaque assay) or a kinase receptor activation assay (KIRA).

Typically the methods and compositions as disclosed herein are useful in the diagnosis or determining a CMI response in or of a subject, such as a mammalian subject including a human subject, however, the methods and compositions are equally applicable to non-human subjects, including livestock, domestic and companion animals, and other veterinary and wild-life subjects.

In some embodiments, a biological sample is incubated with a panel of fusion polypeptides comprising an LFn polypeptide fused to a target antigen polypeptide or fragment thereof, wherein the panel of fusion polypeptides comprises target antigen polypeptides or fragments thereof which substantially cover the entire full-length of the target antigen polypeptide. In some embodiments, a panel of fusion polypeptides is a plurality of LFn polypeptides fused to different target antigen polypeptides that are overlapping and/or adjacent target antigen polypeptide fragments which substantially cover the entire full-length of the target antigen polypeptide. A panel of fusion polypeptides can be any number of fusion polypeptides, for example at least 2, or at least between 2-5, or between 6-10, or between 11-15 or between 16-20 or more than 20 fusion polypeptides.

In one embodiment, a panel of fusion polypeptides useful in the methods and compositions as disclosed herein comprises a LF polypeptides fused to at least two different target antigen fragments selected from the group consisting of: SEQ ID NO: 8 to SEQ ID NO: 29. In an alternative embodiment, a panel of fusion polypeptides useful in the methods and compositions as disclosed herein comprises at least two said LF polypeptides fused to different target antigen fragments selected from the group consisting of: SEQ ID NO: 30 to SEQ ID NO: 46.

In some embodiments, the detection of a CMI response (i.e. a positive reactivity to a CMI response) identifies the subject to have, or be at risk of having a pathology. Examples of such pathologies which can be identified by the methods and compositions as disclosed herein include, but are not limited to: cancers, infectious diseases and autoimmune diseases. Furthermore, the detection of a CMI response (i.e. a positive reactivity to a CMI response) using the methods and compositions as disclosed herein is also useful to identify a subject which has likely been exposed to a target antigen, or a pathogen which expresses the target antigen. In some embodiments, where a subject has been identified to have a positive CMI response, the subject is identified to have, or to be likely to have a better prognosis as compared to a subject who is identified to have a low or negative ability to elicit a CMI response.

Another aspect relates to a method for monitoring a pathology of interest in a subject, the method comprising assessing the ability of a subject to elicit a cell mediated immune (CMI) response to a target antigen, wherein the method comprises: (a) incubating a biological sample collected from the subject at a test timepoint, with a fusion polypeptide comprising a portion of a LF polypeptide lacking LF enzymatic activity but sufficient to promote transmembrane delivery of the fusion polypeptide to a cell, the LF polypeptide fused to a target antigen polypeptide or fragment thereof, wherein the target antigen is expressed in a tissue affected by the pathology, and wherein the biological sample comprises cells of the immune system that release at least one cytokine in response to an antigen; (b) measuring the level of at least one cytokine released in the biological sample; and (c) comparing the level of said cytokine in the biological sample with a reference level of the same cytokine, wherein if an increase in the level of the cytokine in the biological sample obtained from the subject at the test timepoint is detected as compared to the reference level of said cytokine, then the subject is identified as having the ability to elicit a cell mediated immune (CMI) response to the target antigen polypeptide or fragment thereof.

In such embodiments, a reference cytokine level is the level of the cytokine from at least one, or a plurality of biological samples obtained from one or more subjects not affected by said pathology. Alternatively, a reference cytokine level is the level of the cytokine from a biological sample obtained from the subject at an earlier timepoint than the test timepoint.

Where a subject is identified to have a positive CMI response (i.e. elicit a CMI response to the target antigen) the present invention encompasses a further step of treating the subject identified to have an ability to elicit a cell mediated (CMI) response with a suitable therapeutic protocol. Alternatively, the methods and compositions as disclosed herein are useful for directing an appropriate treatment in a subject identified to have a positive CMI response. For example, a practitioner can review the levels of the cytokines from the CMI assay as disclosed herein, and if the subject is identified to have an ability to elicit a cell mediated (CMI) response, draw conclusions with regard to the specific, as opposed to generalized agent involved in the pathology. The practitioner can then direct the treat,ent of the subject with a therapeutic protocol appropriate for the specific agent involved.

In another embodiment, the methods and compositions as disclosed herein are useful for predicting prognosis of the pathology in the subject, for example, where a subject which can elicit a cell mediated (CMI) response is identified as likely to have a better prognosis as compared to a subject who is identified to have a low or negative ability to elicit a CMI response. In another embodiment, the methods and compositions as disclosed herein are useful for predicting the risk of a subject developing a pathology, for example, a subject which is identified to have an ability to elicit a cell mediated (CMI) response is identified as less likely to develop the pathology as compared to a subject who is identified to have a low or negative ability to elicit a CMI response. In such embodiments, the pathology can be any pathology, including but not limited to a pathogenic infection, a cancer or an autoimmune disease.

In some embodiments, the methods and compositions as disclosed herein comprise a portion of a *Bacillus anthracis* LF polypeptide which at least the 60 carboxy-terminal amino acids of SEQ ID NO: 3, or a conservative substitution variant thereof, including a conservative substitution variant thereof that promotes transmembrane delivery. Alternatively, a portion of a LF polypeptide useful in the methods and compositions herein is at least the 80 carboxy-terminal amino acids or a conservative substitution variant thereof, including a conservative substitution variant thereof that promotes transmembrane delivery, or at least the 104 carboxy-terminal amino acids of SEQ ID NO: 3 (also referred to herein as Fragment 3), or a conservative substitution variant thereof, including a conservative substitution variant thereof that promotes transmembrane delivery. In one embodiment, a portion of a LF polypeptide comprises the amino acid sequence corresponding to SEQ ID NO: 3 or SEQ ID NO: 4 or a conservative substitution variant thereof, including a conservative substitution variant thereof that promotes transmembrane delivery.

In another embodiment, a portion of a LF polypeptide useful in the methods and compositions as disclosed herein does not bind B. anthracis PA polypeptide, for example, the LFn polypeptide can substantially lack amino acids 1-33 of SEQ ID NO: 3.

In some embodiments, a target antigen polypeptide or fragment thereof which is fused to an LF polypeptide, e.g., an LFn polypeptide, is at least 15 amino acids in length. Typically, such a target antigen polypeptide or fragment thereof is folded in its native conformation. In some embodiments, a target antigen is part of a multi-molecular polypeptide complex, for example, a target antigen can be a subunit of a multi-molecular polypeptide target antigen. In some embodiments where a fragment of a target antigen is fused to a portion of a LF polypeptide, the fragment can be a range of sized fragments of the whole antigen, including, but not limited to a fragment substantially one half the size of the full length target antigen, or substantially one third the size of the full length target antigen, or substantially one quarter of the size of the full length target antigen, or alternatively less than one quarter of the size of the full length target antigen. Typically a fragment of a target antigen fused to a portion of a LF polypeptide is at least 20 amino acids.

The biological sample useful in the methods and compositions as disclosed herein can be any biological sample comprising immune cells, including, but not limited to a whole blood sample, or a plasma or lymph node biological sample. A useful biological sample for the methods described herein comprises at least one type of immune cell, for example an immune cell such as, but not limited to NK cells, T-cells, B-cells, Th cells, Th1 cells, Th2 cells, Tc cells, stromal cells, endothelial cells, leukocytes, lympocytes, dendritic cells, macrophages, mast cells and monocytes. In particular embodiments, a biological sample comprises a T-cell. In given embodiments, the biological sample comprises a cell that processes and displays antigen delivered to the cytosol of the cell.

Useful biological samples comprise immune cells which release at least one cytokine in response to recognition of the target antigen (e.g., by binding of a receptor on the immune cell). Examples of such cytokines released can be any type of cytokine, for example but not limited to, GM-CSF, IL-1α, IL-β, IL-2, IL-3, IL-4, IL-5, IL-6, IL-7, IL-8, IL-10, IL-12, IFN-α, IFN-β, IFN-γ, MIP-1α, MIP-1β, TGF-1β, TNFα and TNFβ. In some embodiments, the level of a cytokine measured in the methods as disclosed herein is the level of a T-cell cytokine, such as for example the level of at least one of the following cytokines: IFN-γ, TGFβ, TNFβ, IL-10, GM-CSF, IL-3, IL-4 and IL-5. In particular embodiments, the cytokine which is measured is IFN-γ. One can measure the level of a cytokine by any method commonly known by one of ordinary skill in the art, for example by an immunoassay, a radioimmunoassay (RIA), an immunoradiometric assay (IRMA), an enzyme-linked immunosorbent assay (ELISA); an ELISpot; a CELISA [cellular enzyme-linked immunosorbent assay; a RHPA (reverse hemolytic plaque assay) or a kinase receptor activation assay (KIRA), or measuring the level of cytokine protein expression using common protein detection agents such as an antibody, humanized antibody, antibody fragment, recombinant antibody, chimeric antibody, aptamer, peptide or analogue thereof.

In some embodiments, a target antigen polypeptide or fragment thereof which is fused to an LF polypeptide useful in the methods and compositions as disclosed herein is a pathogen target antigen. Examples of such pathogens which express a target antigen for use in the invention herein include, but are not limited to Myocobacterium tuberculosis (TB), Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus, Rinderpest, Rhinovirus, Echovirus, Papova virus, Echinovirus, Arbovirus, Human Immunodeficiency virus type I or type II and Simian Immunodeficiency virus.

In some embodiments, a target antigen polypeptide or fragment thereof which is fused to LFn is expressed by the pathogen Myocobacterium tuberculosis. For example, one such target antigen which is fused to LFn and is useful in the methods and compositions as disclosed herein is a TB-specific antigen, such as a TB1 (CFP) polypeptide or a fragment thereof or a TB2 (ESAT) polypeptide or a fragment thereof.

The methods and compositions described herein are useful to determine a CMI response to a target antigen in a subject, for example a mammalian subject such as a human subject.

Another aspect of the present invention is related to a kit for measuring a cell mediated immune (CMI) response to a target antigen polypeptide in a biological sample from a subject, the kit comprising a fusion polypeptide comprising a portion of a LF polypeptide lacking LF enzymatic activity but sufficient to promote transmembrane delivery of the fusion polypeptide to a cell, fused to a target antigen polypeptide or fragment thereof.

In such embodiments, the kit can comprise a portion of a LF polypeptide which is or includes at least the 60 carboxy-terminal amino acids of SEQ ID NO: 3, or a conservative substitution variant thereof, including a conservative substitution variant thereof that promotes or mediates transmembrane delivery. Alternatively, a portion of a LF polypeptide useful in a kit is at least the 80 carboxy-terminal amino acids, or at least 104 carboxy-terminal amino acids of SEQ ID NO: 3 (also referred to herein as Fragment 3), or a conservative substitution variant thereof, including a conservative substitution variant thereof that promotes or mediates transmembrane delivery. In one embodiment, a portion of a LF polypeptide comprises the amino acid sequence corresponding to SEQ ID NO: 3 or SEQ ID NO: 4 or a conservative substitution variant thereof, including a conservative substitution variant thereof that promotes or mediates transmembrane delivery.

Typically, a kit as disclosed herein comprises a panel of fusion polypeptides. For example, a panel of fusion polypeptides can be comprised of substantially contiguous target antigen fragments which together substantially cover the full-length of the target antigen polypeptide. A panel of fusion polypeptides can be any number of fusion polypeptides, for example but not limited to at least 2, or at least 2-5, or 6-10, or 11-15 or 16-20 or more than 20 fusion polypeptides. In some embodiments, a kit can comprise a panel of fusion polypeptides of at least two LF polypeptides fused to different target antigen fragments selected from the group consisting of: SEQ ID NO: 8 to SEQ ID NO: 29. In an alternative embodiment, a panel of fusion polypeptides useful in the kits as disclosed herein comprises B. anthracis LF polypeptides fused to at least two different target antigen fragments selected from the group consisting of: SEQ ID NO: 30 to SEQ ID NO: 46.

Another aspect of the present invention relates to a kit for measuring a cell mediated immune (CMI) response to a target antigen polypeptide in a biological sample from a subject, the kit comprising: (a) a portion of a LF polypeptide lacking LF enzymatic activity but sufficient to promote transmembrane delivery of said fusion polypeptide to a cell; (b) reagents to conjugate the portion of a LF polypeptide to a target antigen polypeptide or fragment thereof; and (c) antibody-based detection means to detect at least one cytokine released from the biological sample.

Another aspect of the present invention relates to a kit for measuring a cell mediated immune (CMI) response to a TB antigen polypeptide of a biological sample from a subject, the kit comprising: (a) a portion of a LF polypeptide lacking LF enzymatic activity but sufficient to promote transmembrane delivery of said fusion polypeptide to a cell, fused to a TB-specific antigen polypeptide; and (b) antibody-based detection means to detect at least one cytokine released from the biological sample.

In some embodiments, a kit as disclosed herein can optionally further comprise a positive and/or a negative biological sample control, wherein a positive sample elicits a CMI response to the target antigen, and a negative biological sample elicits negligible or no CMI response. One such kit as disclosed herein comprises a TB-specific antigen polypeptide which is TB1 (CFP) polypeptide of SEQ ID NO: 7 or a fragment thereof, and/or a TB2 (ESAT) polypeptide of SEQ ID NO: 6 or a fragment thereof. In some embodiments, the kit can comprise a panel of target antigen fusion polypeptides, where the target antigen is a fragment of TB1 (SEQ ID NO: 7), such as fragments selected from SEQ ID NO: 30 to SEQ ID NO: 46, or a fragment of TB2 (SEQ ID NO: 6), such as fragments selected from SEQ ID NO: 8 to SEQ ID NO: 30.

BRIEF DESCRIPTION OF THE DRAWINGS

" FIG. 2A shows use of a CMI assay as disclosed herein at the initial stages of a pathogenic infection (e.g., an HBV infection) which can identify a subject who will become a chronic HBV carrier (i.e. subjects who have viral loads which remain high with detectable viral surface antigen) and subjects who are non-chronic carriers (i.e. subjects which have low viral loads and low viral surface antigen). The discrimination of the subjects enables early treatment of chronic carriers and therapeutic strategies to prevent liver disease. FIG. 2B shows a schematic for distinguishing the CMI response to a target antigen of a subject who is a chronic carrier versus a subject who is a non-chronic carrier. A chronic carrier will have a unique or characteristic cytokine profile to the target antigen whereas the non-chronic carrier will not have the same cytokine profile.

FIG. 3A shows 77 fresh blood samples obtained from Haikou TB center were stimulated by QTG and AT stimulators within 18 hours respectively. IFNΞ level was tested using QFT ELISA plates. The match rate between QTG and AT was ~90% (89.6 precisely). FIG. 3B is a table showing the Comparison of QuantiFERON TB Gold and ASACIR TB kit stimulators using Haikou TB center 77 samples.

FIG. 4 shows a table of results from samples from the Haikou TB center, showing eight out of a total of 77 TB center cases tested which showed a different response using either the QTG and AT stimulator respectively.

FIG. 5A shows SDS-PAGE of positive control samples which contain TB1, TB2 and TB1+TB2 proteins. FIG. 5B shows a western blot analysis of plasma samples (after PBS stimulation) using a primary antibody at 1:100 dilution; Anti-human-IgG-HRP was used as secondary antibody at 1:1000 dilution. FIG. 5C shows the same membrane as shown in FIG. 5B which was stripped and probed with anti-his antibody at 1:1000 dilution, and anti-mouse-AP was used as secondary antibody at 1:1000 dilution. 6 ug of CFP & ESAT (each) was loaded in each well. The proteins were produced under GMP environment. Shown in each lane is: M: Marker; Lane:1: Sample T0602-2, TB Gold positive (0.35 IU/ml), but LF-CMI negative (0.30 IU/ml); Lane 2: Sample T0604-3, TB Gold positive (0.53 IU/ml), but LF-CMI negative (0.22 IU/ml); Lane 3: Sample T0606-2, TB Gold negative (-0.01 IU/ml), but LF-CMI positive (0.70 IU/ml); Lane 4: Sample T0613-3, TB Gold positive (2.64 IU/ml), but LF-CMI negative (0.30 IU/ml); Lane 5: Sample T0613-4, TB Gold positive (0.84 IU/ml), but LF-CMI negative (0.20 IU/ml); Lane 6: Sample T0616-2, TB Gold negative (0.00 IU/ml), but LF-CMI positive (3.09 IU/ml); Lane 7: Sample T0619-1, TB Gold positive (5.48 IU/ml), but LF-CMI negative (0.20 IU/ml); Lane 8: Sample T0620-2, TB Gold positive (3.17 IU/ml), but LF-CMI negative (0.29 IU/ml); Lane 9: Sample T0604-5, both TB Gold (0 IU/ml) and LF-CMI negative (0.04 IU/ml); Lane 10: Sample T0604-2, both TB Gold (4.99 IU/ml) and LF-CMI positive (2 IU/ml).

FIG. 7 shows a table of 20 from a total of 40 cases from the Hainan Provincial Hospital which showed a different response using QTG and AT stimulator respectively.

FIG. 8A shows a western blot analysis of plasma samples (with PBS stimulation), in which the primary antibody was used at 1:100 dilution; Anti-human-IgG-HRP was used as secondary antibody at 1:1000 dilution. FIG. 8B shows the same membrane as shown in FIG. 8A which was stripped and probed with anti-his antibody at 1:1000 dilution, and anti-mouse-AP was used as secondary antibody at 1:1000 dilution. 6ug of CFP & ESAT (each) was loaded in each well. The proteins were produced under GMP environment. Shown in each lane is M: Marker; Lane:1: Sample T0612-6, TB Gold negative (0.01 IU/ml), but LF-CMI positive (2.23 IU/ml); Lane 2: Sample T0603-7, TB Gold negative (0.17 IU/ml), but LF-CMI positive (9.11 IU/ml); Lane 3: Sample T0603-10, TB Gold negative (-0.02 IU/ml), but LF-CMI positive (3.99 IU/ml); Lane 4: Sample T0604-6, TB Gold negative (0.01 IU/ml), but LF-CMI positive (0.74 IU/ml); Lane 5: Sample T0604-7, TB Gold negative (-0.01 IU/ml), but LF-CMI positive (0.52 IU/ml); Lane 6: Sample T0604-8, TB Gold negative (0.03 IU/ml), but LF-CMI positive (1.50 IU/ml); Lane 7: Sample T0604-9, TB Gold negative (0.01 IU/ml), but LF-CMI positive (0.47 IU/ml); Lane 8: Sample T0604-10, TB Gold negative (0.03 IU/ml), but LF-CMI positive (2.81 IU/ml); Lane 9: Sample T0616-6, TB Gold negative (-0.01 IU/ml), but LF-CMI positive (4.08 IU/ml); Lane 10: Sample T0616-7, TB Gold negative (0.06 IU/ml), but LF-CMI positive (2.12 IU/ml); Lane 11: Sample T0604-5, both TB Gold (0 IU/ml) and LF-CMI negative (0.04 IU/ml); Lane 12: Sample T0604-2, both TB Gold (4.99 IU/ml) and LF-CMI positive (1 IU/ml).

FIG. 9A shows a western blot analysis of plasma samples (with PBS stimulation) where a primary antibody was used at 1:100 dilution; Anti-human-IgG-HRP was used as secondary antibody at 1:1000 dilution. FIG. 9B shows the same membrane as shown in FIG. 9A which was stripped and probed with anti-his antibody at 1:1000 dilution, and anti-mouse-AP was used as secondary antibody at 1:1000 dilution. 6 ug of CFP & ESAT (each) was loaded in each well. The proteins were produced under GMP environment. Shown in each lane are: M: Marker; Lane:1: Sample T0605-5, TB Gold negative (0.00 IU/ml), but LF-CMI positive (1.69 IU/ml); Lane 2: Sample T0605-8, TB Gold negative (0.00 IU/ml), but LF-CMI positive (0.57 IU/ml); Lane 3: Sample T0605-10, TB Gold negative (-0.01 IU/ml), but LF-CMI positive (0.51 IU/ml); Lane 4: Sample T0604-6, TB Gold negative (-0.14 IU/ml), but LF-CMI positive (0.73 IU/ml); Lane 5: Sample T0604-7, TB Gold negative (0.00 IU/ml), but LF-CMI positive (1.24 IU/ml); Lane 6: Sample T0612-8, TB Gold negative (0.01 IU/ml), but LF-CMI positive (1.76 IU/ml); Lane 7: Sample T0612-11, TB Gold negative (0.0 IU/ml), but LF-CMI positive (0.46 IU/ml); Lane 8: Sample T0612-12, TB Gold negative (0.04 IU/ml), but LF-CMI positive (4.49 IU/ml); Lane 9: Sample T0612-13, TB Gold negative (0.01 IU/ml), but LF-CMI positive (0.85 IU/ml); Lane 10: Sample T0612-14, TB Gold negative (-0.02 IU/ml), but LF-CMI positive (1.17 IU/ml); Lane 11: Sample T0604-5, both TB Gold (0 IU/ml) and LF-CMI negative (0.04 IU/ml); Lane 12: Sample T0604-2, both TB Gold (4.99 IU/ml) and LF-CMI positive (2 IU/ml).

FIG. 11 shows a table of the comparison of the CMI assay described herein (termed ASCIR in FIG. 11). The Postitive Predictive value (PPV) of the LF-CMI assay is 96.2% (PPV=51/(51+2)=96.2%). Thus, the LF-CMI assay has a very high positive predictive value, for example, of the 53 TB positive samples detected using the LF-CMI assay, 51 of these were also detected to be positive using the TB Gold assay. The Negative Predictive value (NPV) of the LF-CMI assay is 100% (NPV=7/(0+7)=100%). Thus, the LF-CMI assay has a very high negative predictive value, for example, of the 7 TB negative samples detected using the LF-CMI assay, all of these were also detected to be negative using the TB Gold assay.

FIGS. 12A-12C show a comparison of the LF-CMI or VTI kit (e.g., the ASCIR test) with the TB culture, or the TB smear. FIG. 12A shows a comparison of positive identified samples with the VTI kit and the TB culture test. Of the 21 samples tested, 20 samples identified to be positive using the VTI kit, whereas only 7 were identified to be TB positive using the TB culture kit. FIG. 12B shows a comparison of positive identified samples with the VTI kit and the TB smear test. Of the 21 samples identified to be TB positive using the TB smear kit, 20 where also identified to be positive using the VTI kit, demonstrating that the VTI kit is senitive and is correlative with the TB smear test. FIG. 12C shows a comparison of the TB smear and the TB culture tests. Of the same 21 samples, all 21 samples were identified positive using the TB smear test, wereas only 7 were identified to be positive using the TB culture test. All 21 samples used in FIGS. 12A-12B are from TB smear positive samples.

FIG. 17A shows that using the skin test, 100% of the subjects were TB positive, where 79.9% of the subjects tested either positive (++) (53.6%) or strong positive (+++) (25.3%). In comparison, 30.1% of the subjects were positive with the ASCIR TB test, with 30 subjects (18.1%) testing positive (++) and 14 subjects (25.3%) testing strong positive (+++) with the ASCIR TB test. FIG. 17B shows that 61.3% of the subjects who underwent the physical test were skin test postive (PPD+) and 38.7% of the subjects tested are skin test (PDD) negative.

DETAILED DESCRIPTION OF THE INVENTION

Figure 1:
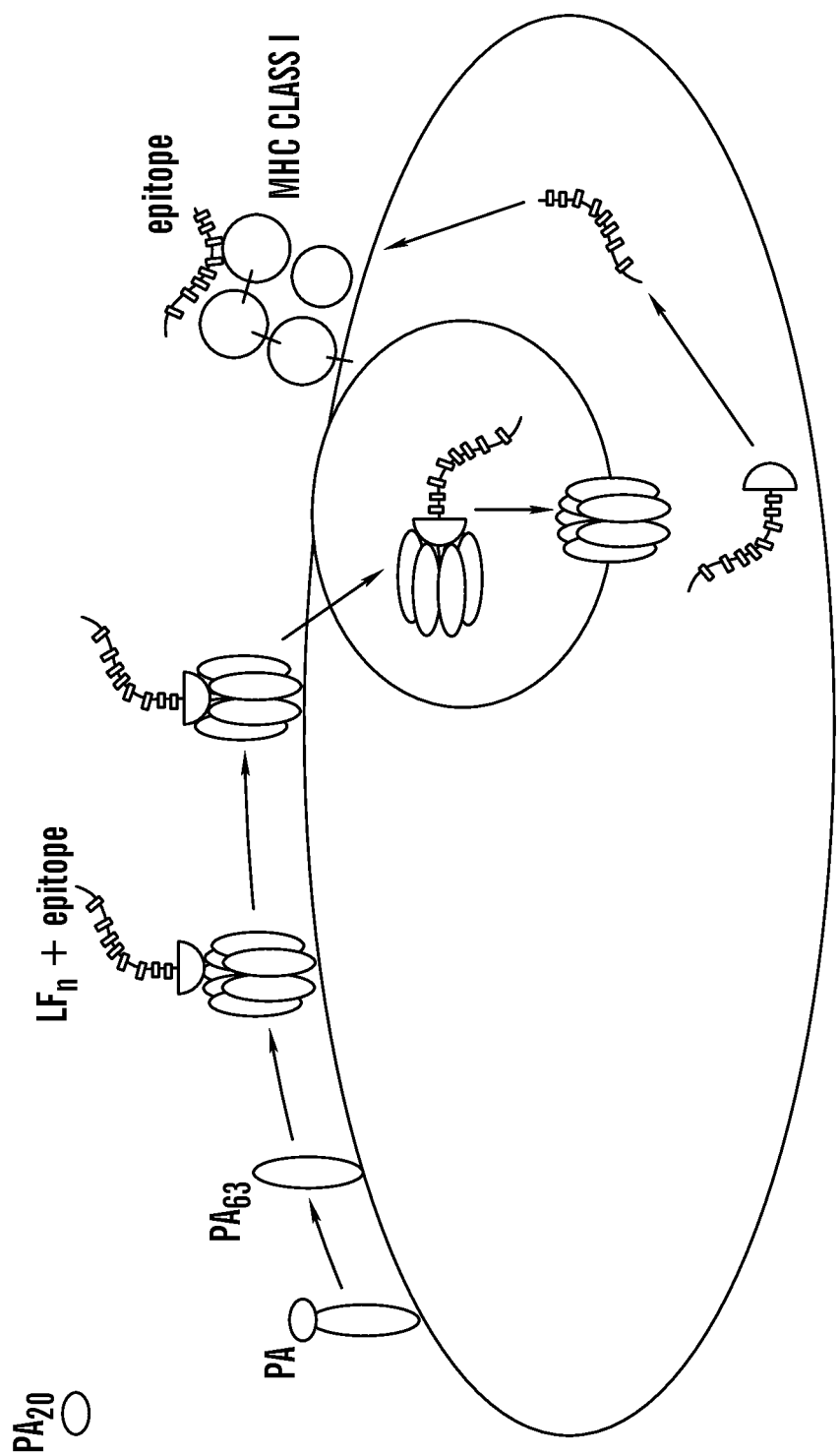
FIG. 1 is a drawing depicting the PA-mediated entry of LFn into a cell via endocytosis, and subsequent presentation by MHC Class I molecules.
Figure 2A:
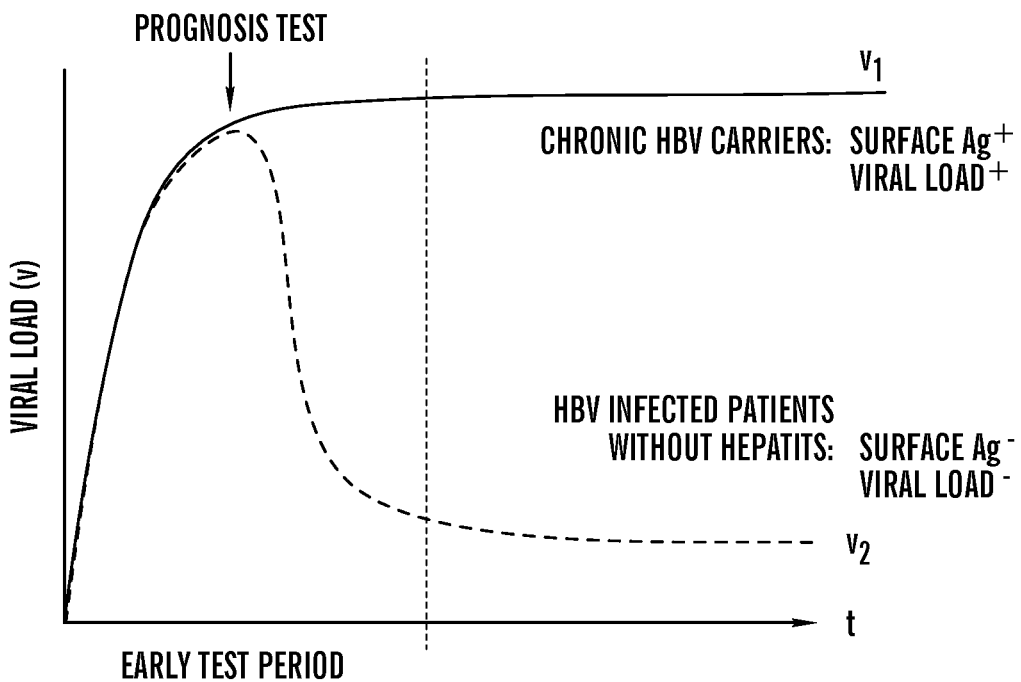
FIGS. 2A-B show schematic representations of the CMI assay, also referred to herein as the "LF-CMI assay," or alternatively, the VTI assay, or "ASACIR TB kit
Figure 2B:
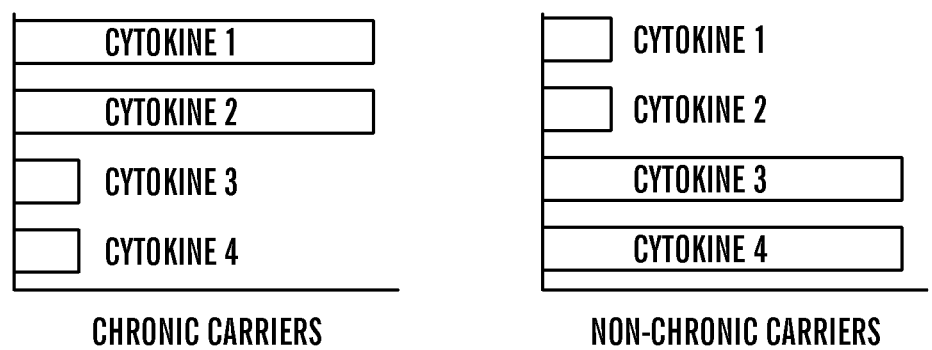
Figures 3A, 3B:
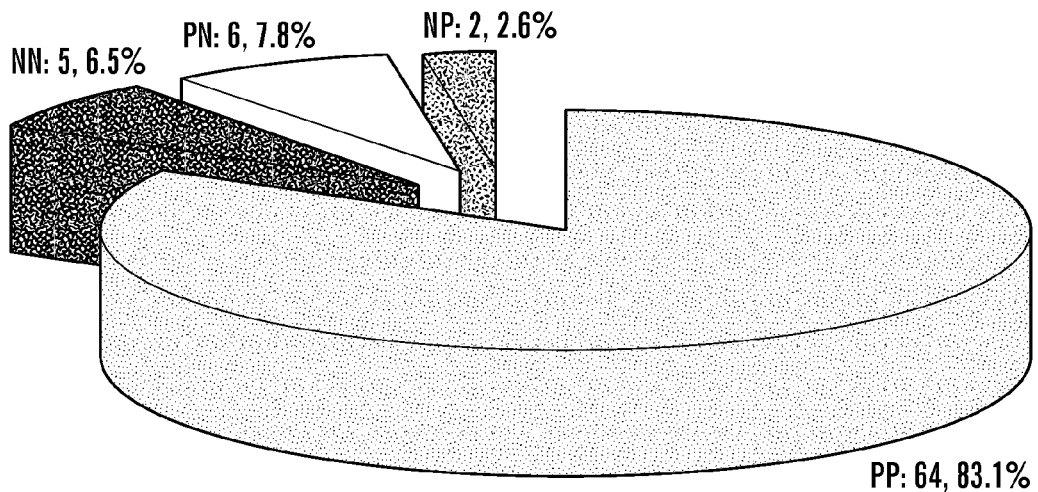
FIG. 3A-3B shows the Comparison of QuantiFERON TB Gold (QTG) and ASACIR TB (AT) kit stimulators using Haikou TB center 77 samples.
Figure 5A:
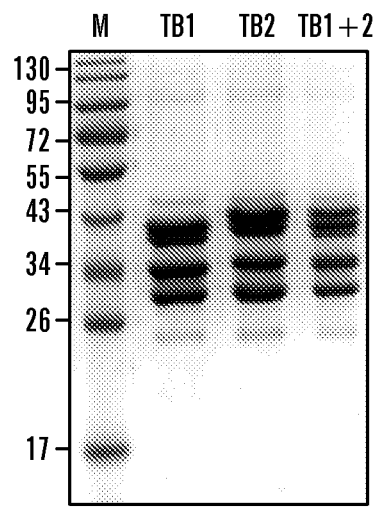
FIG. 5A-5C show Western blot analysis using TB1 (CFP) and TB2 (ESAT) for eight cases shown in FIG. 4.
Figure 5B:
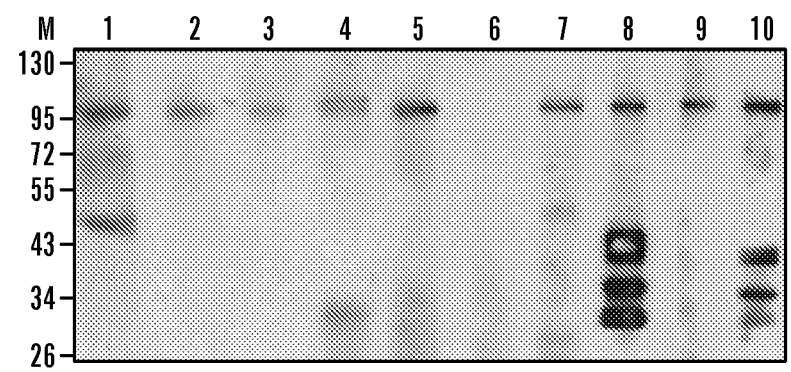
Figures 5C, 6:
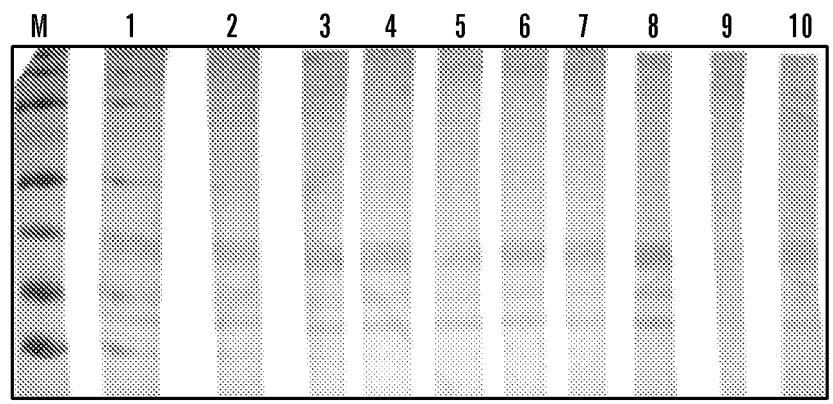
FIG. 6 shows the comparison of QuantiFERON TB Gold (QTB) and ASACIR TB (TB) kit stimulators using Hainan Provincial Hospital cases 40 samples. Forty fresh blood samples obtained from Hainan Provincial Hospital were stimulated by QTG and AT stimulators within 18 hours respectively. IFNy level were tested using QFT ELISA plates. Twenty out of 40 cases appeared negative using QTG stimulators, but all were positive using the AT stimulator, as determined by Western Blot. analysis
Figure 8A:
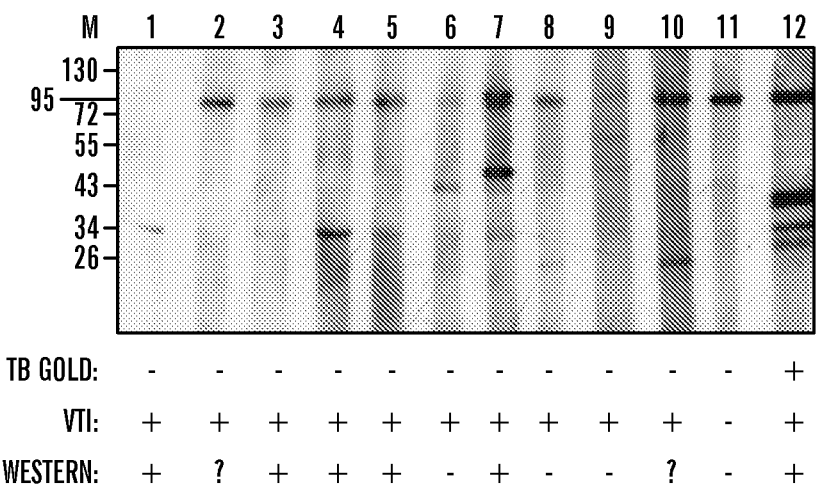
FIG. 8A-8B show Western blot analysis using GMP TB1 (CFP) and TB2 (ESAT) for samples 1-10 of the 20 cases shown in FIG. 7.
Figure 8B:
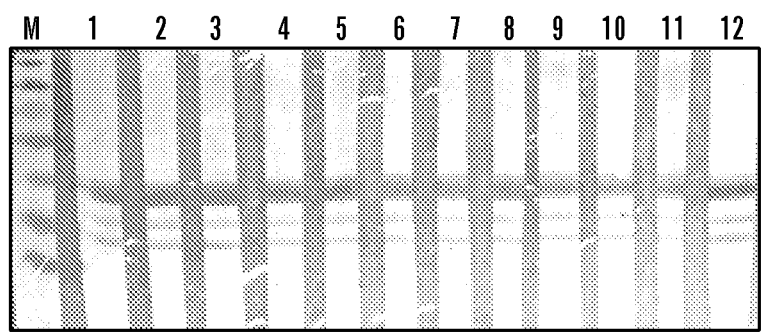
Figure 9A:
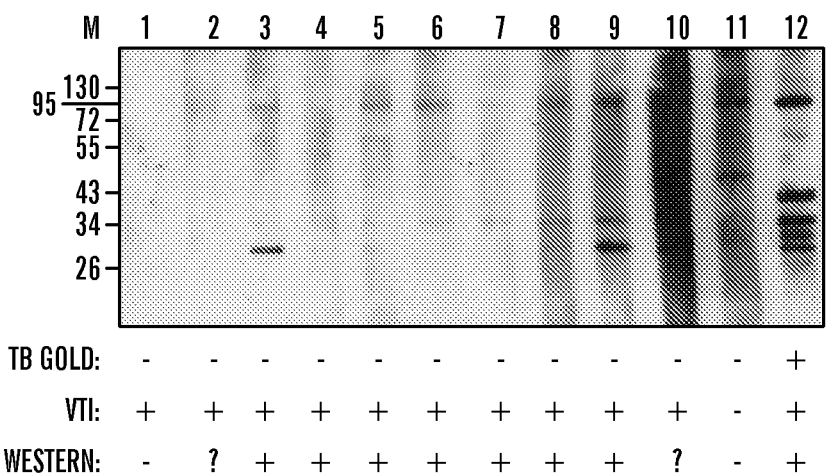
FIG. 9A-9B show Western blot analysis using GMP TB1 (CFP) and TB2 (ESAT) for samples 11 to 20 of the 20 cases shown in FIG. 7.
Figure 9B:
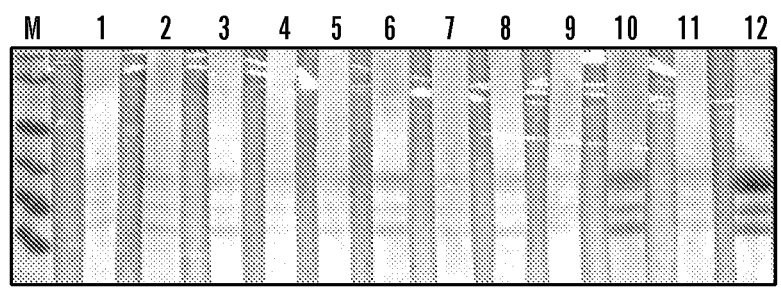
Figure 10:
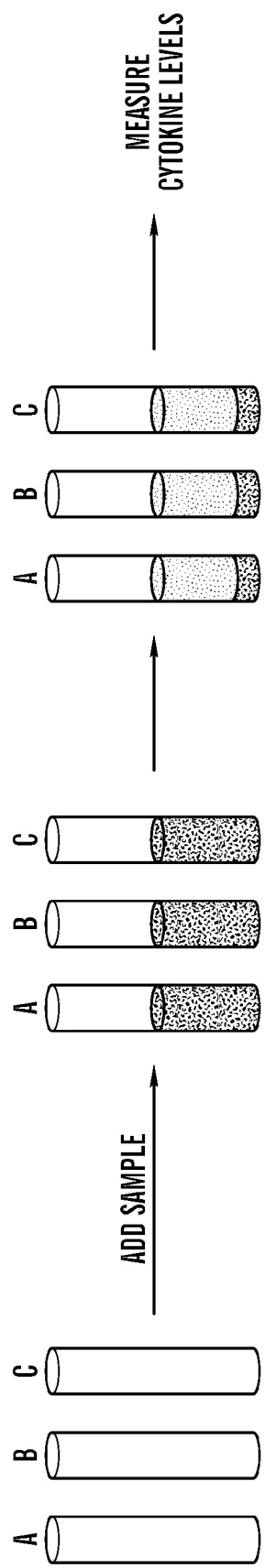
FIG. 10 is a schematic summarizing steps performed in the CMI assay, termed the "LF-CMI assay" works. A biological sample is placed in a container comprising a LFn-target antigen (A, B, C represent different LFn-target antigen polypeptides) and incubated for a sufficient period of time to induce a CMI response of the cells in the biological sample, and then the levels of cytokines are analysed.

The present invention provides an assay to detect and monitor cell-mediated immune responses of a subject, using an in vitro or ex vivo approach.

Current available laboratory assays to detect CMI responses have serious shortcomings, especially when applied to large vaccine efficacy trials in clinical settings. Such shortcomings include cost and difficulty in producing reagents for peptide-based CMI assays, as well as requirements for specialized equipment and technical support. Existing methods for detecting CMI responses have limitations, such as being only effective at detecting an immune responses to a small region of a target antigen, i.e. a CMI response can only be detected to the peptide used in the assay. Existing methods are generally limited to detecting a CMI response to a target antigen peptide, due to difficulty encountered in getting a target antigen larger than a peptide into a cell. That is, current CMI assays are generally not capable of detecting a CMI response to a target antigen polypeptide which is larger than a peptide.

The present invention is based at least in part on the discovery that a portion of an LF polypeptide, such as an LFn polypeptide or a fragment thereof can deliver a fused target antigen polypeptide, such as an entire full length or non-peptide target antigen protein into the cytosol of a cell. Accordingly, the present invention provides a method of measuring a cell mediated immune (CMI) response using an intact, living cell, by exposing the cell to a target antigen which is bound to an LF polypeptide such as an LFn polypeptide, where the LF polypeptide delivers the antigen to the cytosol of the cell. Where the cell has been previously sensitized to the target antigen, the cell will release cytokine(s) indicative of such prior sensitization or exposure. As such, described herein are methods to measure a CMI response of living, intact cells to a target antigen, and/or to detect a pathology of interest in a subject by delivering entire full length antigen or non-peptide portions thereof.

Accordingly and as discussed in more detail below, the methods described herein provide advantages over existing methods to determine CMI responses. For example, the methods described herein permit a more rapid, reliable and accurate detection of a CMI response, in intact cells, to a target antigen that is not limited to a peptide of a larger target antigen. More specifically and without wishing to be bound by theory, currently available laboratory assays that detect CMI responses have various shortcomings. Such assays include, for example, lymphocyte proliferation assays, skin tests to measure immediate and delayed hypersensitivity, and tests which require purification of cells for use in the assay (e.g., purification of lympocytes or PMBC from whole blood samples prior to stimulation with the antigen). Shortcomings include, for example, fairly stringent limitations on the size of an antigen which is able to get into the cytosol of a cell, and the need to lyse cells in order to detect a CMI response. Existing assays tend to be broadly (or generically) diagnostic in determining exposure to a pathogen, rather than being specific to variants of a target antigen. Typically, current CMI assays expose a cell, once it is purified, to a peptide of a target antigen which is small enough to enter the cytosol of the cell. As a result, such CMI assays are limited to detecting a CMI response only to that peptide. The present invention overcomes this limitation by providing a method to detect a CMI response to a large (and therefore non-peptide) target polypeptide antigen or a full length polypeptide antigen. Typically an ELISA or ELISPOT is used to detect the number of T-cells which produce a response to antigenic stimulation, but are not accurate or specific enough to provide specificity regarding to which variant the antigen belongs.

Previously used CMI assays which use peptides of a target antigen can also frequently result in inaccurate and unreliable or inconsistent results, such as a false negatives by overestimating diagnostic accuracy. By way of an example, a CMI assay which uses a peptide of a target antigen may not demonstrate a CMI response to the particular peptide used because the immune cell may not recognize the particular peptide used despite the subject having been previously exposed to the entire target antigen. This scenario would be considered a false negative. Conversely, in a second scenario, a different peptide from the same target antigen may result in eliciting or detecting a CMI response if the immune cell when previously exposed to the entire target antigen raised a response to that portion of the target antigen which is the same as the particular peptide used. Accordingly, a CMI assay which uses a peptide of a target antigen can render opposite results in eliciting or detecting a CMI response to a target antigen, i.e. a positive and a negative CMI response, where one peptide of the target antigen is recognized and another peptide to the target antigen is not recognized by the immune cell, respectively. The methods described herein address one, some or even all of such shortcomings, depending upon the exact embodiment(s) employed to measure a CMI response.

One aspect of the present invention provides a method for measuring immune cell responses, such as T cell responses to a target antigen, such as a target antigen from a pathogen. Such an embodiment is useful in the development of all T cell dependent vaccines or immune therapies. This strategy is applicable to other field of research where CMI responses play an important role in prevention and controlling of the diseases.

One aspect of the present invention relates to a method of measuring a cell mediated immune response to a target antigen in an intact cell comprising incubating a biological sample comprising intact cells with a portion of an LF polypeptide, such as an LFn polypeptide or a fragment thereof, fused to a target antigen. In some embodiments, the target antigen is expressed by a pathogen, for example where the pathogen is a virus, a target antigen can be a polypeptide expressed on the surface of the virus, such as a coat protein, or a polypeptide internal to the virus. Target antigens of particular relevance to the methods and compositions described herein include those expressed by an intracellular pathogen. One such pathogen target antigen which can be used in the methods as disclosed herein is TB1 (CFP) or TB2 (ESAT), or fragments thereof.

In a particular embodiment, a method of measuring a cell mediated immune response to a target antigen comprises incubating a biological sample comprising intact (i.e. living) cells with a panel of LFn-fusion polypeptides. In such an embodiment, a panel of LFn-fusion polypeptides can comprise LFn polypeptides fused to a variety of different sub-portions or fragments of a target antigen, and collectively and cumulatively, the target antigen fragment portion of LFn-fusion polypeptides substantially cover the entire length of a target antigen polypeptide. The detection of a CMI response to a sub-portion or fragment of a target antigen fused to an LFn polypeptide has numerous advantages. For example, it enables a more qualitative diagnosis of the CMI response, as instead of being able to detect a CMI response to an entire whole target antigen, using a panel of fragments enables one to home in on particular strains and/or variants of the target pathogen. By way of an illustrative example only, using HIV as an exemplary pathogen and gag as an exemplary target antigen, one can use the methods as disclosed herein to generically detect a CMI response using an LFn polypeptide fused to the whole gag polypeptide target antigen. If a CMI response is detected, one can subsequently determine which HIV variant gives rise to the CMI response by assessing the CMI response using a panel of LFn fusion polypeptides comprising different portions of the gag polypeptide, e.g., particular fragments of the gag protein specific to different variants or strains of HIV, to thereby determine which strain, variant or subtype of HIV (i.e. HIV1, HIV2 etc.) is involved. Accordingly, the methods as disclosed herein permit a more accurate and more qualitative measurement of CMI responses to a target antigen, with a level of clarity to permit differences in pathogenic strains, variants and subtypes to be quickly and easily distinguished.

In addition, the measurement of CMI response to a panel of LF-polypeptides, e.g., a panel of LFn-fusion polypeptides as disclosed herein, can be used to add another level of clarity and accuracy of the CMI response, for example to screen for false positives or inaccurate CMI responses. For example, if a positive CMI response is detected to a whole full length target antigen fused to an LFn polypeptide, one can check if the CMI response is a true positive or a false positive by determining the CMI response to a panel of LFn-fusion polypeptides which comprise a variety of fragments of a target antigen which collectively span substantially the entire region of the target antigen. If all of the LFn-fusion polypeptides of the panel of LFn-fusion polypeptides result in a positive CMI reaction, it is likely that the positive CMI reaction to the whole full length target antigen fused to an LFn polypeptide was a false positive, on the theory that an immune response is not generally raised to every portion of the target antigen. However, if only some, for example approximately about at least about 10%, or at least about 20%, or at least about 30%, or at least about 40%, or more than 40% but less than 100% of the panel of LFn-fusion polypeptides result in a positive CMI reaction, it is likely that a positive CMI reaction to the whole full length target antigen fused to an LFn polypeptide is a true positive, based upon the same theory that an immune response is not generally raised to every portion of a target antigen.

Stated another way and using TB1 as an illustrative example, if a CMI response is detected to an LFn fusion polypeptide comprising the TB1 antigen such as SEQ ID NO: 7 as disclosed herein, one can determine if this TB1 whole antigen-induced CMI response is a true positive (and thus eliminate it as a false positive) by detecting the CMI response to a panel of LFn-fusion polypeptides which comprise portions of the TB1. For example, such a panel of LFn-fusion polypeptides can comprise a variety of fragments of the TB1 target antigen which collectively span substantially the entire region of the TB1 target antigen. An example of such a panel of LFn-fusion polypeptide which span TB1 can comprise fragments of TB1, such as SEQ ID NO: 30 to SEQ ID NO: 46 as disclosed herein, fused to an LFn polypeptide or fragment thereof to create a panel of 17 TB1 fragment LFn-fusion polypeptides. If all 17 of the TB1 fragment LFn-fusion polypeptides of the panel result in a positive CMI reaction, it is likely that the positive CMI reaction to the full length TB 1 target antigen of SEQ ID NO: 7 fused to an LFn polypeptide is a false positive. However, if only some of the panel of TB1 fragment LFn-fusion polypeptides result in a positive CMI reaction, for example 2, or 3, or 4 or 5, or 6, or 7 or 8, or as many as 15 of the panel of 17 TB1 fragment LFn-fusion polypeptides, it is likely that positive CMI reaction to the full length TB1 target antigen of SEQ ID NO: 7 fused to LFn polypeptide is a true positive. A panel of fusion polypeptides which substantially cover the entire length of a target antigen can be at least two different polypeptides, up to any number of different LF polypeptide-fusion polypeptides, for example, at least two different polypeptides, or between 2-5, or between 5-10, or between 11-15 or 16-20 or more different LFn-fusion polypeptides.

Furthermore, the present invention is useful as a high throughput method for epitope mapping. For example, by measuring a CMI response to a panel of LFn-fusion polypeptides which comprise a variety of different sub-portions or fragments of a target antigen, one can identify which sub-portions or fragments of the target antigen result in a strong CMI response and thus map the epitope(s) of the target antigen responsible for eliciting strong CMI responses. Such epitope mapping is useful to identify regions of a target antigen for vaccine development or their use in highly specific and accurate diagnostic CMI assays to the target antigen.

The methods described herein can also be adapted for the diagnosis and/or monitoring of diseases or disorders involving inappropriate or inadequate immune function. For example, the methods described herein can be used for monitoring or diagnosis of autoimmune disease, by using a self antigen as the target antigen that is fused to an LF polypeptide. Detection of a CMI response to such a target antigen indicates that the subject has raised or is maintaining a cell mediated immune response to a self antigen. This type of assay benefits from not being reliant upon knowledge of the specific epitope against which a response will be raised. Similar approaches can be taken for diagnosis or monitoring of inflammatory diseases. The methods can also be adapted for predicting whether a given individual would be a candidate for a therapeutic vaccine, e.g., a cancer therapeutic vaccine designed to provoke an immune response against tumor cells.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "adjuvant" as used herein refers to any agent or entity which increases the antigenic response by a cell to a target antigen.

The terms "protective antigen" or "PA" are used interchangeably herein to refer to part of the B. anthracis exotoxin bipartite protein which binds to a mammalian cell's surface by cellular receptors. A "PA," as the term has its receptor binding site intact and functional. U.S. Pat. Nos. 5,591,631 and 5,677,274 (incorporated by reference in their entirety) describe PA fusion proteins that target PA to particular cells, such as cancer cells and HIV-infected cells, using as fusion partners ligands for receptors on the targeted cells.

The term "lethal factor" or "LF" as used herein refers generally to a non-PA polypeptide of the bipartite B. anthracis exotoxin. Wild-type, intact B. anthracis LF polypeptide has the amino acid sequence set out in GenBank Accession Number M29081 (Gene ID No: 143143), which corresponds to SEQ ID NO: 1. SEQ ID NO: 1 corresponds to LF with a signal peptide located at residues 1 to 33 at its N-terminus. Stated another way, immature wild-type LF corresponds to an 809 amino acid protein, which includes a 33 amino acid signal peptide at the N-terminus. The amino acid sequence of immature wild-type LF (SEQ ID NO: 1) with the signal peptide highlighted in bold is as follows:

(SEQ ID NO: 1)

MNIKKEFIKVISMSCLVTAITLSGPVFIPLVQGAGGHGDVGMHVKEKEKNKDENKRKDEERNKTQE

EHLKEIMKHIVKIEVKGEEAVKKEAAEKLLEKVPSDVLEMYKAIGGKIYIVDGDITKHISLEALSEDKKK

IKDIYGKDALLHEHYVYAKEGYEPVLVIQSSEDYVENTEKALNVYYEIGKILSRDILSKINQPYQKFLDV

LNTIKNASDSDGQDLLFTNQLKEHPTDFSVEFLEQNSNEVQEVFAKAFAYYIEPQHRDVLQLYAPEAFN

YMDKFNEQEINLSLEELKDQRMLSRYEKWEKIKQHYQHWSDSLSEEGRGLLKKLQIPIEPKKDDIIHSL

SQEEKELLKRIQIDSSDFLSTEEKEFLKKLQIDIRDSLSEEEKELLNRIQVDSSNPLSEKEKEFLKKLKLDI

QPYDINQRLQDTGGLIDSPSINLDVRKQYKRDIQNIDALLHQSIGSTLYNKIYLYENMNINNLTATLGAD

LVDSTDNTKINRGIFNEFKKNFKYSISSNYMIVDINERPALDNERLKWRIQLSPDTRAGYLENGKLILQR

NIGLEIKDVQIIKQSEKEYIRIDAKVVPKSKIDTKIQEAQLNINQEWNKALGLPKYTKLITFNVHNRYASN

IVESAYLILNEWKNNIQSDLIKKVTNYLVDGNGRFVFTDITLPNIAEQYTHQDEIYEQVHSKGLYVPESR

SILLHGPSKGVELRNDSEGFIHEFGHAVDDYAGYLLDKNQSDLVTNSKKFIDIFKEEGSNLTSYGRTNEA

EFFAEAFRLMHSTDHAERLKVQKNAPKTFQFINDQIKFIINS

Cleavage of the immature LF protein results in a mature wild-type LF polypeptide of 776 amino acids in length. The 776 amino acid polypeptide sequence of mature wild-type LF polypeptide (i.e. lacking the N-terminal signal peptide) corresponds to SEQ ID NO: 2, as follows:

(SEQ ID NO: 2)

AGGHGDVGMHVKEKEKNKDENKRKDEERNKTQEEHLKEIMKHIVKIEVKGEEAVKKEAAEKLLEKV

PSDVLEMYKAIGGKIYIVDGDITKHISLEALSEDKKKIKDIYGKDALLHEHYVYAKEGYEPVLVIQSSED

YVENTEKALNVYYEIGKILSRDILSKINQPYQKFLDVLNTIKNASDSDGQDLLFTNQLKEHPTDFSVEFL

EQNSNEVQEVFAKAFAYYIEPQHRDVLQLYAPEAFNYMDKFNEQEINLSLEELKDQRMLSRYEKWEKI

KQHYQHWSDSLSEEGRGLLKKLQIPIEPKKDDIIHSLSQEEKELLKRIQIDSSDFLSTEEKEFLKKLQIDIR

-continued

```
DSLSEEEKELLNRIQVDSSNPLSEKEKEFLKKLKLDIQPYDINQRLQDTGGLIDSPSINLDVRKQYKRDIQ

NIDALLHQSIGSTLYNKIYLYENMNINNLTATLGADLVDSTDNTKINRGIFNEFKKNFKYSISSNYMIVDI

NERPALDNERLKWRIQLSPDTRAGYLENGKLILQRNIGLEIKDVQIIKQSEKEYIRIDAKVVPKSKIDTKI

QEAQLNINQEWNKALGLPKYTKLITFNVHNRYASNIVESAYLILNEWKNNIQSDLIKKVTNYLVDGNG

RFVFTDITLPNIAEQYTHQDEIYEQVHSKGLYVPESRSILLHGPSKGVELRNDSEGFIHEFGHAVDDYAG

YLLDKNQSDLVTNSKKFIDIFKEEGSNLTSYGRTNEAEFFAEAFRLMHSTDHAERLKVQKNAPKTFQFI

NDQIKFIINS
```

The term "LF polypeptide" applies not only to full length, wild-type LF (with or without the signal sequence), but also to fragments thereof that mediate intracellular delivery of fused or physically associated polypeptides to a cell. Also included in the term "LF polypeptide" are conservative substitution variants of LF, including conservative substitution variants that mediate such intracellular delivery.

The term "substitution" when referring to a peptide, refers to a change in an amino acid for a different amino-acid moiety. Substitutions can be conservative or non-conservative substitutions, as described further herein below.

The term "LFn polypeptide" refers to an N-terminal fragment of B. anthracis LF that does not display zinc metalloproteinase activity, does not inactivate mitogen-activated kinase activity, or both, yet does mediate intracellular or transmembrane delivery of fused polypeptides. Thus, LFn polypeptides are a subset of LF polypeptides. Each method and/or kit described herein is contemplated to use one or more LF polypeptides, physically associated, e.g., fused with, a target antigen. LFn polypeptides as defined and described herein are preferred. In one aspect, "LFn polypeptide" includes SEQ ID NO: 3, which corresponds to a 288 amino acid immature LFn protein; this LFn protein is "immature" in that it includes a signal peptide located at residues 1 to 33 of the N-terminus. Stated another way, immature LFn corresponds to a 288 amino acid protein, which includes a 33 amino acid signal peptide at the N-terminus. Signal peptide cleavage of the immature LFn protein of SEQ ID NO: 3 results in a mature LFn polypeptide of 255 amino acids in length. It should be emphasized that, for the purposes of the methods and compositions described herein, the LF and/or LFn polypeptides can either include or lack the signal peptide—that is, the presence or absence of the signal peptide is not expected to influence the activity of LF polypeptides as transmembrane transport facilitators in the methods described herein. The amino acid sequence of immature LFn (SEQ ID NO: 3) with the signal peptide highlighted in bold is as follows:

```
                                                         (SEQ ID NO: 3)
MNIKKEFIKVISMSCLVTAITLSGPVFIPLVQGAGGHGDVGMHVKEKEKNKDENKRKDEERNKTQE

EHLKEIMKHIVKIEVKGEEAVKKEAAEKLLEKVPSDVLEMYKAIGGKIYIVDGDITKHISLEALSEDKKK

IKDIYGKDALLHEHYVYAKEGYEPVLVIQSSEDYVENTEKALNVYYEIGKILSRDILSKINQPYQKFLDV

LNTIKNASDSDGQDLLFTNQLKEHPTDFSVEFLEQNSNEVQEVFAKAFAYYIEPQHRDVLQLYAPEAFN

YMDKFNEQEINLS
```

The polypeptide sequence of a mature LFn polypeptide (which lacks the N-terminal signal peptide) is 255 amino acids in length and corresponds to SEQ ID NO: 4 is as follows:

```
                                                         (SEQ ID NO: 4)
AGGHGDVGMHVKEKEKNKDENKRKDEERNKTQEEHLKEIMKHIVKIEVKGEEAVKKEAAEKLLEKV

PSDVLEMYKAIGGKIYIVDGDITKHISLEALSEDKKKIKDIYGKDALLHEHYVYAKEGYEPVLVIQSSED

YVENTEKALNVYYEIGKILSRDILSKINQPYQKFLDVLNTIKNASDSDGQDLLFTNQLKEHPTDFSVEFL

EQNSNEVQEVFAKAFAYYIEPQHRDVLQLYAPEAFNYMDKFNEQEINLS
```

The term "functional fragment" as used in the context of a "functional fragment of LFn" refers to a fragment of an LFn polypeptide that mediates, effects or facilitates transport of an antigen across an intact, alive cell's membrane. One example of such a fragment of an LFn polypeptide is a 104 amino acid C-terminal fragment of LFn corresponding to SEQ ID NO: 5 as follows (this sequence is also disclosed as SEQ ID NO: 3 in U.S. patent application Ser. No. 10/473190, which is incorporated herein by reference):

```
                                                         (SEQ ID NO: 5)
GKILSRDILSKINQPYQKFLDVLNTIKNASDSDGQDLLFTNQLKEHPTDFSVEFLEQNSNEVQEVFAKAF

AYYIEPQHRDVLQLYAPEAFNYMDKFNEQEINLS
```

The term "LFn polypeptide" as used herein encompasses each of the "immature" LFn and "mature" LFn molecules described herein, as well as fragments, variants (including conservative substitution variants) and derivatives thereof that mediate, effect or facilitate transport of a physically associated, e.g., fused, polypeptide across the membrane of an intact, living cell. Additional fragments of LFn polypeptides specifically contemplated for use in the methods, compositions and kits described herein include a fragment comprising, or optionally, consisting essentially of the C-terminal 60, 80, 90, 100 or 104 amino acids of SEQ ID NO: 3 or a conservative substitution variant thereof that mediates, effects or facilitates transfer of a physically associated, e.g., fused polypeptide across an intact membrane of a living cell.

A "fragment" of a target antigen as that term is used herein will be at least 15 amino acids in length, and can be, for example, at least 16, at least 17, at least 18, at least 19, at least 20 or at least 25 amino acids or greater. Thus, in instances where, for example, a panel of target antigen fragment-LF polypeptides are prepared, the target antigen fragments will be at least 15 amino acids in length.

The terms "Cytotoxic T Lymphocyte" or "CTL" refers to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells.

The term "cell mediated immunity" or "CMI" as used herein refers to an immune response that does not involve antibodies or complement but rather involves the activation of macrophages, natural killer cells (NK), antigen-specific cytotoxic T-lymphocytes (T-cells), and the release of various cytokines in response to a target antigen. Stated another way, CMI refers to immune cells (such as T cells and lymphocytes) which bind to the surface of other cells that display the antigen (such as antigen presenting cells (APS)) and trigger a response. The response may involve either other lymphocytes and/or any of the other white blood cells (leukocytes) and the release of cytokines. Accordingly, cell-mediated immunity (CMI) is an immune response that does not involve antibodies but rather involves the activation of macrophages and NK-cells, the production of antigen-specific cytotoxic T-lymphocytes, and the release of various cytokines in response to an antigen. Cellular immunity protects the body by: (i) activating antigen-specific cytotoxic T-lymphocytes (CTLs) that are able to destroy body cells displaying epitopes of foreign antigen on their surface, such as virus-infected cells, cells with intracellular bacteria, and cancer cells displaying tumor antigens; (2)activating macrophages and NK cells, enabling them to destroy intracellular pathogens; and (3) stimulating cells to secrete a variety of cytokines that influence the function of other cells involved in adaptive immune responses and innate immune responses. Without wishing to be bound by theory and by way of background, the immune system was separated into two branches: humoral immunity, for which the protective function of immunization could be found in the humor (cell-free bodily fluid or serum) and cellular immunity, for which the protective function of immunization was associated with cells.

The term "immune cell" as used herein refers to any cell which can release a cytokine in response to a direct or indirect antigenic stimulation. Included in the term "immune cells" herein are lympocytes, including natural killer (NK) cells, T-cells (CD4+ and/or CD8+ cells), B-cells, macrophages and monocytes, Th cells; Th1 cells; Th2 cells; Tc cells; stromal cells; endothelial cells; leukocytes; dendritic cells; macrophages; mast cells and monocytes and any other cell which is capable of producing a cytokine molecule in response to direct or indirect antigen stimulation. Typically, an immune cell is a lymphocyte, for example a T-cell lymphocyte.

The term "cytokine" as used herein is used interchangeably with the term "effector molecule," and refers to a molecule released from an immune cell in response to stimulation with an antigen. Examples of such cytokines include, but are not limited to; GM-CSF; IL-1$\alpha$; IL-1$\beta$; IL-2; IL-3; IL-4; IL-5; IL-6; IL-7; IL-8; IL-10; IL-12; IFN-$\alpha$; IFN-$\beta$; IFN-$\gamma$; MIP-1$\alpha$; MIP-1$\beta$; TGF-$\beta$; TNF$\alpha$ and TNF$\beta$.

The term "complex" as used herein refers to a collection of two or more molecules, whereby they are connected spatially by means other than a covalent interaction; for example they can be connected by electrostatic interactions such as van der Waals forces etc.

The term "fusion protein" as used herein refers to a recombinant protein of two or more proteins which are joined by a peptide bond. Fusion proteins can be produced, for example, by a nucleic acid sequence encoding one protein joined to the nucleic acid encoding another protein such that they constitute a single open-reading frame that can be translated into a single polypeptide harboring all the intended proteins.

The term "translocated into a cell" refers to the movement of a moiety, such as the target antigen, and optionally an LFn polypeptide, an LFn homologue or mimetic, or variant thereof from a location outside the cell, across the plasma membrane to the inside of an intact, living cell.

The term "transduction" refers to any method whereby a nucleic acid is introduced into a cell, e.g., by transfection, lipofection, electroporation, biolistics, passive uptake, lipid: nucleic acid complexes, viral vector transduction, injection, contacting with naked DNA, and the like.

The term "in vivo" refers to assays or processes that occur in an animal.

The term "ex vivo" refers to assays that are performed using a living cell with an intact membrane that is outside of the body, e.g., explants, cultured cells, including primary cells and cell lines, transformed cell lines, and extracted tissue or cells, including blood cells, among others.

The assays described herein can also be characterized as "in vitro" assays in that they are performed in containers outside the body of a subject. It should be understood that where the term "in vitro" is or might be applied to assays described herein, the CMI assays require intact, living cells, including living immune cells. Samples also need cells capable of processing and displaying target antigen. While the CMI assays themselves require intact, living cells, it should be understood that once such cells have been contacted with an LF polypeptide-target antigen fusion or complex, the type and amount of cytokines released by those cells can be measured by in vitro approaches that do not necessarily require intact cells.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In some embodiments, a mammal is a human.

The term "subject" as used herein refers to any animal in which it is useful to diagnose a CMI response, for example to diagnose if the subject has a disease or condition, or is likely to develop a disease or condition. The subject can be a mammal, for example a human, or can be a wild, domestic, commercial or companion animal. While in one embodiment of the invention it is contemplated that the CMI assays are suitable for the diagnostic use in humans, it is also applicable to all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is a wild animal, for example a bird such as for the diagnosis of avian flu. In some embodiments, the subject is an experimental animal or animal substitute as a disease model. The subject may be a subject in need of veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates, or livestock animals such as pigs, cattle and sheep, where the detection of a CMI response to a pathogen is useful to prevent a disease and/or to control the spread of a disease, for example SIV, STL1, SFV, or in the case of live-stock, hoof and mouth disease and other such diseases.

The term "biological sample" refers to a sample of biological tissue, cells, or fluid that, in a healthy and/or pathological state, contains immune cells as they are described herein and cells capable of processing and displaying an intracellular polypeptide antigen. Such samples include, but are not limited to, whole blood, cultured cells, primary cell preparations, sputum, amniotic fluid, tissue or fine needle biopsy samples, peritoneal fluid, and pleural fluid, among others. In some embodiments a biological sample is taken from a human patient, and in alternative embodiments the biological sample is taken from any mammal, such as rodents, animal models of diseases, commercial animals, companion animals, dogs, cats, sheep, cattle, and pigs, etc. The biological sample can be pretreated as necessary for storage or preservation, by dilution in an appropriate buffer solution or concentrated, if desired. However, the sample must contain living cells. Any of a number of standard aqueous buffer solutions, employing one of a variety of buffers, such as phosphate, Tris, or the like, at physiological pH can be used. The biological sample can in certain circumstances be stored for use prior to use in the assay as disclosed herein. Such storage can be at +4 C or frozen, for example at −20 C or −80 C, provided suitable cryopreservation agents are used to maintain cell viability once the cells are thawed.

The term "tissue" refers to a group or layer of similarly specialized cells, which together perform certain special functions. The term "tissue-specific" refers to a source of cells from a specific tissue. The term "tissue" is intended to include, blood, blood preparations such as plasma and serum, bones, joints, muscles, smooth muscles, and organs.

As used herein, the term "pathogen" refers to an organism or molecule that causes a disease or disorder in a subject. For example, pathogens include but are not limited to viruses, fungi, bacteria, parasites and other infectious organisms or molecules therefrom, as well as taxonomically related macroscopic organisms within the categories algae, fungi, yeast and protozoa or the like.

A "cancer cell" refers to a cancerous, pre-cancerous or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice (see also Freshney, Culture of Animal Cells: A Manual of Basic Technique (3rd ed. 1994)).

The term "wild type" refers to the naturally-occurring, normal polynucleotide sequence encoding a protein, or a portion thereof, or protein sequence, or portion thereof, respectively, as it normally exists in vivo. Accordingly, as disclosed herein, the wild type amino acid sequence for LFn protein corresponds to SEQ ID NO: 3 (with signal peptide) and/or SEQ ID NO: 4 (without signal peptide), which correspond to an N-terminal fragment of the Lethal Factor (LF).

The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The terms "polypeptide" and "protein" are used interchangeably to refer to a polymer of amino acid residues linked by peptide bonds, and for the purposes of the claimed invention, have a minimum length of at least 15 amino acids. Oligopeptides, oligomers multimers, and the like, typically refer to longer chains of amino acids and are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. For the methods, kits and compositions described herein, the term "peptide" refers to a sequence of peptide-linked amino acids containing at least two and less than 15 amino acids in length.

It will be appreciated that a protein or polypeptide often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in peptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The terms "homology", "identity" and "similarity" refer to the degree of sequence similarity between two polypeptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" shares less than 40% identity, though preferably less than 25% identity with the sequences as disclosed herein.

As used herein, the terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. That is, a polypeptide that performs the same function as a given polypeptide in another species can be viewed as a homolog of that given polypeptide. Determination of homologs of genes or polypeptides can be easily ascertained by the skilled artisan.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Where necessary or desired, optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=-4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G, U or I) or amino acid residue occurs in both sequences to yield the number of matched positions, dividing the number of matched positions by the total number of positions in the comparison window (i.e., the window size), and multiplying the result by 100 to yield the percentage of sequence identity.

The term "variant" as used herein refers to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild- type polynucleotide or polypeptide). A "variant" of an LFn polypeptide refers to a molecule substantially similar in structure and function to that of a polypeptide of SEQ ID NO: 3, where the function is the ability to mediate, effect or facilitate transport of an associated or fused polypeptide across a cell membrane of a living cell from a subject. In some embodiments, a variant of SEQ ID NO: 3 or SEQ ID NO: 4 is a fragment of SEQ ID NO: 3 or 4 as disclosed herein, such as SEQ ID NO: 5.

A molecule is said to be "substantially similar" to another molecule if both molecules have substantially similar structures (i.e., they are at least 50% similar in amino acid sequence as determined by BLASTp alignment set at default parameters) and are substantially similar in at least one relevant function (here, for example, at least 50% as active in mediating, effecting or facilitating transport of an associated or fused polypeptide across the membrane of an intact, living cell). Transmembrane transport can be measured by methods known in the art. To avoid any confusion, a preferred method is that described by Kushner et. al., 2003, Proc. Natl. Acad. Sci. U S A. 100: 6652-6657.

The term "substantially similar," when used in reference to a variant of LFn or a functional derivative of LFn as compared to the LFn protein encoded by SEQ ID NO: 3 means that a particular subject sequence, for example, an LFn fragment or LFn variant or LFn derivative sequence, varies from the sequence of the LFn polypeptide encoded by SEQ ID NO: 3 by one or more substitutions, deletions, or additions relative to SEQ ID NO: 3, but retains at least 50% of the transmembrane transport facilitation activity, and preferably higher, e.g., at least 60%, 70%, 80%, 90% or more exhibited by the LFn protein of SEQ ID NO: 3. (It is acknowledged that LFn does not occur naturally—reference to a "native" or "natural" LFn sequence is intended to convey that the sequence is identical to the portion of naturally-occurring LF polypeptide designated as LFn herein.) In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given LFn nucleic acid sequence if: (a) the nucleotide sequence is hybridizes to the coding regions of the native LFn sequence, or (b) the nucleotide sequence is capable of hybridization to nucleotide sequence of LFn encoded by SEQ ID NO: 1 under moderately stringent conditions and has biological activity similar to the native LFn protein; or (c) the nucleotide sequences are degenerate as a result of the genetic code relative to the nucleotide sequences defined in (a) or (b). Substantially similar proteins will typically be greater than about 80% similar to the corresponding sequence of the native protein.

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another having similar structural and/or chemical properties. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).)

The choice of conservative amino acids may be selected based on the location of the amino acid to be substituted in the peptide, for example if the amino acid is on the exterior of the peptide and exposed to solvents, or on the interior and not exposed to solvents. Selection of such conservative amino acid substitutions is within the skill of one of ordinary skill in the art and is described, for example by Dordo et al., J. Mol Biol, 1999, 217, 721-739 and Taylor et al., J. Theor. Biol. 119(1986);205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent). These substitutions include, but are not limited to the following: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions suitable for amino acids on the interior of a protein or peptide. For example, one can use suitable conservative substitutions for amino acids in the interior of a protein or peptide (i.e. the amino acids are not exposed to a solvent). For example, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, LF polypeptides including non-conservative amino acid substitutions are also encompassed within the term "variants." A variant of an LFn polypeptide, for example a variant of SEQ ID NO: 3 or 4 is meant to refer to any molecule substantially similar in structure (i.e., having at least 50% homology as determined by BLASTp analysis using default parameters) and function (i.e., at least 50% as effective as a polypeptide of SEQ ID NO: 3 in transmembrane transport) to a molecule of SEQ ID NO: 3 or 4.

As used herein, the term "non-conservative" refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R).

The term "derivative" as used herein refers to peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to a protein molecule which possess a biological activity that is substantially similar to a biological activity of the entity or molecule of which it is a derivative or variant. By "substantially similar" in this context is meant that the biological activity, e.g., transmembrane transport of associated polypeptides is at least 50% as active as a reference, e.g., a corresponding wild-type polypeptide, and preferably at least 60% as active, 70% as active, 80% as active, 90% as active, 95% as active, 100% as active or even higher (i.e., the variant or derivative has greater activity than the wild-type), e.g., 110% as active, 120% as active, or more.

"Insertions" or "deletions," as the terms are used herein, are typically in the range of about 1 to 5 amino acids. The variation permitted in view of maintaining function can be experimentally determined by producing the peptide synthetically while systematically making insertions, deletions, or substitutions of nucleotides in the sequence using recombinant DNA techniques.

The term "specifically binds" refers to binding with a $K_d$ of 10 micromolar or less, preferably 1 micromolar or less, more preferably 100 nM or less, 10 nM or less, or 1 nM or less.

By "substantially pure" is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally occurring organic molecules with which it is naturally associated. A substantially pure polypeptide may be obtained, for example, by extraction from a natural source, by expression of a recombinant nucleic acid in a cell that does not normally express that protein, or by chemical synthesis.

As used herein the term "reference level" refers to a cytokine level for a given cytokine which provides a baseline against which to measure a CMI response. As an illustrative example, the reference level for cytokine X can be calculated as the average level of the cytokine gene and/or protein expression for cytokine X from at least one negative control biological sample, e.g., a biological sample obtained from one or more subjects which have not been pre-exposed to a target antigen. Typically, a reference level is normalized to "0" value, and an increase in the cytokine level measured in a CMI assay as disclosed herein relative to the reference level would indicate a positive CMI response. A reference can be from an individual not affected by a given pathology, or, alternatively, from the same individual being tested, where such sample was taken at an earlier time. A reference can also be a pooled sample, taken from a plurality of individuals not affected by the pathology in question. Where appropriate, a reference can also be a fixed threshold level of a given cytokine, above which a pathological condition or the presence of a pathogen is indicated. It is preferred that a reference sample be from an individual or group of individuals of similar characteristics to the tested individual, e.g., that the reference be taken from individuals of similar age, gender, rave or ethnic background, etc. In some embodiments, other reference levels can also be used, for example a positive reference level can be used as a positive control for the CMI reaction. Typically, where a positive reference level is used, if the cytokine measured in the CMI assay as disclosed herein is substantially the same or close in the value of the positive reference level for the same cytokine, it would indicate a positive CMI response.

The term "reduced" or "reduce" or "decrease" as used herein generally means a decrease by a statistically significant amount relative to a reference. However, for avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e. absent level as compared to a reference sample), or any decrease between 10-100% as compared to a reference level, as that term is defined herein.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e. absent level as compared to a reference sample).

The terms "increased" or "increase" as used herein generally mean an increase by a statically significant amount; for the avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; for the avoidance of doubt, "high" means a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, at least 2-fold higher, at least 3-fold higher, at least 4-fold higher, at least 5-fold higher, at least 10-fold higher or more, as compared to a reference level.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked.

The articles "a" and "an" are used herein to refer to one or to more than one (i.e., to at least one) of the grammatical object of the article. By way of example, "an element" means one element or more than one element.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following, including the Examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Methods And Compositions To Assay For A Cmi Response

Described herein are methods and compositions for detecting a CMI response to an antigen. The response can indicate, for example, infection or other antigen exposure of the subject. The methods and compositions described herein are particularly well suited for the detection of intracellular pathogens. Also described are methods of monitoring the ability of an individual to mount a CMI response to a given target antigen. The approaches use a biological sample, obtained from an individual, which includes immune cells and cells capable of processing and displaying a target antigen delivered to their cytosol. Typically such a biological sample is obtained from a subject, and the sample is incubated with a target antigen-LF polypeptide fusion polypeptide, e.g., an LFn fusion polypeptide as described herein.

Without wishing to be bound by theory, upon incubation with a sample of cells from the individual, the LF polypeptide-target antigen complex (e.g., LFn polypeptide-target antigen fusion polypeptide) enters the cytosol of a cell in the sample, aided by the LF polypeptide, and is processed and displayed as antigen fragments on the surface of such cell, in association with MHC molecules. Pre-sensitized immune cells in the sample, e.g., CD4+ or CD8+ T cells specific for any of the displayed target antigen fragments will release one or more cytokines upon interaction of their specific T cell receptors with the displayed target antigen fragments. The detection of cytokine release by the immune cells thereby provides an indicator or read-out that the individual is infected with a pathogen expressing the target antigen or has been otherwise exposed to that target antigen.

In one embodiment, one can determine that there is a positive CMI response in the assays described herein by a differential expression method. Namely, one can use a comparison of cytokine level relative to the level shown in a reference sample. An increase in a given cytokine or members of a panel of cytokines, as the term "increase" is defined herein, relative to the reference is indicative of a positive response.

The identity and/or relative amounts of the cytokine(s) released can provide a further indication of the nature of the pathogen. That is, particular pathogens or conditions can result in cytokine release profiles that are characteristic for individuals infected with or otherwise exposed to those pathogens or suffering from those conditions (e.g., autoimmune disease).

The various components required to perform the methods described herein and considerations for various aspects of the methods and compositions are described in the following sections.

I. Lf Polypeptides

By way of background and without wishing to be limited by theory, lethal toxin (LF) is one of two bipartite protein exotoxins, lethal toxin (LT) and edema toxin (ET) from *B. anthracis*. LT is composed of protective antigen (PA) and lethal factor (LF), whereas edema toxin consists of PA and edema factor (EF). None of these three components, PA, LF, and EF, alone is toxic. Once combined however, edema toxin causes edema and LT causes death by systemic shock in animals and humans. Consistent with its critical role in forming both toxins, PA has been identified as the protective component in vaccines against anthrax. The molecular mechanism of anthrax toxin action is currently hypothesized as follows: PA is a 735-amino acid polypeptide that binds to the surface of mammalian cells by cellular receptors. Once bound, PA is activated by proteolytic cleavage by cellular proteases to a 63-kDa molecule capable of forming a ring-shaped heptamer in the plasma membrane of the targeted cell (FIG. 1) (Milne et al., (1994) J. Biol. Chem. 269, 20607-20612, Petosa, et al., (1997) Nature (London) 385, 833-838). The PA heptamer then binds either EF or LF, which are internalized by endocytosis. After endosomal acidification, PA enables EF or LF to enter the cytosol, presumably by means of a pore formed by the heptamer. Within the cytosol, EF acts as an adenylate cyclase (Leppla, S. H. (1982) Proc. Natl. Acad. Sci. USA 79, 3162-3166) to convert ATP to cAMP. Abnormally elevated levels of cAMP perturb cellular metabolism.

Anthrax lethal factor or LF is a protein that is naturally produced and has MAPKK protease activity. Deletion analysis of LF shows that the PA binding domain is located within the amino-terminus of LFn, and that mutational studies demonstrate that the PA binding domain is located with in the region of amino acids 34 to 254 of the LF polypeptide of SEQ ID NO: 1, and within the region of amino acids 34 to 288 of the LF polypeptide of SEQ ID NO: 2. (Arora et al., J. Biol. Chem. 268:3334 3341 (1993); Milne, et al., (1995) Mol. Microbiol. 15, 661-66).

The action of LF in the cytosol causes the death of host cells by a mechanism that is not well understood. LF induces over-production of a number of lymphokines (Klimpel, et al., (1994) Mol. Microbiol. 13, 1093-1100), contributing to lethal systemic shock in host animals. Recent studies also show that LF has two enzymatic activities: it can act as a zinc metalloprotease (Duesbery, et al., (1998) Science 280, 734-737), and it inactivates mitogen-activated protein kinase (Hanna, et al.,. (1994) Mol. Med. 1, 7-18). Although it is still not clear how these two enzymatic activities of LF are connected, both are required for LF toxicity. It has previously been reported that anthrax toxin B moieties may be used to deliver eptiopes which in turn elicit an antibody response by the immune system, in the presence of PA (WO 97/23236).

LF is a 796-aa polypeptide, and the functional domain for both enzymatic activities is located between amino acids 383 and 796 of SEQ ID NO: 1. The N-terminal truncated LF without this catalytic domain completely lacks any toxic effect when mixed with PA and added to cultured macrophages or when injected into animals. It does, however, still bind to PA effectively. The PA binding domain of LFn occurs within residues 34-288 of SEQ ID NO:2 (Milne, et al., (1995) Mol. Microbiol. 15, 661-66).

The 83 kDa PA polypeptide binds at its carboxyl-terminus to a cell surface receptor, where it is specifically cleaved by a protease, e.g., furin, clostripain, or trypsin. This enzymatic cleavage releases a 20 kDa amino-terminal PA fragment, while a 63 kDa carboxyl-terminal PA fragment remains bound to the cell surface receptor. The 63 kDa fragment is also referred to as "processed protective antigen." Processed PA contains both a cell surface receptor binding site at its carboxyl-terminus and a lethal factor binding site at its new amino-terminus (see, e.g., Singh et al., J. Biol. Chem. 264: 19103 19107 (1989)). Processed PA may be produced by enzymatic cleavage in vitro, ex vivo or in vivo, or as a recombinant protein. As used herein the term PA refers PA molecules that have the lethal factor binding site, e.g., recombinant PA, naturally occurring PA, functional equivalents of PA that contain the lethal factor binding site, and PA fusion proteins that contain the lethal factor binding site.

II. Compositions Comprising Lf Polypeptides And Target Antigen

The inventors have established that a fragment of the lethal factor (LF) can deliver a fused exogenous target antigens to the cytosol of an intact cell. In particular, the inventors have previously demonstrated that in the absence of PA, an antigen physically associated with or fused to LFn or a fragment thereof can be used to deliver an antigen to the cytosol of an intact, living cell and elicit a CTL response to the fused antigen.

The methods and kits described herein employ LF polypeptides to deliver a target antigen to the cytosol of a cell from a subject. The LF polypeptide compositions involved generally comprise an LF polypeptide and a target antigen, where the LF polypeptide, e.g., LFn, is fused with the target antigen. Alternatively, the LF polypeptide can be in a complex or associated with the target antigen in some way, for example, to form an LFn:target antigen complex. In some embodiments, the composition comprises an LF polypeptide: target antigen complex, where the LF polypeptide, e.g., LFn, is directly associated with the target antigen by van der Waals forces or other non-covalent interactions. In alternative embodiments, the composition comprises an LF polypeptide: target antigen complex, where the LF polypeptide, e.g., an LFn polypeptide is indirectly associated with the target antigen, for example by interaction of the LFn polypeptide with at least one third moiety, and the target antigen interacts with the same third moiety that interacts with the LFn polypeptide. Such interactions can be any non-covalent association known by a skilled artisan, including, but not limited to, van der Waals forces, hydrophilic interactions, hydrophobic interactions and other non-covalent interactions. In some embodiments, at least one, or at least two, or at least 3, or at least 4 or more third entities can be used to associate an LFn polypeptide with the target antigen. For example, the LF polypeptide-target antigen complexes can include compositions which comprise an LFn:moiety:target antigen complex, or Lfn:moiety:moiety:target antigen complex, Lfn:moiety:moiety:moiety:target antigen complex, and the like. In some embodiments, a moiety which associates with an LP polypeptide, e.g., LFn can be the same or different from a moiety which binds with the target antigen, and all the moieties can be the same within a complex, or different within the complex.

A. LFn

As discussed above, a "LFn polypeptide" includes a LF polypeptide fragment represented by SEQ ID NOs 3 and 4, as well as recombinant LFn, and functional LFn equivalents, fragments, and variants that retain the function to deliver an associated or fused polypeptide target antigen to the cytosol of an intact cell, preferably a living cell. The term "LFn polypeptide" therefore includes functional LFn homologues such as polymorphic variants, alleles, mutants, and closely related interspecies variants that have at least about 60% amino acid sequence identity to LFn and have the function to deliver a fused polypeptide target antigen to the cytosol of a cell, as determined using the assays described herein. In particular embodiments, the LFn polypeptides are substantially identical to LFn of SEQ ID NO: 3 and SEQ ID NO: 4 as disclosed herein. In some embodiments, some functional polymorphic variants, alleles, mutants, and closely related interspecies variants of LFn that function to deliver a polypeptide target antigen to an intact cell can be determined by the methods and assays as disclosed in U.S. patent application Ser. No. 10/473,190 which is incorporated herein by reference.

In some embodiments, an LFn mimetic is useful in the compositions and methods described herein. An "LFn mimetic" refers to a compound or molecule, e.g., a peptide, polypeptide, or small chemical molecule that functions as LFn to deliver a target antigen to the cytosol of a cell to induce a CMI response against the antigen. LFn mimetics thus include LFn homologues. LFn mimetics would also include small LFn peptides that retain the LFn function to deliver fused or associated polypeptide antigens to the cytosol of the cell, and conservatively substituted variants thereof, as well as truncated versions of LFn that retain ability of LFn to deliver fused or associated polypeptide antigens to the cytosol of a cell. LFn mimetics are tested using assays for a CMI response to the target antigen as disclosed herein and in the Examples of U.S. patent application Ser. No. 10/473,190 (which is incorporated herein in its entirety by reference), e.g., induction of a CTL response to the delivered target antigen. When testing for an LFn mimetic, LFn is typically used as a positive control for delivery of the target antigen to a cell.

The inventors have discovered that a fragment of LFn which is at least about 250 amino acids or less, or at least about 150 amino acids or less, or at least about 104 amino acids or less, is able to deliver the fused target antigen to the cell and is useful in the methods and compositions of the CMI response herein.

In some embodiments, an LFn polypeptide as described herein comprises a non-functional binding site for PA, and thus is a mutant of LFn which does not result in functional binding with PA. Such mutants include, but are not limited to mutants altered at one or more of the residues critical for interacting with PA, such as a mutation in one or more of the following residues: Y22; L188; D187; Y226; L235; H229 (see Lacy et al., JBC, 2002; 277; 3006-3010); D106A; Y108K; E135K; D136K; N140A and K143A (see Melnyk et al., JBC, 2006; 281; 1630-1635 and Cunningham et al., PNAS, 2002; 99; 70497052, which are incorporated herein in their entirety by reference).

B. Target Antigen

An antigen for use in the compositions and methods described herein can be any target antigen, including, but not limited to pathogenic peptides, toxins, toxoids, subunits thereof, or combinations thereof (e.g., cholera toxin, tetanus toxoid).

A target antigen which can be fused to a LF polypeptide or an LFn polypeptide can be any antigen associated with an infectious disease, or cancer or immune disease. In some embodiments, a target antigen fused to an LF polypeptide can be an antigen expressed by any of a variety of infectious agents, including a pathogen, virus, bacterium, fungus or parasite.

As discussed herein, an intact (i.e. an entire or whole) target antigen can be fused to an LF polypeptide. By "intact" in this context is meant that the target antigen is the full length target antigen as that antigen polypeptide occurs in nature. This is in direct contrast to delivery of only a small portion or peptide of the target antigen. By delivering an intact target antigen to a cell, the LF polypeptide enables or facilitates the detection of a CMI response to a full range of epitopes of the intact target antigen, rather than just a single or selected few peptide epitopes. Accordingly, the methods and compositions described herein provide assays to detect a CMI response which are more sensitive and have higher specificity as compared to use of a peptide-based target antigen, in that when a whole target antigen is used to assay a CMI response, a response that was raised against essentially any epitope of the whole antigen would be more likely to be detected.

In some embodiments, to avoid false positives associated with the increased sensitivity provided by the methods described herein, one can also divide the intact target antigen into fragments, or parts, of the whole target antigen, for example, at least two, or at least 3, or at least 4, or a least 5 or more target antigen fragments, depending on size of the intact target antigen protein. These fragments of the whole target antigen can be used as a quality control to filter out false positives of a positive CMI response to the whole target antigen fused to an LF polypeptide. By way of an example only, a positive CMI response to a whole target antigen fused to LFn can be confirmed by assessing a CMI response to a panel of target antigens fused to LFn which are fragments of the whole target antigen. A true CMI response is confirmed if one or two of the fragments give a positive response, but not all fragments. If a positive CMI response is detected for all fragments, it is likely that the positive CMI response to a whole target antigen fused to LFn was a false positive.

In some embodiments, an intact target antigen can be divided into many parts, depending on the size of the initial target antigen, for use as a panel of sub-target antigens. Typically, where a whole target antigen is a multimer polypeptide, the whole target protein can be divided into sub-units and/or domains which can each individually be fused to an LF polypeptide, e.g., an LFn polypeptide, to create a panel of LF polypeptide-fusion polypeptides of the target antigen which can be used in the assay methods and compositions as disclosed herein. Alternatively, an intact target antigen can be divided into fragments, or parts, of the whole target antigen, for example, at least two, or at least 3, or at least 4, or a least 5, or at least 6, or at least 7, or at least 8, or at least about 9, or at least about 10, or at least about 11, or at least about 12, or at least about 13, or at least about 15, or at least about 20, or at least about 25, or more than 25 fragments, and each fragment is individually fused to an LF polypeptide to create a panel of LF polypeptide-fusion polypeptides of the target antigen which can be used in the assay methods and compositions as disclosed herein.

The fragmentation or division of a full length target antigen polypeptide can be an equal division of the full length target antigen polypeptide, or alternatively, in some embodiments, the fragmentation is asymmetrical or unequal. As a non-limiting example, where a target antigen is divided into two overlapping fragments, a target antigen can be divided into fragments of approximately the same (equal) size, or alternatively one fragment can be about 45% of the whole target antigen and the other fragment can be about 65%. As further non-limiting examples, a whole target antigen can be divided into a combination of differently sized fragments, for example, where a target antigen is divided into two fragments, fragments can be divided into about 40% and about 70%, or about 45% and about 65%; or about 35% and about 75%; or about 25% and about 85% of the whole target antigen. Any combination of overlapping fragments of a full length whole target antigen is encompassed for use in the generation of a panel of overlapping LFn-fusion polypeptides of a target antigen. As an illustrative example only, where a target antigen is divided into 5 portions, the portions can divided equally (i.e. each overlapping fragment is about 21 to 25% of the entire full length if the target antigen) or unequally (i.e. a target antigen can be divided into the following 5 overlapping fragments; fragment 1 is about 25%, fragment 2 is about 5%, fragment 3 is about 35%, fragment 4 is about 10% and fragment 5 is about 25% of the size of the full length target antigen, provided each fragment overlaps with at least one other fragment).

Typically, a panel of LFn-fusions with fragments of a target antigen substantially covers the entire length of the whole (or intact) target antigen polypeptide. Accordingly, described herein is a method to detect a CMI response to a panel of target antigens which are overlapping proteins or polypeptides of the target antigen, rather than overlapping peptides of the target antigen. As the fragments which are fused to LFn are overlapping proteins, (as apposed to overlapping peptides) of a whole target antigen, they can be used to identify which polypeptide fragments of a whole target antigen elicit a CMI response. Overlapping protein fragments of a target antigen fused to LFn can be produced much quicker and cheaper, and with increased stability as compared to the use of peptides alone (not fused to LFn) in a CMI assay, thus significantly decreasing the cost of the assay as disclosed herein compared to other CMI assays using peptides. Further, polypeptides larger than simple peptides can be introduced with the LF polypeptide fusions described herein. Where conformation is important for epitope recognition, the larger fragments will provide a benefit over peptide fragments.

As discussed herein, using overlapping proteins of a target antigen fused to LFn increases the specificity of the CMI response. For example, the CMI assay as disclosed herein enables one to distinguish the difference between a subject which has been immunized against a pathogen and a subject who is infected with or has been exposed to a pathogen. In another example, the CMI assay as disclosed herein can distinguish between the T cell target. Accordingly, the diagnostic methods and CMI assay as disclosed herein provide a simple, cheap and rapid method to detect a CMI response to a target antigen and/or detect a subject affected with a pathology (such as a pathogen infection).

One of ordinary skill in the art can divide a whole target antigen into overlapping proteins of a target antigen which can be fused to LFn to create a panel of LFn-fusion polypeptides of the target antigen. By way of an illustrative example only, the TB-specific target antigen TB1 (CFP also known as culture filtrate-10 or CFP-10) comprising SEQ ID NO: 7 can be divided into, for example at least 17 fragments, such as those of SEQ ID NO: 30-46 shown in Table 1 to generate a panel of 17 different LFn-fusion polypeptides, each comprising a different but overlapping TB-specific target antigen TB1 (CFP) fragment fused to LFn. Culture filtrate protein (CFP-10) (Genbank AAC83445) is a 10 kDa,100 amino acid residue protein fragment from *M. tuberculosis*. It is also known as L45 antigen homologous protein (LHP). The amino acid sequence is (SEQ. ID. NO. 7)
MAEMKTDAATLAQEAGNELRISGDLKTQIDQVESTAGSLQGQWRGAAGTAAQAAVVRFQEAANKQK
QELDEISTNIRQAGVQYSRADEEQQQALSSQMGF.

In another example, the TB-specific target antigen TB2 (ESAT, also known as "early secreted antigenic target-6 polypeptide" or "ESAT-6") comprising SEQ ID NO: 6 can be divided into, for example at least 23 fragments, such as those of SEQ ID NO: 8-29 shown in Table 1 to generate a panel of 23 different LFn-fusion polypeptides, each comprising a different but overlapping TB-specific target antigen TB2 (ESAT) fragment fused to LFn. Early secreted antigenic target (ESAT-6) is a 95 amino acid residue protein fragment from *M. tuberculosis*. The amino acid sequence is (SEQ. ID. NO. 6)
MTEQQWNFAGIEAAASAIQGNVTSIHSLLDEGKQSLTKLAAAWGGSGSEAYQGVQQKWDATATELN
NALQNLARTISEAGQAMASTEGNVTGMFA.

In some embodiments, a fragment of a whole target antigen is substantially about a half the size of the full length target antigen, or substantially about a third the size of the full length target antigen, or substantially about a quarter the size of the full length target antigen or less than substantially a quarter the size the full length target antigen. In all cases, fragments of a full length whole target antigen should overlap with at least one, but preferably more than one other fragment of the whole target antigen. By way of an example, the panel of 17 different LFn-fusion polypeptides comprising different fragments of the TB1 (CFP) polypeptide, each fragment overlaps with at least two or three other fragments. The amount of overlap can vary depending on the size of the fragments and the number of the fragments into which the full length target antigen has been divided. A typical amount of overlap between fragments can be about 10%, or about 20% or about 30% or about 40% or about 50% or about 60% or about 70% or about 80% or more, or any overlap in between about 10% and about 80%. By way of an example, for each of the different fragments of the TB1 (CFP) target antigen polypeptide shown in Table 1, approximately 73% of each fragment overlaps with each adjacent fragment (i.e. each fragments overlaps with the fragment before it and after it by about 73%).

TABLE 1

| Fragments of whole TB-specific target antigens TB-1 (CFP) and TB-2 (ESAT) | |
|---|---|
| ESAT (TB2) | SEQ ID NO: 6 |
| RPMTEQQWNFAGIEA | SEQ ID NO: 8 |
| EQQWNFAGIEAAASA | SEQ ID NO: 9 |
| NFAGIEAAASAIQGN | SEQ ID NO: 10 |
| IEAAASAIQGNVTSI | SEQ ID NO: 11 |
| ASAIQGNVTSIHSLL | SEQ ID NO: 12 |
| IQGNVTSIHSLLDEGK | SEQ ID NO: 13 |
| TSIHSLLDEGKQSLT | SEQ ID NO: 14 |
| SLLDEGKQSLTKLAA | SEQ ID NO: 15 |
| EGKQSLTKLAAAWGG | SEQ ID NO: 16 |
| SLTKLAAAWGGSGSE | SEQ ID NO: 17 |
| LAAAWGGSGSEAYQG | SEQ ID NO: 18 |
| WGGSGSEAYQGVQQK | SEQ ID NO: 19 |
| GSEAYQGVQQKWDAT | SEQ ID NO: 20 |
| YQGVQQKWDATATEL | SEQ ID NO: 21 |
| VQQKWDATATELNNAL | SEQ ID NO: 22 |
| DATATELNNALQNLA | SEQ ID NO: 23 |
| TELNNALQNLARTIS | SEQ ID NO: 24 |
| NALQNLARTISEAGQ | SEQ ID NO: 25 |
| NLARTISEAGQAMAS | SEQ ID NO: 26 |
| TISEAGQAMASTEGN | SEQ ID NO: 27 |
| AGQAMASTEGNVTGM | SEQ ID NO: 28 |
| MASTEGNVTGMFALE | SEQ ID NO: 29 |
| CFP (TB1) | SEQ ID NO: 7 |
| RPLKNDAATLAQEAG | SEQ ID NO: 30 |
| NDAATLAQEAGNFER | SEQ ID NO: 31 |
| TLAQEAGNFLRISGD | SEQ ID NO: 32 |
| EAGNFLRISGDLKTQ | SEQ ID NO: 33 |
| FLRISGDLKTQIDQV | SEQ ID NO: 34 |
| SGDLKTQIDQVESTA | SEQ ID NO: 35 |
| KTQIDQVESTAGSLQ | SEQ ID NO: 36 |
| DQVESTAGSLQAQWR | SEQ ID NO: 37 |
| STAGSLQAQWRGAAG | SEQ ID NO: 38 |
| SLQAQWRGAAGTAAQ | SEQ ID NO: 39 |
| AQWRGAAGTAAQAAVV | SEQ ID NO: 40 |
| AAGTAAQAAVVRFQE | SEQ ID NO: 41 |
| AAQAAVVRFQEAANK | SEQ ID NO: 42 |
| AVVRFQEAANKQKAE | SEQ ID NO: 43 |
| FQEAANKQKAELDEI | SEQ ID NO: 44 |

TABLE 1-continued

| Fragments of whole TB-specific target antigens TB-1 (CFP) and TB-2 (ESAT) | |
|---|---|
| ANKQKAELDEISTNI | SEQ ID NO: 45 |
| KAELDEISTNIRLE | SEQ ID NO: 46 |

In some embodiments, a target antigen which is fused to LFn is any antigen associated with a pathology, for example an infectious disease or pathogen, or cancer or an immune disease such as an autoimmune disease. In some embodiments, a target antigen fused to LFn can be expressed by any of a variety of infectious agents, including a pathogen, virus, bacterium, fungus or parasite. A target antigen for use in the methods and compositions as disclosed herein can also include, for example, pathogenic peptides, toxins, toxoids, subunits thereof, or combinations thereof (e.g., cholera toxin, tetanus toxoid).

Bacterial pathogens for which a CMI response can be assayed include, as non-limiting examples, anthrax, campylobacter, cholera, diphtheria, enterotoxigenic *E. coli, giardia, gonococcus, Helicobacter pylori* (Lee and Chen, 1994), *Hemophilus influenza B, Hemophilus influenza* non-typable, *meningococcus, pertussis, pneumococcus, salmonella, shigella, Streptococcus* B, group A *Streptococcus, tetanus, Vibrio cholerae, yersinia, Staphylococcus, Pseudomonas* species, *mycobacterium, mycoplasma, neisseria, legionella* and *Clostridia* species.

A pathogen of particular interest is *Myocobacterium tuberculosis* (TB), an intracellular bacterial parasite. One example of a TB antigen is TbH9 (also known as Mtb 39A). Other TB antigens include, but are not limited to, DPV (also known as Mtb8.4), 381, Mtb41, Mtb40, Mtb32A, Mtb9.9A, Mtb9.8, Mtb16, Mtb72f, Mtb59f, Mtb88f, Mtb71f, Mtb46f and Mtb31f ("f" indicates that it is a fusion or two or more proteins).

Examples of other intracellular bacterial parasites that can be assayed for infection or exposure using the assays described herein include, but are not limited to, Rickettsia and Chlamydia species. Additional parasite pathogens include, for example: Entamoeba histolytica (Zhang et al., 1995); Plasmodium (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), Leishmania (Frankenburg et al., 1996), Toxoplasmosis, and the Helminths.

Viral pathogens for which a CMI response can be assayed include, as non-limiting examples: Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus, Rinderpest, Rhinovirus, Echovirus, Papova virus, Echinovirus, Arbovirus, Human Immunodeficiency virus type I or type II and Simian Immunodeficiency virus.

The ability to measure CMI is important for assessing a subject's ability to respond to an infection by an pathogenic agent such as a microorganism or virus or parasite, to mount an autoimmune response such as in diabetes or to protect against cancers or other oncological conditions. Consequently, reference to "measuring a CMI response to a target antigen in a subject" encompasses immune diagnosis of infectious and autoimmune diseases, a marker for immunocompetence and the detection of T-cell responses to endogenous and/or exogenous antigens (including a measure of the efficacy of a vaccine) as well as a marker for inflammatory diseases and cancer.

Any of a range of antigens may be tested such as those specific for a particular organism, pathogen, virus, auto-antigen or cancer cell. Alternatively, more general agents may be used to test generic capacity to mount or have mounted a cell-mediated immune response. Examples of the latter include PPD from M. tuberculosis and tetanus toxoid. In general, however, any polypeptide antigen can be used in the assay systems as disclosed herein.

Target antigens can also include those used in biological warfare, such as ricin, which may provoke a CMI response.

Autoimmune diseases involve CMI responses to self antigens. Autoimmune diseases contemplated for diagnosis according to the assays described herein include, but are not limited to alopecia areata, ankylosing spondylitis, antiphospholipid syndrome, Addison's disease, aplastic anemia, multiple sclerosis, autoimmune disease of the adrenal gland, autoimmune hemolytic anemia, autoimmune hepatitis, autoimmune oophoritis and orchitis, Behcet's Disease, bullous pemphigoid, cardiomyopathy, celiac sprue-dermatitis, chronic fatigue syndrome, chronic inflammatory demyelinating syndrome (CFIDS), chronic inflammatory polyneuropathy, Churg-Strauss syndrome, cicatricial pemphigoid, CREST Syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), Lichen Planus, lupus, Meniere's Disease, mixed connective tissue disease, myasthenia gravis, myocarditis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, stiff-man syndrome, Takayasu arteritis, temporal arteritis/giant cell arteritis, ulcerative colitis, uveitis, vasculitis and vitiligo. It is generally important to assess the potential or actual CMI responsiveness in subjects having, or suspected of having or being susceptible to an autoimmune disease.

Other disease conditions contemplated for diagnosis by detecting or monitoring a CMI response include, but are not limited to inflammatory disease conditions. Examples of inflammatory disease conditions contemplated for diagnosis or monitoring include but are not limited to acne, angina, arthritis, aspiration pneumonia, empyema, gastroenteritis, necrotizing enterocolitis, pelvic inflammatory disease, pharyngitis, pleurisy, chronic inflammatory demyelinating polyneuropathy, chronic inflammatory demyelinating polyradiculoneuropathy, and chronic inflammatory demyelinating polyneuropathy, among others.

Cancer therapy can also be dependent on CMI. For example, the ability to mount a CMI response to a tumor antigen can be important in determining whether an individual is a candidate for a therapeutic vaccine approach. Contemplated proliferative diseases and cancers include AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, astrocytoma, ataxia-telangiectasia, basal cell carcinoma (skin), bladder cancer, bone cancers, bowel cancer, brain and CNS tumors, breast cancer, carcinoid tumors, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumour, ductal carcinoma, endocrine cancers, endometrial cancer, ependymoma, esophageal cancer, Ewing's sarcoma, extra-hepatic bile duct cancer, eye cancer, including, e.g., eye melanoma and retinoblastoma, fallopian tube cancer, fanconi anemia, fibrosarcoma, gall bladder cancer, gastric cancer, gastrointestinal cancers, gastrointestinal-carcinoid-tumour, genitourinary cancers, germ cell tumors, gestational-trophoblastic disease, glioma, gynecological cancers, hematological malignancies, hairy cell leukemia, head and neck cancer, hepatocellular cancer, hereditary breast cancer, Hodgkin's disease, human papillomavirus-related cervical cancer, hydatidiform mole, hypopharynx cancer, islet cell cancer, Kaposi's sarcoma, kidney cancer, laryngeal cancer, leiomyosarcoma, leukemia, Li-Fraumeni syndrome, lip cancer, liposarcoma, lung cancer, lymphedema, lymphoma, non-Hodgkin's lymphoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer-(NSCLC), oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, renal cell carcinoma, retinoblastoma, rhabdomyosarcoma, Rothmund-Thomson syndrome, salivary gland cancer, sarcoma, Schwannoma, Sezary syndrome, skin cancer, small cell lung cancer (SCLC), small intestine cancer, soft tissue sarcoma, spinal cord tumours, squamous-cell-carcinoma-(skin), stomach cancer, synovial sarcoma, testicular cancer, thymus cancer, thyroid cancer, transitional-cell-cancer-(bladder), transitional-cell-cancer (renal-pelvis/ureter), trophoblastic cancer, urethral cancer, urinary system cancer, uterine sarcoma, uterus cancer, vaginal cancer, vulva cancer, Waldenstrom's-macroglobulinemia, and Wilms' tumor.

A target antigen for use in the methods and compositions described herein can be expressed by recombinant means, and can optionally include an affinity or epitope tag to facilitate purification (Summers and Smith, 1987; Goeddel, 1990; Ausubel et al., 1996). Chemical synthesis of an oligopeptide, either free or conjugated to carrier proteins, can be used to obtain antigen of the invention (Bodanszky, 1993; Wisdom, 1994). Oligopeptides are considered a type of polypeptide. It is preferred that the target antigen be expressed as a fusion with an LF polypeptide, e.g., with an LFn polypept ever, it is also possible to prepare target antigen and then conjugate it to an LF polypeptide, e.g., to an LFn polypeptide.

Polypeptides can also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another.

Antigen obtained through recombinant means or chemical polypeptide synthesis, as well as antigen obtained from natural sources or extracts, can be purified by means of the antigen's physical and chemical characteristics, preferably by fractionation or chromatography (Janson and Ryden, 1989; Deutscher, 1990; Scopes, 1993).

In some embodiments, a target antigen LFn-fusion polypeptide may be solubilized in water, a solvent such as methanol, or a buffer. Suitable buffers include, but are not limited to, phosphate buffered saline $Ca^{2+}/Mg^{2+}$ free (PBS), normal saline (150 mM NaCl in water), and Tris buffer. Antigen not soluble in neutral buffer can be solubilized in 10 mM acetic acid and then diluted to the desired volume with a neutral buffer such as PBS. In the case of antigen soluble only at acid pH, acetate-PBS at acid pH can be used as a diluent after solubilization in dilute acetic acid. Glycerol can be a suitable non-aqueous solvent for use the compositions, methods and kits described herein.

C. Complexes

Coupling of an LF polypeptide, e.g, an LFn polypeptide with a target antigen can be performed by any method or technique known in the art. For example, two polypeptides can be fused together by expression as a fusion protein. Coupling can also be accomplished by a chemical reaction that joins the two molecules, so long as the respective portions of the fusion protein, e.g., LFn and a target antigen retain their respective activities, i.e., permitting transmembrane transport into the cytosol of an intact, living cell and recognition as an antigen. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., *Imm. Rev.* 62:185-216, 1982; and Vitetta et al., supra).

Preferred linkages or linking agents are described in the literature. See, for example, Ramakrishnan, S., et al., *Cancer Res.* 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylaminopropyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the LF polypeptide-target antigen composition comprises an LF polypeptide, e.g., an LFn polypeptide, and the target antigen, but the LFn is not fused to the target antigen as a fusion protein, but rather the LFn is physically associated with the target antigen, forming, for example, an LFn:target antigen complex. In some embodiments that association is covalent, but it is also contemplated that the association can be non-covalent, e.g., where the LFn polypeptide is directly associated with the target antigen by van der Waals forces or other non-covalent interactions. In alternative embodiments, the composition comprises an LFn polypeptide:target antigen complex, where the LFn polypeptide is indirectly associated with the target antigen, for example by interaction of the LFn polypeptide with at least one third moiety. In such instances, the target antigen interacts with the same third moiety that interacts with the LFn polypeptide. Such interactions can be non-covalent bond association as known in the art, including, but not limited to, van der Waals forces, hydrophilic interactions, hydrophobic interactions and other non-covalent interactions. Other higher order interactions with intermediate moieties are also contemplated.

III. Immune Cells

Immune cells present in a biological sample of use in the methods described herein will necessarily include cells capable of indicating a cell mediated immune response. That is, antigen-sensitized immune cells in a biological sample useful in the methods described herein will, in response to delivery of antigen as an LF polypeptide fusion, release cytokine(s) indicative of the cells having been sensitized to that antigen Immune cells include, for example, antigen-specific lymphocytes such as B cells, $CD4^+$ T cells, CD8+ T cells, CTL, Th1 cells, Th2 cells, and/or T (DTH) cells). Moreover, a biological sample can comprise immune cells such as NK cells that mediate antibody-dependent cell-mediated cytotoxicity (ADCC). T cells are preferred immune cells for a sample useful in the methods described herein. It is emphasized that a biological sample need not contain purified or necessarily even enriched immune cells. Thus, whole blood, for example, is acceptable.

Detection Of Cytokines

Any method to detect the level of one or more cytokines can be used. For example, the level of IFN-γ can be measured using a commercial IFN-γ ELISA assay as described herein in the Examples. Typically at least one cytokine is measured, although a range of different cytokines are preferred, for example, at least 2, or at least about 3 or at least about 4 or at least about 5, at least about 6, at least about 7, at least about 8, at least about 9, at least about 10, or more than 10, such as at least about 15, at least about 20, at least about 25, at least about 30, at least about 35, at least about 40, at least about 45, or at least about 50 or more cytokines. The cytokines which are measured can include any known by one of ordinary skill in the art to be released by antigen-sensitized immune cells or cells that interact with them. Such cytokines can be selected, for example, from the group consisting of: GM-CSF; IL-1α; IL-β; IL-2; IL-3; IL-4; IL-5; IL-6; IL-7; IL-8; IL-10; IL-12; IFN-α; IFN-β; IFN-γ; MIP-1α; MIP-1β; TGF-β; TNFα and TNFβ. In particular embodiments, where a T-cell cytokine is measured, the cytokine can be, e.g., any one or a combination of the following cytokines: IFN-γ; TGFβ; TNFβ; IL-10; GM-CSF; IL-3; IL-4 and IL-5. In particular embodiments, a cytokine which is measured is IFN-γ. Examples of cytokines measured for a CMI response to given target antigen LFn-fusion polypeptides are shown in Table 2.

TABLE 2

| Target antigen or fragment thereof fused to LFn | Cytokine |
| --- | --- |
| TB, | IFN-γ. |
| EBV | IFN-γ. |
| HBV | IFN-γ, TNFα, IL-2, IL-10 |

In preferred embodiments, the level of cytokine protein released by an immune cell is measured. One can measure the level of cytokine protein by a variety of methods known in the art. These include, for example, an immunoassay, a radioimmunoassay (RIA), an immunoradiometric assay (IRMA), an enzyme-linked immunosorbent assay (ELISA), western blot analysis, an ELISpot, CELISA (cellular enzyme-linked immunosorbent assay), RHPA (reverse hemolytic plaque assay), a kinase receptor activation assay (KIRA), a cytokine immunotrapping assay (CITA), and a radioreceptor assay (RRA), among others. In some embodiments, the level of a cytokine can be determined by a bead-based multiplex assay, such as the commercially available Luminex assays (Dupont et al., J Reprod Immunol. 2005 Aug; 66(2):175-91, which is incorporated herein by reference) from panomics or other cytokine cytometric bead assays for the measurement of cytokines (Yong et a., J Immunol Methods. 2008, 29; 331(1-2):59-68; which is incorporated herein by reference). A wide range of immunoassay techniques are available to detect the level of cytokines as can be seen by reference to U.S. Pat. Nos. 4,016,043, 4,424,279 and 4,018,653 which are incorporated herein in their entirety by reference. The normal level (i.e. of non-infected and/or healthy individuals) of different cytokines in a biological sample, such as blood is well documented; for example see the "Cytokines & Cells Online Pathfinder Encyclopedia" (COPE) on the internet at "copewithcytokines.de/cope.cgi", in particular at world-wide web at: "copewithcytokines.de/cope.cgi?key=Cytokine%20Concentrations%20in%20Biological%20Fluids" which is incorporated herein by reference. The level of a cytokine released from the immune cell can also be measured at the level of gene transcription, e.g., by measuring mRNA.

A general approach for immunoassays is described below. Specific variations are described following that and in the Examples. A method for detecting a cytokine in a sample comprising immune cells from a subject can comprise contacting the sample or an aliquot of the sample with an antibody specific for the cytokine for a time and under conditions sufficient for an antibody-cytokine complex to form, and then detecting that complex. In some embodiments, a sample is, e.g., a whole blood sample. These methods can include micro-arrays and macro-arrays on planar or spherical solid supports.

In one type of immunoassay, an unlabeled antibody is immobilized on a solid substrate and the sample to be tested for the cytokines is brought into contact with the bound antibody molecule. After a suitable period of incubation, for a period of time sufficient to allow formation of an antibody-cytokine complex, a second antibody specific to the antigen, labeled with a reporter molecule capable of producing a detectable signal, is added and incubated, allowing time sufficient for the formation of another complex of antibody-cytokine-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of cytokine levels. This generalized technique is well known to those skilled in the art as would be any of a number of variations.

In these assays, a first antibody having specificity for the instant cytokines can be either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking, covalently binding or physically adsorbing. The polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. at about 20° C. to about 40° C.) to allow binding of any target cytokine present in the sample. Following the incubation period, the solid phase is washed and then incubated with a second antibody specific for a portion of the antigen. The second antibody is linked to a reporter molecule which is used to indicate the binding of the second antibody to the hapten. There are many variations to this assay. One particularly useful variation is a simultaneous assay where all or many of the components are admixed substantially simultaneously.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores, or radionuclide-containing molecules (i.e. radioisotopes) and chemiluminescent molecules. Other reporter molecules known in the art can be employed by one of skill in the art. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change, although, as noted above, it is also possible to employ fluorogenic substrates, which yield a fluorescent product, instead of a chromogenic substrate as noted above.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest Immunofluorescence and EIA techniques are both very well established in the art and are applicable for the present methods.

An ELISA is Enzyme-Linked ImmunoSorbent Assay, also called Enzyme ImmunoAssay or EIA, and is a biochemical technique used to detect the presence of a protein, such as a cytokine in a sample. In simple terms, a typical ELISA for use herein requires an unknown amount of a cytokine affixed to a surface, and then a specific antibody to the cytokine is washed over the surface so that it can bind to the antigen. This antibody is linked to an enzyme, and in the final step a substrate is added that the enzyme can convert to some detectable signal. In the case of fluorescence ELISA, when light of the appropriate wavelength is shone upon the sample, any antigen/antibody complexes will fluoresce so that the amount of antigen in the sample can be inferred through the magnitude of the fluorescence. Performing an ELISA for measuring cytokines in accord with the methods described herein involves at least one antibody with specificity for a particular cytokine. The sample, with an unknown amount of a cytokine, is immobilized on a solid support (usually a polystyrene microtiter plate) either non-specifically (via adsorption to the surface) or specifically (via capture by another antibody specific to the same cytokine, in a "sandwich" ELISA). After the target cytokine is immobilized the detection antibody is added, forming a complex with the cytokine. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of cytokine in the sample. Older ELISAs utilize chromogenic substrates, though newer assays employ fluorogenic substrates enabling much higher sensitivity.

An ELISpot assay is based on, and was developed from a modified version of the ELISA immunoassay. ELISPOT assays have been adapted for various tasks, especially the identification and enumeration of cytokine-producing cells at the single cell level. Simply put, at appropriate conditions the ELISPOT assay allows visualization of the secretory product of individual activated or responding cells, such as the release of cytokines from immune cells. Thus, the ELISPOT assay provides both qualitative (type of immune protein) and quantitative (number of responding cells) information.

The ELISPOT assay is much more sensitive than conventional ELISA enabling sensitivity and frequency analysis of rare cell populations (e.g., antigen-specific responses) due to, in part, the fact that the released cytokine is rapidly captured around the secreting immune cell. Limits of detection are below 1/100,000 rendering the assay uniquely useful for monitoring antigen-specific responses, applicable to a wide range of areas of immunology research, including cancer, transplantation, infectious disease, and vaccine development.

The assay has gained a recent increase in popularity, especially as a surrogate measure for CTL responses, in large part because it is both reliable and highly sensitive. A modern ELISPOT analysis is typically performed using ELISPOT readers, which employ computer vision techniques to enumerate the actively producing cells. This allows much of the analysis process to be automated, and permits a greater level of accuracy than what can be achieved using manual inspection. An exemplary ELISPOT assay for use in the methods as described herein employs a technique very similar to the sandwich enzyme-linked immunosorbent assay (ELISA) technique. Either a monoclonal or polyclonal capture antibody is coated aseptically onto a PVDF (polyvinylidene fluoride) -backed microplate. These antibodies are chosen for their specificity for the analyte in question. The plate is blocked, usually with a serum protein that is non-reactive with any of the antibodies in the assay. After this, cells, such as the cells present in the biological sample are plated out at varying densities, along with an LF polypeptide-antigen fusion polypeptide, and then placed in a humidified 37° C. $CO_2$ incubator for a specified period of time. A cytokine secreted by activated cells is captured locally by the coated antibody on the high surface area PVDF membrane. After washing the wells to remove cells, debris, and media components, a biotinylated polyclonal antibody specific for the chosen analyte is added to the wells. This antibody is reactive with a distinct epitope of the target cytokine and thus is employed to detect the captured cytokine. Following a wash to remove any unbound biotinylated antibody, the detected cytokine is then visualized using an avidin-HRP, and a precipitating substrate (e.g., AEC, BCIP/NBT). The colored end product (a spot, usually a blackish blue) typically represents an individual cytokine-producing cell. The spots can be counted manually (e.g., with a dissecting microscope) or using an automated reader to capture the microwell images and to analyze spot number and size.

Sadick et al (1999) have described a Kinase receptor activation assay (KIRA) as an alternative to end-point bioassays. This assay exploits the fact that ligand binding to receptors can cause tyrosine phosphorylation of the receptor. The authors have adapted this technique to assay IGF-1 and NGF by measuring the amount of receptor phosphotyrosine rather than cell proliferation (IGF-1) or cell survival (NGF). The authors demonstrate that this assay correlates well with the results obtained by classical bioassays. Alternative assays of cytokines frequently employ Factor-dependent cell lines or cell lines responding in a particular way to individual cytokines or freshly isolated cells.

Another method for detecting levels of cytokines is a radioreceptor assay (RRA) which measures concentrations of cytokines by displacing ligands from cell-bound receptors. The RHPA (reverse hemolytic plaque assay) is an adaptation of a plaque assay initially established to detect immunoglobulin-secreting cells and can be used to detect individual cells secreting cytokines and to determine the amounts of a particular cytokine secreted by this cell. The Cell blot assay also allows visualization of release of cytokines by producer cells.

An assay to study the kinetics of production and consumption or degradation of cytokines is Cytokine immunotrapping (CITA). This immunoassay allows determination of the rate of production of cytokines under conditions that prevent consumption/degradation. Cytokines secreted during cell culture are captured early by polystyrene macrobeads coated with monoclonal antibodies or by soluble antibodies and detected by a chemiluminescent immunoassay employing a second cytokine-specific antibody. A CITA assay has been established for the detection of IFN-γ and is also suitable for the early detection of IL1 and IL4. Under optimal conditions IFN-γ concentrations are higher (3-20-fold) than in conventional cultures, IFN-gamma production is detectable as early as 2 hours and IFN-γ secreted by less than 500 cells can be detected within 24 hours.

Another technique to detect intracellular cytokines is Cytokine flow cytometry. Flow cytometry offers a way to detect cytokines at the single cell level by means of fixation and permeabilization of cells with subsequent specific intracellular staining with the use of labelled monoclonal anti-cytokine antibodies. The technique also allows determination of cytokine production phenotypes by the simultaneous detection of two or more cytokines within a single cell. This is particularly useful, for example, for the identification of distinct T-helper subsets of lymphocytes (Th1 cells, Th2 cells) that differ in their cytokine production profiles. A survey of the kinetics of in situ cytokine production can be carried out also. The technique is useful also to correlate cytokine expression with expression of cell surface markers without cell separation. As such the technique has advantages over other cytokine assays or bioassays involving the use of factor-dependent cell lines.

Alternatively, and as stated above, detection of the cytokines can be made at the nucleic acid level. Consequently, reference to "presence or level of a cytokine" as that phrase is used herein includes direct (e.g., detection of cytokine proteins) and indirect (e.g., detection of cytokine mRNA) data. For example, high levels of IFN-γ mRNA is indirect data showing increased levels of IFN-γ. While other techniques can be used, a technique allowing the determination of mRNA encoding specific cytokines is RT-PCR. While RT-PCR based assays are specifically contemplated, it is noted that the detection of cytokines by transcription-based assays can be problematic if transcripts are detected but protein activity is not (see, for example, Marriott et al, 2002). Moreover, some cytokine genes give rise to alternatively spliced variants that may act as endogenous antagonists of the same cytokine (see: 1L4-delta-2, and the splice variants of HGF, designated HGF/NK1, HGF/NK2, HGF/NK4, for example). The ordinarily skilled artisan can determine whether nucleic acid detection is appropriate for the detection of cytokines in a given assay design.

The CMI assays as described herein can be automated or semi-automated for high throughput screening or for screening for a number of cytokines from a single subject. The automation is conveniently controlled by computer software. Accordingly, the methods described also contemplate a computer program product therefor, for assessing the presence or absence or the level of one or more cytokines, the product comprising: (1) code that receives, as input values, the identity of a reporter molecule associated with a labeled antibody or nucleic acid probe; (2) code that compares the input values with reference values to determine the level of reporter molecules and/or the identity of the molecule to which the reporter molecule is attached; and (3) a computer readable medium that stores the codes, optionally including (4) a graphical user interface or display that provides a read-out of a cytokine level to a user.

Another aspect extends to a computer for assessing the presence or absence or level of one or more cytokines, the computer comprising: (1) a machine-readable data storage medium comprising a data storage material encoded with machine-readable data, wherein the machine-readable data comprise input values which identify a reporter molecule associated with a labeled antibody or nucleic acid probe; (2) a working memory for storing instructions for processing the machine-readable data; (3) a central-processing unit coupled to the working memory and to the machine-readable data storage medium, for processing the machine readable data to compare the values to provide an assessment of the identity or level of reporter molecules or of molecules to which they are attached; and (4) an output hardware coupled to the central processing unit, for receiving and reporting the results of the comparison to a user.

The present invention further contemplates a kit for assessing a subject's exposure to an antigen of interest and/or a subject's capacity to mount a cell mediated immune response. The kit is conveniently in compartmental form with one or more compartments adapted to receive a sample from a subject, such as whole blood. That compartment or another compartment may also be adapted to contain heparin where the sample is whole blood.

Generally, the kit is in a form which is packaged for sale with a set of instructions. The instructions would generally be in the form of a method for measuring a CMI response in a subject, the method comprising collecting a sample from the subject wherein the sample comprises cells of the immune system which are capable of producing immune effector molecules following stimulation by an antigen, incubating the sample with an antigen and then measuring the presence or elevation in level of an immune effector molecule wherein the presence or level of the immune effector molecule is indicative of the subject having mounted a cell-mediated immune response to the target antigen and/or indicative of the capacity of the subject to mount a cell-mediated immune response.

Kits as described herein can comprise an LF polypeptide, e.g., an LFn polypeptide, fused to a target antigen, or a panel of such fusion polypeptides for measuring or monitoring a CMI response. Alternatively, or in addition, kits can include an LF polypeptide, e.g., an LFn polypeptide, and reagents for fusing or otherwise conjugating the LF polypeptide to a target antigen or to a panel of target antigen polypeptides.

Methods of measuring or detecting protein-protein interaction. Methods of measuring or detecting protein-protein interaction are well known. One skilled in the art can determine PA binding activity, for example, by mixing and incubating PA63 with LFn for a period of time, chemically cross-linking of any complex formed and analysis of the covalently linked complex by gel electrophoresis or by radioactivity counting as described by Quinn CP. et. al., 1991, J. Biol. Chem. 266:20124-20130. Briefly, the binding assay is determined at 5° C. by competition with radiolabeled $^{125}$I-LFn. Native LF or full-length N-terminal (amino acid 1-288) LFn is radiolabeled ($-7.3 \times 10^6$ cpm/µg protein) using Bolton-Hunter reagent (Amersham Corp). For binding studies, J774A.1 cells cultured in 24-well tissue culture plates are cooled by incubating at 4° C. for 60 min and then placing the plates on ice. The medium is then replaced with cold (4° C.) minimal essential medium containing Hanks' salts (GIBCO/BRL) supplemented with 1% (w/v) bovine serum albumin and 25 mM HEPES (binding medium). Native PA (0.1 g/ml) is added with radiolabeled native LF ($^{125}$I-LF, 0.1 µg/ml, $7.3 \times 10^6$ cpm/µg) and the plates incubated for 14 h on wet ice. Mutant LF proteins were assayed at varying concentrations for their ability to compete with native $^{125}$I-LF. For quantitation of bound, radiolabeled LF, cells were gently washed twice in cold binding medium, once in cold Hanks' balanced salt solution, solubilized in 0.50 ml of 0.1 M NaOH, and counted in a gamma counter (Beckman Gamma 9000).

Zinc metalloproteinase activity by FRET analysis. Assays of LF peptidolytic activity based on cleavage of the FRET-quenched substrate MAPKKide can be carried out according to a modification of the method of Cummings et al. (2002, Proc. Natl. Acad. Sci. USA 99:6603-6606.). MAPKKide (o-aminobenzoyl [o-ABZ]/2,4-dinitrophenyl [DNP]), a synthetic peptide containing the o-ABZ donor and DNP acceptor groups separated by a cleavage site specific for anthrax LF, was purchased from List Biological Labs. Digestion of MAP-KKide by LF was carried out in Dulbecco's phosphate-buffered saline (DPBS) (HyClone, Logan Utah), pH 8.2, as recommended by the manufacturer and was followed in a SpectraMax M2 microplate reader (Molecular Devices, Sunnyvale, Calif.) or in a, LS-5 fluorescence spectrophotometer (Perkin-Elmer, Wellesley, Mass.) using a $\lambda$ excitation (ex) value of 320 nm and a $\lambda$ emission (em) value of 420 nm. LF was preincubated with indicated concentrations of putative inhibitors for 10 min at room temperature, and the reaction was initiated by addition of indicated concentrations of the substrate to a 100-µl or 500-µl reaction mixture.

Systems

In one aspect, provided herein is a system for measuring a cell mediated immune response (CMI) to a target antigen in a subject, the system comprising a computer processor and a computer-readable physical storage medium having instructions recorded thereon sufficient to implement a process, employing the computer processor, for measuring a cell-mediated immune response, the instructions for said process comprising:

a) instructions for receiving data regarding the level of at least one cytokine released in a biological sample in response to contacting a cell in said sample with at least one fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein said contacting permits transmembrane delivery of said target antigen to a said cell, which cell processes and displays at least one epitope of said antigen on its surface; and b) instructions for comparing the level of said at least one cytokine in said biological sample with a reference level of said at least one cytokine, c) instructions for transmitting to a user interface a result of said comparison, wherein an increase in the level of said at least one cytokine in said biological sample from the subject as compared to a reference level indicates a cell mediated immune response (CMI) to the target antigen in the subject.

In another aspect, provided herein is a computer-readable physical storage medium having instructions recorded thereon sufficient to implement a process, employing a computer processor, for measuring a cell-mediated immune response, the instructions for said process comprising:

a) instructions for receiving data regarding the level of at least one cytokine released in a biological sample, said data obtained by: i) incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein said biological sample comprises cells of the immune system that release at least one cytokine in response to an antigen and wherein said incubating permits transmembrane delivery of said target antigen to a cell, which cell processes and displays epitopes of said antigen on its surface; and ii) measuring the level of at least one cytokine released in said biological sample;

b) instructions for comparing the level of said at least one cytokine in said biological sample with a reference level of said at least one cytokine, c) instructions for transmitting to a user interface a result of said comparison, wherein an increase in the level of said at least one cytokine in said biological sample from the subject as compared to a reference level indicates a cell mediated immune response (CMI) to the target antigen in the subject.

In another aspect, provided herein is a system for detecting a pathology of interest in a subject, the system comprising a computer processor a computer-readable physical storage medium having instructions recorded thereon sufficient to implement a process, employing the computer processor, for measuring a cell-mediated immune response, the instructions for said process comprising:

a) instructions for receiving data regarding the level of at least one cytokine released in a biological sample, said data obtained by a method comprising the steps of: i) incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein the target antigen is expressed in a tissue affected by the pathology, and wherein said biological sample comprises cells of the immune system that release at least one cytokine in response to an antigen; and ii) measuring the level of at least one cytokine released in said biological sample; and b) instructions for comparing the level of said cytokine in said biological sample with a reference level of the same cytokine; and c) instructions for transmitting to a user interface a result of the comparison of (b), wherein an increase in the level of said at least one cytokine in said biological sample from the subject as compared to a reference level identifies the subject as having, or having an increased risk of having said pathology.

In another aspect, provided herein is a computer-readable physical storage medium having instructions recorded thereon sufficient to implement a process, employing a computer processor, for measuring a cell mediated immune response (CMI) to a target antigen in a subject, the instructions for said process comprising:

a) instructions for receiving data regarding the level of at least one cytokine released in a biological sample, said data obtained by a method comprising the steps of: i) incubating a biological sample from said subject with at least one fusion polypeptide, the fusion polypeptide comprising a portion of an LF polypeptide lacking LF enzymatic activity but sufficient to promote transmembrane delivery of said fusion polypeptide to a cell, said portion fused to a target antigen polypeptide or to a fragment thereof, wherein the target antigen is expressed in a tissue affected by the pathology, and wherein said biological sample comprises cells of the immune system that release at least one cytokine in response to an antigen; and ii) measuring the level of at least one cytokine released in said biological sample; and b) instructions for comparing the level of said cytokine in said biological sample with a reference level of the same cytokine; and c) instructions for transmitting to a user interface a result of the comparison of (b), wherein an increase in the level of said at least one cytokine in said biological sample from the subject as compared to a reference level identifies the subject as having, or having an increased risk of having said pathology.

Computer-readable physical storage media useful in various embodiments include any physical computer-readable storage medium, e.g., magnetic and optical computer-readable storage media, among others. Carrier waves and other signal-based storage or transmission media are not included within the scope of physical computer-readable storage media encompassed by the term and useful according to the invention.

A user interface useful in various embodiments includes, for example, a display screen or a printer or other means for providing a readout of the result of a computer-mediated process. A user interface can also include, for example, an address in a network or on the world wide web to which the results of a process are transmitted and made accessible to one or more users. For example, the user interface can include a graphical user interface comprising an access element that permits entry of data regarding cytokine release in a biological sample, as well as an access element that provides a graphical read out of the results of a comparison transmitted to or made available by a processor following execution of the instructions encoded on a computer-readable medium.

Embodiments of the invention also provide for systems (and computer readable medium for causing computer systems) to perform a method for determining whether at biological test sample obtained from a subject has a positive CMI response to a target antigen, or alternatively has increased risk of having a specific pathology based on cytokine expression level information.

Embodiments of the invention have been described through functional modules, which are defined by computer executable instructions recorded on computer readable media and which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media, or computer readable medium 200, may define instructions, for example, as part of one or more programs, that, as a result of being executed by a computer, instruct the computer to perform one or more of the functions described herein (e.g., in relation to system 10, or computer readable medium 200), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 10, or computer readable medium 200 described herein, may be distributed across one or more of such components, and may be in transition there between.

The computer-readable media may be transportable such that the instructions stored thereon can be loaded onto any computer resource to implement the aspects of the present invention discussed herein. In addition, it should be appreciated that the instructions stored on the computer readable media, or the computer-readable medium 200, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The functional modules of certain embodiments of the invention include a determination module, a storage device, a comparison module and a display module. The functional modules can be executed on one, or multiple, computers, or by using one, or multiple, computer networks. The determination module 40 has computer executable instructions to provide sequence information in computer readable form. As used herein, "cytokine level information" refers to the expression level, preferably protein expression level of at least one or more cytokines measured in the biological sample, including but not limited to GM-CSF; IL-1α; IL-1β; IL-2; IL-3; IL-4; IL-5; IL-6; IL-7; IL-8; IL-10; IL-12; IFN-α; IFN-β; IFN-γ; MIP-1α; MIP-1β; TGF-β; TNFα and TNFβ and fragments and variants thereof. Moreover, information "related to" the cytokine level information includes detection of the presence or absence of precursor proteins of at least one cytokine, or the presence or absence of messenger RNA sequence encoding the cytokine), determination of the concentration and level of protein expression of the cytokine in the biological sample (e.g., amino acid sequence expression levels, or in some ebodiments nucleotide (RNA or DNA) expression levels), and the like. The term "cytokine level information" is intended to include the presence or absence of post-translational modifications (e.g. phosphorylation, glycosylation, summylation, farnesylation, and the like) of the measured cytokines, the presence or absence of the measured cytokines and the level of protein expression of the cytokines.

As an example, determination modules 40 for determining cytokine level information may include known systems for automated protein expression level determination, including for example, but not limited to, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Applicaion, Pub. No. U.S. 2003/0194711, which is incorported herein in its entirety by reference); systems for array based expression analysis: e.g., HT array systems and cartridge array systems such as GENECHIP® AUTOLOADER, COMPLETE GENECHIP® Instrument System, GENECHIP® Fluidics Station 450, GENECHIP® Hybridization Oven 645, GENECHIP® QC Toolbox Software Kit, GENECHIP® Scanner 3000 7G plus Targeted Genotyping System, GENECHIP® Scanner 3000 7G Whole-Genome Association System, GENETITAN™ Instrument, and GENECHIP® Array Station (each available from Affymetrix, Santa Clara, Calif.); automated ELISA systems (e.g., DSX® or DS2® (available from Dynax, Chantilly, Va.) or the TRITURUS® (available from Grifols USA, Los Angeles, Calif.), The MAGO® Plus (available from Diamedix Corporation, Miami, Fla.) ; Densitometers (e.g. X-Rite-508-SPECTRO DENSITOMETER® (available from RP IMAGINGTM, Tucson, Ariz.). The HYRYSTM 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACS-Vantage SE, (available from Becton Dickinson, Franklin Lakes, N.J.); and radio isotope analyzers (e.g. scintillation counters).

Alternatively, determination modules 40 for determining cytokine level information may include known systems for automated detection of sequencing the nucleotide (i.e. RNA expression) of the cytokines, including sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALFTM DNA Sequencer and Pharmacia ALFexpress™ (available from Amersham Biosciences UK Limited, Little Chalfont, Buckinghamshire, England). The cytokine level information determined in the determination module can be read by the storage device. As used herein the "storage device" 30 is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices 30 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. Storage devices 40 are also commonly referred to in the art as "computer-readable physical storage media" which is useful in various embodiments, and can include any physical computer-readable storage medium, e.g., magnetic and optical computer-readable storage media, among others. Carrier waves and other signal-based storage or transmission media are not included within the scope of storage devices 40 or physical computer-readable storage media encompassed by the term and useful according to the invention. The storage device is adapted or configured for having recorded thereon cytokine level information or cytokine protein expression level information. Such information may be provided in digital form that can be transmitted and read electronically, e.g., via the Internet, on diskette, via USB (universal serial bus) or via any other suitable mode of communication.

As used herein, "expression level information" refers to any nucleotide and/or amino acid expression level information of at least one cytokine, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like.

As used herein, "stored" refers to a process for encoding information on the storage device 30. Those skilled in the art can readily adopt any of the presently known methods for recording information on known media to generate manufactures comprising the cytokine level information or cytokine protein expression level information.

A variety of software programs and formats can be used to store the cytokine level information or cytokine protein expression level information on the storage device. Any number of data processor structuring formats (e.g., text file or database) can be employed to obtain or create a medium having recorded thereon the cytokine level information or cytokine protein expression level information.

By providing cytokine level information or expression cytokine level information in computer-readable form, one can use the cytokine level information or cytokine expression level information in readable form in the comparison module 80 to compare a specific cytokine level or cytokine expression profile with the reference data within the storage device 30. For example, search programs can be used to identify which cytokines are expressed (reference data, e.g., presence or absence of cytokine information obtained from at lease one control sample) or direct comparison of the determined cytokine expression level can be compared to the reference data cytokine expression level (e.g., cytokine level information obtained from a control sample). The comparison made in computer-readable form provides a computer readable comparison result which can be processed by a variety of means. Content 140 based on the comparison result can be retrieved from the comparison module 80 to indicate the presence or absence of a CMI response to the target antigen or a panel of target antigens, or in some embodiments a signal to indicate the presence of, or likelihood of developing a pathology.

In one embodiment the reference data stored in the storage device 30 to be read by the comparison module 80 is cytokine level information data obtained from a control biological sample of the same type as the biological sample to be tested. Alternatively, the reference data are a database, e.g., an expression level profile (RNA, protein or peptide) of cytokines in normal pathology unaffected subjects. In one embodiment the reference data are cytokine level information or cytokine expression level profiles that are indicative of a having a CMI response to the target antigen or panel of target antigens, or a subject having or likely to develop a pathology.

In one embodiment, the reference data are one or more reference cytokine protein levels selected from the group consisting of, but not necessarily limited to GM-CSF; IL-1α; IL-1β; IL-2; IL-3; IL-4; IL-5; IL-6; IL-7; IL-8; IL-10; IL-12; IFN-α; IFN-β; IFN-γ; MIP-1α; MIP-1β; TGF-β; TNFα and TNFβ.

In one embodiment, the reference data are electronically or digitally recorded and annotated from databases including, but not limited to protein expression databases commonly known in the art, such as Yale Protein Expression Database (YPED), or the Cytokine Family Database (dbCFC), as well as GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting cytokine level information can be stored in a relational data base that may be employed to determine homologies between the reference data or genes or proteins within and among genomes.

The "comparison module" 80 can use a variety of available software programs and formats for the comparison operative to compare sequence information determined in the determination module 40 to reference data. In one embodiment, the comparison module 80 is configured to use pattern recognition techniques to compare cytokine level information from one or more entries to one or more reference data patterns. The comparison module 80 may be configured using existing commercially-available or freely-available software for comparing protein expression patterns, and may be optimized for particular data comparisons that are conducted. The comparison module 80 provides computer readable information related to the sequence information that can include, for example, detection of the presence or absence of a cytokine protein or RNA, the level of cytokine protein expression information, detection of post-translational modification of cytokine protein; determination of the concentration of cytokine protein in the biological sample (e.g., amino acid sequence/protein expression levels, or nucleotide (RNA or DNA) expression levels, or levels of post-translational modification), or determination of an expression cytokine profile comprising at least one of a variety of different cytokines, or their pre-proteins or variants including homologues and post-translated modificated cytokines.

The comparison module 80, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware--as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the comparison module 80 performs comparisons with mass-spectometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Cytokine protein expression profiles can be discerned.

In one embodiment, the comparison module 80 compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

In one embodiment, the comparison module 80 compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allows a comparative analysis of 2 or more microarray data sets.

In one embodiment of the invention, pattern comparison software is used to determine whether patterns of protein expression are indicative of a CMI response or in some embodiments, indicitave of a subject having or likely to develop a pathology.

The comparison module 80 provides computer readable comparison result that can be processed in computer readable form by predefined criteria, or criteria defined by a user, to provide a content based in part on the comparison result that may be stored and output as requested by a user using a display module 110. The display module 110 enables display of a content based in part on the comparison result for the user, wherein the content 140 is a signal indicative of the presence or absence of a CMI response to the test target antigen or the test panel of target antigens. Such signal, can be for example, a display of content 140 indicative of the presence or absence of a CMI response to the test target antigen or the test panel of target antigens on a computer monitor, a printed page of content 140 indicating the presence or absence of a CMI response to the test target antigen or the test panel of target antigens from a printer, or a light or sound indicative of the presence or absence of CMI response to the test target antigen or the test panel of target antigens. Where the CMI response is to a panel of target antigens, such signal, can be for example, a display of content 140 indicative of the presence or absence of a CMI response to one or more particular target antigens selected from the panel of target antigens on a computer monitor, a printed page of content 140 indicating the presence or absence of a CMI response to one or more particular target antigens selected from the panel of target antigens from a printer, or a light or sound indicative of the presence or absence of CMI response to one or more particular target antigens selected from the panel of target antigens.

In some embodiments, the content 140 is a signal indicative that the subject from which the biological sample was obtained has, or is likely to develop a pathology. Such signal, can be for example, a display of content 140 indicative the presence or absence of a pathology in the subject on a computer monitor, a printed page of content 140 indicating the presence or absence of a pathology in the subject from a printer, or a light or sound indicative of the presence or absence of a pathology in the subject.

The content 140 based on the comparison result may include an expression profile of one or more cytokine proteins, or an expression profile of one or more cytokine genes. In one embodiment, the content 140 based on the comparison includes the presence or absence of at least one cytokine protein and a determination of the level of at least one cytokine protein, or specific post-translational modification of at least one protien. In one embodiment, the content 140 based on the comparison result is merely a signal indicative of the presence or absence of a CMI response to the test target antigen or the test panel of target antigens.

In one embodiment of the invention, the content 140 based on the comparison result is displayed a on a computer monitor. In one embodiment of the invention, the content 140 based on the comparison result is displayed through printable media. In one embodiment of the invention, the content 140 based on the comparison result is displayed as an indicator light or sound. The display module 110 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif. or any other type of processor, visual display devices such as flat panel displays, cathode ray tubes and the like, as well as computer printers of various types.

In one embodiment, a World Wide Web browser is used for providing a user interface for display of the content 140 based on the comparison result. It should be understood that other modules of the invention can be adapted to have a web browser interface. A user interface useful in various embodiments includes, for example, a display screen or a printer or other means for providing a readout of the result of a computer-mediated process. A user interface can also include, for example, an address in a network or on the world wide web to which the results of a process are transmitted and made accessible to one or more users. For example, the user interface can include a graphical user interface comprising an access element that permits entry of data regarding cytokine release in a biological sample, as well as an access element that provides a graphical read out of the results of a comparison transmitted to or made available by a processor following execution of the instructions encoded on a computer-readable medium. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the cytokine level information, e.g., display of an indication of the presence or absence of CMI response to the target antigen or a panel of target antigens (i.e. a positive or negative CMI response); display of expression levels of the cytokine proteins measured; display of nucleotide (RNA or DNA) cytokine expression levels; display of cytokine protein expression as compared to reference cytokine level information, display of cytokine protein expression level for each target antigen in selected from the panel of target antigens tested, or display of cytokine level information based thereon. In one embodiment, the cytokine level information of the reference sample data is also displayed.

In one embodiment, the display module 110 displays the comparison result and whether the comparison result is indicative of a CMI response, e.g., whether the expression profile of cytokines is indicative of a positive or negative CMI response to the target antigen or a target antigen from a panel of target antigens tested.

In one embodiment, the display module 110 displays the comparison result and whether the comparison result is indicative of a subject having or having an increased risk of a pathology, e.g., whether the expression profileof the measured cytokines is indicative of a a subject having or having an increased risk of a pathology, as determined by the presence of a CMI response to the target antigen, or a target antigens from a panel of target antigens tested.

In one embodiment, the content 140 based on the comparison result that is displayed is a signal (e.g. positive or negative signal) indicative of the presence or absence of a CMI response(i.e. a positive or negative CMI response) the tested target antigen or panel of target antigens, thus only a positive or negative CMI response indication may be displayed. In an alternative embodiment, where a panel of target antigens were tested, the content 140 based on the comparison result that is displayed is a signal (e.g. positive or negative signal) indicative of the presence or absence of a CMI response(i.e. a positive or negative CMI response) to each target antigen from the panel of target antigens, thus a positive or negative indication of a CMI response to a specific target antigen in a panel of target antigens may be displayed (i.e. a positive or negative CMI response to each specific target antigen in a panel of target antigens assessed).

The present invention therefore provides for systems 10 (and computer readable medium 200 for causing computer systems) to perform methods for determining the presence of a CMI response (i.e. a positive or negative CMI response) in the biological sample in response to the target antigen or panel of target antigens, and in some embodiments, whether a subject has, or will likely develop, a patholgy based on the cytokine level expression profiles or cytokine level information.

System 10, and computer readable medium 200, are merely an illustrative embodiments of the invention for performing methods of determining the presence of a CMI response (i.e. a positive or negative CMI response) in the biological sample in response to the target antigen or panel of target antigens, and in some embodiments, whether a subject has, or likely will develop a patholgy based on the cytokine level expression profiles or cytokine level information, and is not intended to limit the scope of the invention. Variations of system 10, and computer readable medium 200, are possible and are intended to fall within the scope of the invention.

The modules of the system 10 or used in the computer readable medium 200, may assume numerous configurations. For example, function may be provided on a single machine or distributed over multiple machines.

Figure 14:
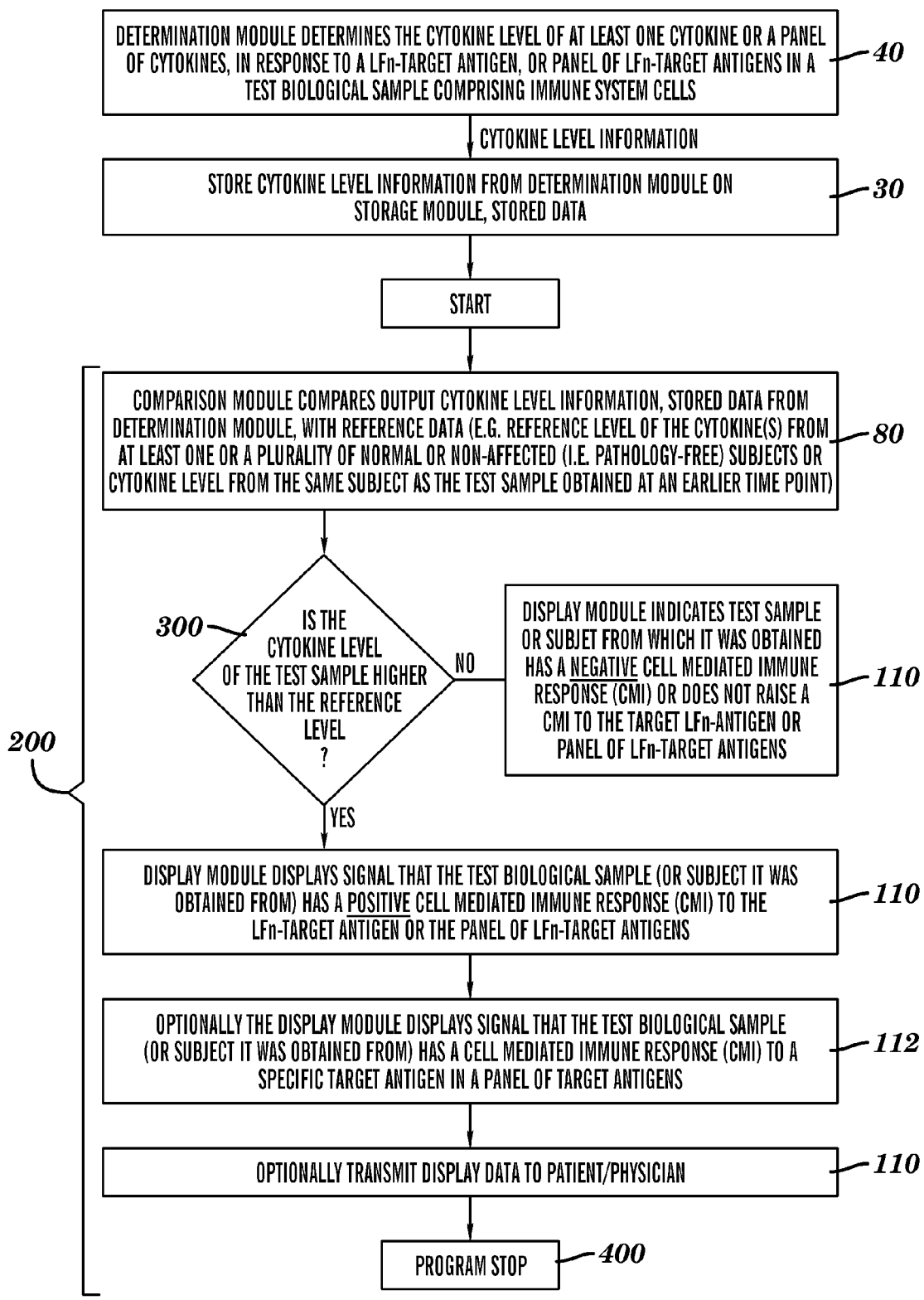
FIG. 14 is a block diagram showing exemplary instructions on a computer readable medium for assessing a positive or negative CMI response to a target antigen or panel of target antigens in a biogical sample.

FIG. 14 is a block diagram of a computer readable media 200 according to one embodiment of the invention. The system shown in FIG. 14 for performing the comparison processing of the invention may be a general purpose computer used alone or in connection with a specialized processing computer. Such processing may be performed by a single platform or by a distributed processing platform. In addition, such processing and functionality can be implemented in the form of special purpose hardware or in the form of software being run by a general purpose computer. Any data handled in such processing or created as a result of such processing can be stored in a temporary memory, such as in the RAM of a given computer system or subsystem. In addition, or in the alternative, such data may be stored in longer-term storage devices, for example, magnetic disks, rewritable optical disks and so on.

Figure 13:
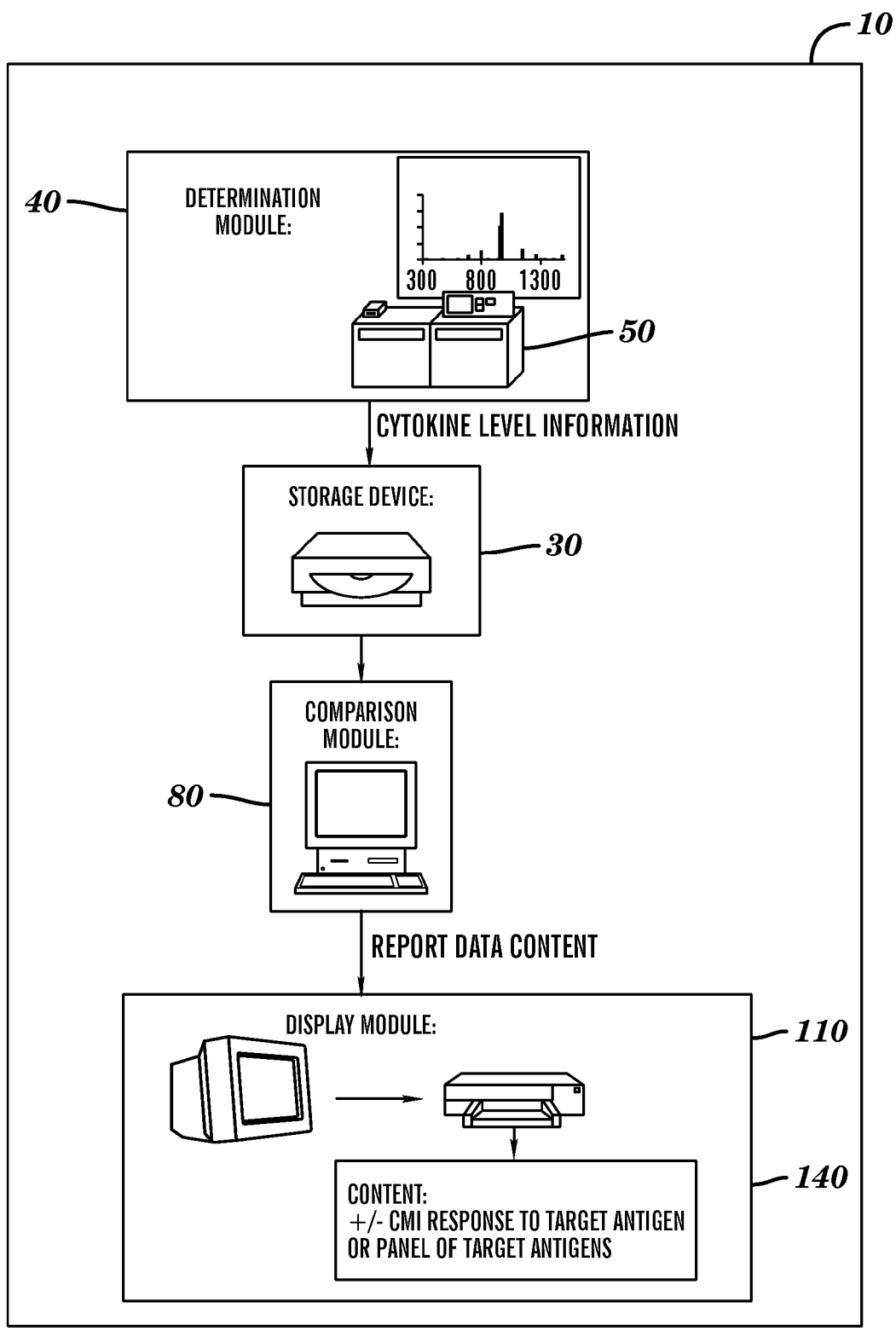
FIG. 13 is a block diagram showing an example of a system for assessing the presence of a CMI response to a target antigen or panel of target antigens in a biogical sample.

The computer system 10 (FIG. 13) may include an operating system (e.g., UNIX) on which runs a relational database management system, a World Wide Web application, and a World Wide Web server. The software on the computer system may assume numerous configurations. For example, it may be provided on a single machine or distributed over multiple machines.

A World Wide Web browser may be used for providing a user interface. Through the Web browser, a user may construct search requests for retrieving data from a sequence database and/or a genomic database. Thus, the user will typically point and click to user interface elements such as buttons, pull down menus, scroll bars, etc. conventionally employed in graphical user interfaces. The requests so formulated with the user's Web browser are transmitted to a Web application which formats them to produce a query that can be employed to extract the pertinent information from relevant databases, e.g. reference level databases. When network employs a World Wide Web server, it supports a TCP/IP protocol. Local networks such as this are sometimes referred to as "Intranets." An advantage of such Intranets is that they allow easy communication with public domain databases residing on the World Wide Web (e.g., the GenBank World Wide Web site). Thus, in a particular preferred embodiment of the present invention, users can directly access data (via Hypertext links for example) residing on Internet databases using a HTML interface provided by Web browsers and Web servers. USES The methods and compositions described herein are useful to detect or monitor a CMI response to a target antigen using a biological sample obtained from a subject. Accordingly, the present invention can be used to diagnose if the subject has been previously exposed to the target antigen, for example if the subject has, or is at risk of developing a pathology, including but not limited to one caused by a pathogen. Because a target antigen fused to an LF polypeptide, e.g., an LFn polypeptide, can be any antigen associated with an infectious disease, or cancer or immune disease, the methods described herein are useful for diagnosing if a subject has, or is at risk of developing a pathology from a variety of infectious agents, including a virus, bacterium, fungus or parasite, as well as from cancer and/or immune diseases such as auto-immune diseases. The methods and compositions described herein can also be used to monitor the ability of an individual to effect a CMI response to a target antigen.

In some embodiments, the CMI assay as disclosed herein is useful for diagnostic and prognostic analysis or monitoring of a subject with a pathology. For example, as immune cells release certain cytokines in response to stimulation with specific target antigens but not others, the measurement of a unique or characteristic profile of cytokines enables one to specifically and qualitatively diagnose whether a subject has a chronic infection or is a carrier. Alternatively, a unique or characteristic profile of cytokines for a CMI response to a specific target antigen or target-antigen fragment enables one to distinguish if a subject is infected with one subtype (or variant) of a pathogen vs. a different subtype (i.e. variant) of pathogen based on the release of a unique or characteristic profile or set of cytokines from the T-cells. By way of example, the cytokine profile of a chronically infected subject will be different from the cytokine profile of a carrier subject, and similarly a subject infected with one pathogen subtype will be different from the cytokine profile of a subject infected with a different pathogen subtype (i.e. variant). Accordingly, one can distinguish patients with acute (i.e. a carrier) or chronic (infectious) pathogenic infections.

One example is use of the CMI assay as disclosed herein to distinguish subjects with primary TB infection (A-TB) which accounts for approximately 10% of infected individuals, and non-infectious symptom-free TB infected individuals which have latent TB infection (LTBI). Similarly, the use of the CMI assay as disclosed herein can be used to distinguish subjects infected with different HIV strains. By way of an example, if a positive CMI response is detected to a full length target antigen LFn fusion polypeptide, such as to an HIV antigen such as gag, one can use a panel of LFn-polypeptide-comprising fragments of the gag target antigen which are specific to different variants of HIV, and thus distinguish which variant of HIV results in a positive CMI response and thus which variant of HIV the subject has been exposed to, and/or is infected with.

In addition, the present invention can be used for epitope mapping. For example, the CMI assay as disclosed herein can be used to identify which epitope of the full length target antigen leads to a positive CMI response. Using the example of HIV again, if a positive CMI response is detected to a full length HIV target antigen LFn fusion polypeptide, such as, for example gag, one can use a panel of LFn-polypeptides comprising substantially overlapping polypeptide fragments of the gag target antigen to identify which such fragments of the gag full length polypeptide lead to a CMI response. Such knowledge of which part of a target antigen leads to a CMI response is useful in designing both improved diagnostic tools (i.e. an improved specificity and/or accuracy of CMI assay herein) (e.g. for HIV infection) and/or design of new therapeutics, such as vaccines (e.g. anti-HIV vaccines) and the like.

As the present invention is rapid, easy to use and cost-efficient, it is can be useful as an on-site "field kit" diagnostic tool to diagnose individuals in a population who have a pathology and/or pathogenic infection. For example, one can use the CMI assay as disclosed herein to screen large populations of subjects rapidly and at the geographical location of interest. For example, one can use the assay to screen large populations of subjects for TB, HBV, HIV and other such pathogenic disease including contagious diseases, in order to monitor and prevent the spread of a disease epidemic, as well as to provide treatment to those subjects affected with the disease and/or pathogenic infection. This is particularly useful to monitor and/or prevent the spread of highly contagious diseases, for example but not limited to; Ebola which affects human subjects, and avian flu which affects birds and foot and mouth disease which affects livestock, where a rapid, sensitive, accurate and easy on-site diagnostic method is an important step in strategies to treat affected subjects, promote quarantine of affected subjects and prevent a wide-spread disease epidemic.

In one embodiment, described herein is a method of treatment of a subject having a pathogenic infection, an autoimmune disorder or cancer or a propensity for developing such a disorder, the method comprising assessing the ability for the subject to mount a cell mediated immune response by a method of measuring a CMI response described herein, the method comprising collecting a sample from said subject wherein the sample comprises cells of the immune system which are capable of releasing cytokines following stimulation by an antigen, incubating the sample with an LF polypeptide-antigen polypeptide fusion and then measuring the presence of, or increase in the level of a cytokine wherein the presence or level of the cytokine is indicative of the capacity of the subject to mount a cell-mediated immune response, and then selecting a suitable therapeutic protocol.

In another aspect, the methods and compositions for the CMI assay are useful for prognosis evaluations of subjects. For example, as discussed above, one can use the CMI assay to distinguish between chronic infected subjects, carrier subjects or latently infected subjects. Alternatively, one can distinguish between subjects infected with different variants of a pathogen. In another embodiment, one can use the CMI assay as disclosed herein to identify which epitope of the target antigen is useful in the diagnosis and/or prognosis. This is useful to aid in the treatment of subjects. For example, the CMI assay can be used to determine which epitope is predominant, and therefore can be used as a target to stimulate cells that respond to that epitope.

In another embodiment, the methods described herein also encompass the use of the compostions as disclosed herein for a diagnostic in vivo CMI assay. In one embodiment, one can use ae target antigen LFn-fusion polypeptide in a diagnostic CMI skin test. For example, one can deliver an effective amount of at least one target antigen LFn-fusion polypeptide subcutaneously to a subject and monitor the response. A positive CMI response is detected by measuring an acute inflammatory reaction surrounding the site of subcutaneous administration of the target antigen LFn-fusion polypeptide at an appropriate timepoint after the administration, for example, about 24hrs, or about 48hrs, or about 3 days, or about 4 days, or about 5 days, or about 7 days or more after administration. A acute inflammatory response is detected as an area of reddening of the skin surrounding the administration site as compared to the reddening of area from the subcutaneous administration of a control polypeptide (such as LFn alone (i.e. not fused to a target antigen) or a saline injection). The effective amount of the target antigen LFn-fusion polypeptide in a diagnostic CMI skin is significantly much lower than the effective amount of the target antigen LFn-fusion polypeptide when used as a therapeutic, for example as a vaccine or for another therapeutic purpose. Typically, an effective amount of the target antigen LFn-fusion polypeptide in a diagnostic CMI skin test is sufficient to result in a CMI response by the subject, yet insufficient to raise a significant immune response. Advantages of such an assay include the ability to detect exposure to essentially any epitope of a target antigen, rather than just those epitopes that gain access to a cell in a peptide-based assay. Modifications of the LF polypeptide that reduce its immunogenicity while maintaining its transmembrane transport facilitation can be used in this aspect.

In embodiments where a target antigen LFn-fusion polypeptide is used in a diagnostic CMI skin assay, the assay can involve the subcutaneous administration of more than one target antigen LFn-fusion polypeptide. For example, a subject can be administered a whole target antigen LFn-fusion polypeptide, as well as a panel of LFn-fusion polypeptides which comprise overlapping polypeptide fragments of the full length target antigen. In a further embodiment, one can also administer different types of full length target antigens fused to LFn (and panels of LFn-fusion polypeptides thereof) such as different target antigens from different pathogens (i.e. target antigens expressed by TB and HIV), or different target antigens from the same pathogen (i.e. target antigens from HIV1 and HIV2 or target antigens from different strains or variants of a pathogen). Such a diagnostic CMI skin assay is applicable to all types of target antigens from different pathologies, such as cancer, pathogenic infections and immune/auto-immune diseases. Such a diagnostic CMI skin assay is highly useful for a rapid, specific and highly accurate method to screen a subject for having or risk of developing multiple pathologies in a single step.

In alternative embodiments, the compositions and methods as disclosed herein can be useful in the diagnosis and protection against TB, tetanus, diphtheria and other toxin-mediated diseases to induce the production of anti-toxin antibodies. For example, a tetanus "booster" patch is envisioned in the present invention, where the composition as disclosed herein comprises LFn or a fragment thereof and a target antigen toxoid such as tetanus toxin or diphtheria, or fragments such as the tetanus C fragment. Boosting could be achieved following primary immunization by injection or transcutaneous immunization with the same or similar antigens. For injectable immunizations that induce immunity but have potential side effects upon boosting, a transcutaneous boost may be preferable, or oral or nasal immunization can be used to "boost" an immune response against the target antigen. In some embodiments, simultaneous use of injectable and transcutaneous immunizations could also be used.

There are numerous markets where the CMI assay as disclosed herein could have a significant impact, including in prisons and jails, public health TB programs, and for screening recent immigrants, healthcare workers and military personnel. The CMI assay as disclosed herein can be easily used with healthcare providers across the U.S. and worldwide an alternative to the TB skin test (TST).

The CMI assay as disclosed herein for testing for a CMI response to TB for example, will yield dramatic cost savings in terms of medical staff time and the elimination of common false-positive results. For hospitals and health departments, such a test for TB would relieve the huge administrative and cost burden associated with maintaining TB testing compliance. According to a recent study (Lambert et al. Infection Control and Hospital Epidemiology November 2003), researchers observed that the cost of running a TB control program using the TB skin test (TST) is considerably more expensive than the simple cost of the TST supplies, given the labor required to successfully perform the TST. Specifically, costs to a hospital ranged from $41 to $362 per employee, with the TST supplies representing less than 1.5 percent of the total cost of the program. The CMI assay as disclosed herein can be used as an in vitro diagnostic test unaffected by subjective interpretation of the physician or nurse, previous BCG vaccination, and cross-reactivity with most non-tuberculous or environmental mycobacteria. These capabilities mean virtual elimination of those TST false-positive individuals normally recommended for unnecessary and potentially harmful TB therapy. For the U.S.-born population, the false-positive rate due to non-tuberculous mycobacterial infections can be as much as 50 percent of all TST responses (von Reyn et al. Int J. Tuberc Lung Dis 5(12), 2001). For foreign-born individuals living in the U.S., cross-reactivity to past TB vaccination with Bacillus Calmette-Guerin (BCG) is a common cause of false-positive TST responses. The TST originated in the 1890's and until now was the only widely used method for detecting latent TB infection. However, the TST has many limitations and its effectiveness for controlling TB in the U.S. was questioned in the U.S. Institute of Medicine's 2000 major report, Ending Neglect, which stated that "the greatest needs in the United States are new diagnostic tools for the more accurate identification of individuals who are truly infected." Interpreting the TST is highly subjective, the test has poor reproducibility and requires two patient encounters; one to inject the subject and a second to read the inflammation it may produce. Commonly, up to 30 percent of individuals tested do not return to have their results read. Of major significance, the TST is confounded by previous vaccination with BCG, as well as exposure to non-tuberculosis mycobacteria, resulting in a high rate of people with TST false-positive results. In contrast, the CMI assay as disclosed herein measures immune responses to overlapping peptides that simulate *M. tuberculosis* proteins which are not present in the BCG vaccine or most non-tuberculosis mycobacteria. Thus, the CMI assay as disclosed herein is highly specific and a positive test result is strongly predictive of true infection with *M. tuberculosis*. A global TB epidemic was declared by the World Health Organization (WHO) in 1993. TB is the largest microbial killer in the world, responsible for more than two million deaths each year. It is an airborne disease that is adapting to misused medications, growing stronger and becoming more multi-drug-resistant. While the overall TB incidence in the U.S. is slowly decreasing, TB is resurfacing in several, "hot spot" metropolitan areas due to large immigrant and migrant populations, as well as individuals with immunosuppressive diseases such as HIV. The CDC estimates that 10 to 15 million U.S. residents are infected with TB in its latent (non-symptomatic) phase. Infected individuals are at risk of developing active TB disease, and becoming the source of continual transmission.

Methods to Generate Target Antigen LF Polypeptide-Fusion Polypeptides

As described above, LF polypeptides, e.g., LFn and variants thereof can be used in the methods and compositions of the invention. Recombinant LFn can be conveniently used for the CMI in vitro assays. In addition, recombinant LFn homologues, variants and fragments can be prepared for use to detect or monitor a CMI response against a fused target antigen and for assessing LFn homologues, fusion proteins LFn mimetics and potential therapeutic agents. The preparation of recombinant LFn is described below.

A. General Recombinant DNA Methods: For producing recombinant proteins, routine techniques in the field of recombinant genetics can be used. Basic texts disclosing the general methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859 1862 (1981), using an automated synthesizer, as described in Van Devanter et. al., Nucleic Acids Res. 12:6159 6168 (1984). Purification of oligonucleotides can be, e.g., by either native acrylamide gel electrophoresis or by anion-exchange HPLC as described in Pearson & Reanier, J. Chrom. 255:137 149 (1983).

The sequence of the cloned genes and synthetic oligonucleotides can be verified after cloning using, e.g., the chain termination method for sequencing double-stranded templates of Wallace et al. Gene 16:21 26 (1981).

B. Cloning Methods for the Isolation of Nucleotide Sequences Encoding LF polypeptides, e.g., LFn: In general, the nucleic acid sequences encoding LFn and related nucleic acid sequence homologues are cloned from cDNA and genomic DNA libraries or isolated using amplification techniques with oligonucleotide primers. For example, LFn sequences are typically isolated from nucleic acid (genomic or cDNA) libraries.

Amplification techniques using primers can also be used to amplify and isolate LFn from DNA or RNA (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of LF directly from mRNA, from cDNA, from genomic libraries or cDNA libraries, and from plasmids. Degenerate oligonucleotides can be used to amplify homologues. These primers can be used, e.g., to amplify a probe of several hundred nucleotides, which can then be used to screen a library for full-length LF, which can be then be used to generate LFn. Alternatively, the nucleic acid for LFn can be directly amplified.

Nucleic acids encoding LFn can also be isolated from expression libraries using antibodies as probes. Synthetic oligonucleotides can be used to construct recombinant LFn genes for use as probes, for expression of protein, and for construction of polymorphic variants or mutants such as deletion mutants. This method is performed using a series of overlapping oligonucleotides, usually 40-120 by in length, representing both the sense and antisense strands of the gene. These DNA fragments are then annealed, ligated and cloned.

Polymorphic variants, alleles, and interspecies homologues that are substantially identical to LFn can be isolated using LFn nucleic acid probes and oligonucleotides under stringent hybridization conditions, by screening libraries using probes, or using amplification techniques as described above. Alternatively, expression libraries can be used to clone polymorphic variant, alleles, and interspecies homologues, by detecting expressed homologues immunologically with antisera or purified antibodies, which also recognize and selectively bind to the homologue.

The gene encoding LF has been cloned and sequenced, and has been assigned Genebank accession no. M29081 (Robertson & Leppla, Gene 44:71 78 (1986); Bragg & Robertson, Gene 81:45 54 (1989); see also U.S. Pat. Nos. 5,591,631, 5,677,274; see generally Leppla, Anthrax Toxins, in Bacterial Toxins and Virulence Factors in Disease (Moss et al., eds., 1995)).

The nucleic acids of interest are typically cloned into intermediate vectors before transformation into prokaryotic or eukaryotic cells for replication and/or expression. These intermediate vectors are typically prokaryote vectors, e.g., plasmids, or shuttle vectors, as described below.

C. Expression in Prokaryotes and Eukaryotes: To obtain high level expression of a cloned gene, such as those cDNAs encoding LFn, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the LFn protein are available in, e.g., *E. coli, Bacillus* sp., and *Salmonella* (Palva et al., Gene 22:229 235 (1983); Mosbach et al., Nature 302:543 545 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application and is not critical. Exemplary promoters include the SV40 early promoter, SV40 later promoter, metallothionein promoter, murine mammary tumor virus promoter, Rous sarcoma virus promoter, polyhedrin promoter, or other promoters shown effective for expression in eukaryotic cells, as well as prokaryotic promoters. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus also contains signals required for efficient polyadenylation of the transcript, ribosome binding sites, and translation termination. The nucleic acid sequence encoding the gene of choice may typically be led to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of Heliothis virescens. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Additional elements that are typically included in expression vectors also include a replicon that functions in *E. coli*, a gene encoding antibiotic resistance to permit selection of bacteria that harbor recombinant plasmids, unique restriction sites in nonessential regions of the plasmid to allow insertion of eukaryotic sequences. In addition, some expression systems have markers that provide gene amplification such as thymidine kinase, hygromycin B phosphotransferase, and dihydrofolate reductase. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Other exemplary eukaryotic vectors include pMSG, pAV009/A$^+$, pMTO10/A$^+$, and pMAMneo-5. Tags can also be added to recombinant proteins to provide convenient methods of isolation, e.g., c-Myc, or hexahistidine.

Standard transfection methods are used to produce, e.g., bacterial, mammalian, or yeast cell lines that express large quantities of LFn protein, which are then purified using standard techniques (see.e.g. Colley et al. J. Biol. Chem. 264: 17619 17622 (1989); Guide to Protein Purification, in Methods in Enzymology, vol. 182 (Deutscher, ed., 1990)). Transformation of eukaryotic and prokaryotic cells are performed according to standard techniques, e.g., calcium phosphate transfection, polybrene, protoplast fusion, electroporation, liposomes, microinjection, plasma vectors, viral vectors (see, e.g., Morrison, J. Bact. 132:349 351 (1977); Clark-Curtiss & Curtiss, Methods in Enzymology 101:347 362 (Wu et al., eds, 1983).

After the expression vector is introduced into the cells, the transfected cells are cultured under conditions favoring expression of the gene of choice, which is recovered from the culture using standard techniques identified below.

Purification of LF and Cellular Expression: LF polypeptides, e.g., LFn can be purified for use in the assays described herein. LFn polypeptides can be purified, e.g., from *B. anthracis* Sterne (Leppla, Production and Purification of Anthrax Toxin, Methods Enzymol, 165:103 116 (1988); Quinn et al., Biochem J. 252:753 758 (1988)). Recombinant LFn polypeptides can be purified from any suitable expression system. LFn polypeptides can be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al. supra).

A number of procedures can be employed when recombinant proteins are purified. For example, proteins having established molecular adhesion properties can be reversibly fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

A. Purification of Protein from Recombinant microorganisms:

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of recombinant inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Other suitable buffers are known to those skilled in the art. The protein of choice is separated from other bacterial proteins by standard separation techniques, e.g., with Ni-NTA agarose resin, where the protein is histidine tagged.

Alternatively, it is possible to purify the recombinant protein from bacteria periplasm. After lysis of the bacteria, when the recombinant protein is exported into the periplasm of the bacteria, the periplasmic fraction of the bacteria can be isolated by cold osmotic shock in addition to other methods known to skill in the art. To isolate recombinant proteins from the periplasm, the bacteria are centrifuged and the pellet is resuspended in ice-cold 5 mM $MgSO_4$ and kept in an ice bath for approximately 10 minutes, for cell lysis to occur. The cell suspension is centrifuged and the supernatant decanted and saved. The recombinant proteins present in the supernatant can be separated from the host proteins by standard separation techniques well known in the art.

B. Standard Protein Separation Techniques for Purifying Recombinant and Naturally Occurring Proteins Solubility Fractionation: Often as an initial step, particularly if the protein mixture is complex, an initial salt fractionation can separate many of the unwanted host cell proteins (or proteins derived from the cell culture media) from the protein of interest. The preferred salt is ammonium sulfate Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration: The molecular weight of the protein of choice can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography: The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, LFn can be purified using a PA63 heptamer affinity column (Singh et al., J. Biol. Chem. 269:29039 29046 (1994)).

Kits

The present invention also provides for kits for producing a composition which is useful for detecting or monitoring a CMI response against a desired target antigen, when the target antigen either expressed as a fusion protein with an LF polypeptide, e.g., an LFn polypeptide, or is otherwise conjugated to an LF polypeptide. Such kits can be prepared from readily available materials and reagents. For example, such kits can comprise any one or more of the following materials: biologically active LFn polypeptide, e.g., LFn polypeptide, reaction tubes, and instructions for testing LFn activity, and reagents for addition of the users preferred target antigen. A variety of kits and components can be prepared for use in the methods described herein, depending upon the intended use of the kit, the particular target antigen and the needs of the user.

Although the foregoing invention has been described in some detail by way of illustration and example for purposes of clarity of understanding it will be readily apparent to one of ordinary skill in the art in light of the teachings of this invention that certain changes and modifications may be made thereto without departing from the spirit or scope of the appended claims. The following is meant to be illustrative of the present invention; however, the practice of the invention is not limited or restricted in any way by the examples.

All publications and patent applications cited in this specification are herein incorporated by reference as if each individual publication or patent application were specifically and individually indicated to be incorporated by reference.

Some embodiments of the present invention may be defined in any of the following numbered paragraphs:

1. A method of measuring a cell mediated immune response (CMI) to a target antigen in a subject, the method comprising the steps of:
    a. incubating a biological sample from said subject with at least one fusion polypeptide, the fusion polypeptide comprising
    a portion of an LF polypeptide lacking LF enzymatic activity but sufficient to promote transmembrane delivery of said fusion polypeptide to a cell,
    said portion fused to a target antigen polypeptide or to a fragment thereof, wherein said biological sample comprises cells of the immune system that release at least one cytokine in response to an antigen;
    b. measuring the level of at least one cytokine released in said biological sample; and
    c. comparing the level of said cytokine in said biological sample with a reference level of the same cytokine,
    wherein an increase in the level of said cytokine in said biological sample from the subject as compared to the cytokine reference level indicates a cell mediated immune response (CMI) to the target antigen.

2. A method of detecting a pathology of interest in a subject, the method comprising the steps of:
   a. incubating a biological sample from said subject with at least one fusion polypeptide, the fusion polypeptide comprising
      a portion of an LF polypeptide lacking LF enzymatic activity but sufficient to promote transmembrane delivery of said fusion polypeptide to a cell,
      said portion fused to a target antigen polypeptide or to a fragment thereof, wherein the target antigen is expressed in a tissue affected by the pathology, and wherein said biological sample comprises cells of the immune system that release at least one cytokine in response to an antigen;
   b. measuring the level of at least one cytokine released in said biological sample; and
   c. comparing the level of said cytokine in said biological sample with a reference level of the same cytokine,
   wherein an increase in the level of said cytokine in said biological sample from the subject as compared to the cytokine reference level identifies the subject as having, or having an increased risk of having said pathology.
3. A method of measuring a cell mediated immune response (CMI) to a target antigen in a subject, the method comprising the steps of:
   a. incubating a biological sample from said subject with at least one target antigen, wherein said biological sample comprises cells of the immune system that release at least one cytokine following stimulation by the target antigen;
   b. measuring the presence or level of a cytokine released in said biological sample wherein the presence or level of the cytokine indicates the presence of a cell mediated immune response (CMI) to the target antigen in the biological sample from the subject.;
   wherein the improvement comprises, in incubating step (a), incubating the biological sample with at least one target antigen polypeptide or a fragment thereof fused to a portion of an LF polypeptide lacking LF enzymatic activity but sufficient to promote transmembrane delivery of said fusion polypeptide to a cell.
4. The method of any of paragraphs 1 to 3, wherein said portion of an LF polypeptide comprises at least the 60 carboxy-terminal amino acids of SEQ ID NO: 3, or a conservative substitution variant thereof that promotes transmembrane delivery.
5. The method of any one of paragraphs 1 to 4, wherein said portion of an LF polypeptide comprises at least the 80 carboxy-terminal amino acids of SEQ ID NO: 3, or a conservative substitution variant thereof that promotes transmembrane delivery.
6. The method of any one of paragraphs 1 to 5, wherein said portion of an LF polypeptide comprises at least the 104 carboxy-terminal amino acids of SEQ ID NO: 3, or a conservative substitution variant thereof that promotes transmembrane delivery.
7. The method of any of paragraphs 1 to 6, wherein the portion of an LF polypeptide comprises the amino acid sequence corresponding to SEQ ID NO: 3 or a conservative substitution variant thereof that promotes transmembrane delivery.
8. The method of any of paragraphs 1 to 7, wherein said portion of an LF polypeptide does not bind *B. anthracis* PA polypeptide.
9. The method of any one of paragraphs 1 to 3, wherein said portion of an LF polypeptide substantially lacks amino acids 1-33 of SEQ ID NO: 3.
10. The method of any one of paragraphs 1 to 3, wherein said portion of an LF polypeptide consists of SEQ ID NO: 4, or a conservative substitution variant thereof that promotes transmembrane delivery.
11. The method of any of paragraphs 1 to 10, wherein the target antigen polypeptide or a fragment thereof is at least 15 amino acids in length.
12. The method of any of paragraphs 1 to 11, wherein the target antigen polypeptide or a fragment thereof is folded in its native conformation.
13. The method of any of paragraphs 1 to 12, wherein the target antigen polypeptide or a fragment thereof is part of a multi-molecular polypeptide complex.
14. The method of any of paragraphs 1 to 13, wherein said target antigen polypeptide is a subunit polypeptide of a multi-molecular polypeptide target antigen.
15. The method any of paragraphs 1 to 13, wherein a fragment of said target antigen polypeptide is substantially one half the size of the full length target antigen.
16. The method of any of paragraphs 1 to 13, wherein a fragment of said target antigen polypeptide is substantially one third the size of the full length target antigen.
17. The method of any of paragraphs 1 to 13, wherein a fragment of said target antigen polypeptide is substantially one quarter of the size of the full length target antigen.
18. The method of any of paragraphs 1 to 13, wherein a fragment of said target antigen polypeptide is less than one quarter of the size of the full length target antigen and wherein said fragment is at least 15 amino acids in length.
19. The method of any of paragraphs 1 to 18, wherein the biological sample is a whole blood sample.
20. The method of any of paragraphs 1 to 18, wherein the biological sample is a plasma or lymph node biological sample.
21. The method of any one of paragraphs 1 to 20, wherein the immune cells are selected from one or more of: NK cells; T-cells; B-cells; Th cells; Th1 cells; Th2 cells; Tc cells; stromal cells; endothelial cells; leukocytes; lympocytes; fibroblasts; dendritic cells; macrophages; mast cells and monocytes.
22. The method of any one of paragraphs 1 to 21, wherein the immune cells are T-cells.
23. The method of any one of paragraphs 1 to 22, wherein the cytokine is selected from the group consisting of: GM-CSF; IL-1α; IL-1β; IL-2; IL-3; IL-4; IL-5; IL-6; IL-7; IL-8; IL-10; IL-12; IFN-α; IFN-β; IFN-β; MIP-1α; MIP-1β; TGF-β; TNFα and TNFβ.
24. The method of any one of paragraphs 1 to 23, wherein the cytokine is a T-cell cytokine selected from the group consisting of: IFN-g; TGFβ; TNFβ; IL-10; GM-CSF; IL-3; IL-4 and IL-5.
25. The method of any of paragraphs 1 to 24, wherein the cytokine is IFN-g.
26. The method or paragraph 2, wherein the pathology of interest is a pathogenic infection.
27. The method or paragraph 2, wherein the pathology of interest is cancer.
28. The method or paragraph 2, wherein the pathology of interest is an autoimmune disease.
29. The method of any of paragraphs 1 to 28, wherein the target antigen polypeptide or fragment thereof is an antigen of a pathogen.
30. The method of either of paragraphs 2 or 29, wherein the pathogen is selected from the group consisting of: Myocobacterium tuberculosis (TB), Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus and Simian Immunodeficiency virus.

31. The method of either of paragraphs 2 or 29, wherein the pathogen is Myocobacterium tuberculosis.
32. The method of any of paragraphs 1to 26 or 29 to 31, wherein the target antigen polypeptide is a TB-specific antigen.
33. The method of any of paragraphs 1 to 26 or 29 to 32, wherein the target antigen polypeptide is a TB1 (CFP) polypeptide comprising SEQ ID NO: 7 or a fragment thereof.
34. The method of any of paragraphs 1 to 26 to 29 or 32, wherein the target antigen polypeptide is TB2 (ESAT) polypeptide comprising SEQ ID NO: 6 or a fragment thereof.
35. The method of any of paragraphs 1 to 34, wherein the cytokine is measured at the level of protein expression.
36. The method of any one of paragraphs 1 to 35, wherein the cytokine is measured using an antibody, humanized antibody, antibody fragment, recombinant antibody, chimeric antibody, aptamer, peptide or analogue thereof.
37. The method of any one of paragraphs 1 to 35, wherein the cytokine is measured using a method selected from the group consisting of: an immunoassay, a radioimmunoassay (RIA), an immunoradiometric assay (IRMA), an enzyme-linked immunosorbent assay (ELISA); an ELISpot; CELISA (cellular enzyme-linked immunosorbent assay); a RHPA (reverse hemolytic plaque assay) or a kinase receptor activation assay (KIRA).
38. The method of any one of paragraphs 1 to 37, wherein the subject is a mammalian subject.
39. The method of any one of paragraphs 1 to 38, wherein the subject is a human subject.
40. The method of paragraph 34, wherein a fragment of said target antigen polypeptide is selected from the group consisting of: SEQ ID NO: 8 to SEQ ID NO: 29.
41. The method of paragraph 33, wherein a fragment of said target antigen polypeptide is selected from the group consisting of: SEQ ID NO: 30 to SEQ ID NO: 46.
42. The method of any of paragraphs 1-39, wherein said incubating comprises incubating said biological sample with a panel of fusion polypeptides comprising an LFn polypeptide fused to a target antigen polypeptide or fragment thereof, wherein the panel of fusion polypeptides comprises target antigen polypeptides or fragments thereof which substantially cover the entire full-length of the target antigen polypeptide.
43. The method of paragraph 42, wherein the panel of fusion polypeptides comprises a plurality of LFn polypeptides fused to a target antigen polypeptide or fragment thereof, wherein the target antigen polypeptide or fragments thereof are overlapping and/or adjacent target antigen polypeptide fragments which substantially cover the entire full-length of the target antigen polypeptide.
44. The method of either of paragraphs 42 or 43, wherein the panel of fusion polypeptides is at least 2 fusion polypeptides.
45. The method of either of paragraphs 42 or 43, wherein the panel of fusion polypeptides is at between 2 and 5 fusion polypeptides.
46. The method of either of paragraphs 42 or 43, wherein the panel of fusion polypeptides is at between 6 and 10 fusion polypeptides.
47. The method of either of paragraphs 42 or 43, wherein the panel of fusion polypeptides is at between 11 and 15 fusion polypeptides.
48. The method of either of paragraphs 42 or 43, wherein the panel of fusion polypeptides is at between 16 and 20 or more fusion polypeptides.
49. The method of any of paragraphs 42 to 48, wherein the panel of fusion polypeptides comprises at least two said LF polypeptides fused to different target antigen fragments selected from the group consisting of: SEQ ID NO: 8 to SEQ ID NO: 29.
50. The method of any of paragraphs 42 to 48, wherein the panel of fusion polypeptides comprises at least two said LF polypeptides fused to different target antigen fragments selected from the group consisting of: SEQ ID NO: 30 to SEQ ID NO: 46.
51. The method of either of paragraphs 1 or 3, wherein a CMI response identifies the subject to have, or be at risk of having a pathology.
52. The method of paragraph 51, wherein the pathology is selected from the group consisting of: a pathological infection; a cancer; an infectious disease; and an autoimmune disease.
53. The method of either of paragraphs 1 or 3, wherein a CMI response identifies the subject as likely to have been exposed to said target antigen, or a pathogen which expresses said target antigen.
54. The method of either of paragraphs 1 or 3, wherein a CMI response identifies the subject to have, or be likely to have a better prognosis as compared to a subject who is identified to have a low or negative ability to elicit a CMI response.
55. A method for monitoring a pathology of interest in a subject, the method comprising assessing the ability of a subject to elicit a cell mediated immune (CMI) response to a target antigen, wherein the method comprises;
   a. incubating a biological sample collected from the subject at a test timepoint with a polypeptide comprising a portion of a LF polypeptide lacking LF enzymatic activity but sufficient to promote transmembrane delivery of said fusion polypeptide to a cell, said polypeptide fused to a target antigen polypeptide or fragment thereof, wherein the target antigen is expressed in a tissue affected by said pathology, and wherein said biological sample comprises cells of the immune system that release at least one cytokine in response to an antigen;
   b. measuring the level of at least one cytokine released in said biological sample; and
   c. comparing the level of said cytokine in said biological sample with a reference level of the same cytokine,
wherein if an increase in the level of said cytokine in said biological sample obtained from the subject at the test timepoint is detected as compared to the reference level of said cytokine, then the subject is identified as having the ability to elicit a cell mediated immune (CMI) response to said target antigen polypeptide or fragment thereof.

56. The method of paragraph 55, wherein the reference cytokine level is the level of the cytokine from at least one, or a plurality of biological samples obtained from subjects not affected by said pathology.
57. The method of either of paragraphs 55 or 56, wherein the reference cytokine level is the level of the cytokine from a biological sample obtained from the subject at an earlier timepoint than said test timepoint.
58. The method of paragraph 55, further comprising treating a subject identified to have an ability to elicit a cell mediated (CMI) response with a suitable therapeutic protocol.
59. The method of paragraph 55, further comprising directing the treatment of a subject identified have an ability to elicit a cell mediated (CMI) response, wherein a practitioner reviews the levels of the cytokines, and if the subject is identified to have an ability to elicit a cell mediated (CMI) response, the practitioner directs the subject to be treated with a suitable therapeutic protocol.
60. The method of paragraph 55, further comprising predicting prognosis of the pathology in the subject, wherein if the subject is identified to have an ability to elicit a cell mediated (CMI) response, the subject is identified as likely to have a better prognosis as compared to a subject who is identified to have a low or negative ability to elicit a CMI response.
61. The method of paragraph 55, further comprising predicting risk of the subject developing the pathology, wherein if the subject is identified to have an ability to elicit a cell mediated (CMI) response, the subject is identified as less likely to develop the pathology as compared to a subject who is identified to have a low or negative ability to elicit a CMI response.
62. The method of any of paragraphs 55 to 61, wherein the pathology of interest is a pathogenic infection.
63. The method of any of paragraphs 55 to 61, wherein the pathology of interest is cancer.
64. The method of any of paragraphs 55 to 61, wherein the pathology of interest is an autoimmune disease.
65. The method of any of paragraph 55 to 64, wherein said portion of a LF polypeptide comprises at least the 80 carboxy-terminal amino acids of SEQ ID NO: 3, or a conservative substitution variant thereof that promotes transmembrane delivery.
66. The method of any of paragraphs 55 to 65, wherein said portion any of a LF polypeptide comprises at least the 80 carboxy-terminal amino acids of SEQ ID NO: 3, or a conservative substitution variant thereof that promotes transmembrane delivery.
67. The method of any of paragraphs 55 to 66, wherein said portion of a LF polypeptide comprises at least the 104 carboxy-terminal amino acids of SEQ ID NO: 3, or a conservative substitution variant thereof that promotes transmembrane delivery.
68. The method of any of paragraphs 55 to 67, wherein the portion of a LF polypeptide comprises the amino acid sequence corresponding to SEQ ID NO: 3 or a conservative substitution variant thereof that promotes transmembrane delivery.
69. The method of any of paragraphs 55 to 68, wherein said portion of a LF polypeptide does not bind B. anthracis PA polypeptide.
70. The method of any of paragraphs 55 to 69, wherein said portion of a LF polypeptide substantially lacks amino acids 1-33 of SEQ ID NO: 3.
71. The method of any of paragraphs 55 to 70, wherein said portion of a LF polypeptide consists of SEQ ID NO: 4, or a conservative substitution variant thereof that promotes transmembrane delivery.
72. The method of any of paragraphs 55 to 71, wherein the target antigen polypeptide or fragment thereof is at least 15 amino acids in length.
73. The method of any of paragraph 55 to 72, wherein the target antigen polypeptide or fragment thereof is folded in its native conformation.
74. The method of any of paragraphs 55 to 73, wherein the target antigen is part of a multi-molecular polypeptide complex.
75. The method of any of paragraphs 55 to 74, wherein the fragment of said target antigen polypeptide is a subunit polypeptide of a multi-molecular polypeptide target antigen.
76. The method of any of paragraphs 55 to 75, wherein the fragment of said target antigen polypeptide is substantially one half the size of the full length target antigen.
77. The method of any of paragraphs 55 to 75, the fragment of said target antigen polypeptide is substantially one third the size of the full length target antigen.
78. The method of any of paragraphs 55 to 75, wherein the fragment of said target antigen polypeptide is substantially one quarter of the size of the full length target antigen.
79. The method of any of paragraphs 55 to 75, wherein the fragment of said target antigen polypeptide is less than one quarter of the size of the full length target antigen and wherein a non-peptide fragment of a target antigen is at least 20 amino acids.
80. The method of any of paragraphs 55 to 79, wherein the biological sample is a whole blood sample.
81. The method of any of paragraphs 55 to 80, wherein the biological sample is a plasma or lymph node biological sample.
82. The method of any of paragraphs 55 to 81, wherein the immune cells are selected from one or more of: NK cells, T-cells, B-cells, Th cells, Th1 cells, Th2 cells, Tc cells, stromal cells, endothelial cells, leukocytes, lympocytes, fibroblasts, dendritic cells, macrophages, mast cells and monocytes.
83. The method of any of paragraphs 55 to 82, wherein the immune cell is a T-cell.
84. The method of any of paragraphs 55 to 83, wherein the cytokine is selected from the group consisting of: GM-CSF; IL-1α; IL-1β; IL-2; IL-3; IL-4; IL-5; IL-6; IL-7; IL-8; IL-10; IL-12; IFN-α; IFN-β; IFN-g, MIP-1α, MIP-1β, TGF-β, TNFα and TNFβ.
85. The method of any of paragraphs 55 to 84, wherein the cytokine is a T-cell cytokine selected from the group consisting of: IFN-g, TGFβ, TNFβ, IL-10, GM-CSF, IL-3, IL-4 and IL-5.
86. The method of any of paragraphs 55 to 85, wherein the cytokine is IFN-g.
87. The method of any of paragraphs 55 to 86, wherein the target antigen polypeptide or fragment thereof is an antigen of a pathogen.
88. The method of paragraph 87, wherein the pathogen is selected from the group consisting of: Myocobacterium tuberculosis (TB), Herpes simplex virus type-1, Herpes simplex virus type-2, HBV, Cytomegalovirus, Epstein-Barr virus, Varicella-zoster virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Human T-cell Leukemia virus type-1, Hantavirus, Rubella virus and Simian Immunodeficiency virus.

89. The method of paragraph 87, wherein the pathogen is Myocobacterium tuberculosis.

90. The method of any of paragraphs 55 to 62 or 65 to 87, wherein the target antigen is a TB-specific antigen.

91. The method of any of paragraphs 55 to 62 or 65 to 87, wherein the target antigen is a TB1 (CFP) polypeptide or a fragment thereof.

92. The method of any of paragraphs 55 to 62 or 65 to 87, wherein the target antigen is TB2 (ESAT) polypeptide or a fragment thereof.

93. The method of any of the paragraphs 55 to 92, wherein the cytokine is measured at the level of protein expression.

94. The method of any of paragraphs 1 to 83, wherein the cytokine is measured using an antibody, humanized antibody, antibody fragment, recombinant antibody, chimeric antibody, aptamer, peptide or analogue thereof.

95. The method of any of paragraphs 55 to 94, wherein the cytokine is measured using a methods selected from the group consisting of: an immunoassay, a radioimmunoassay (RIA), an immunoradiometric assay (IRMA), an enzyme-linked immunosorbent assay (ELISA); an ELISpot; a CELISA [cellular enzyme-linked immunosorbent assay; a RHPA (reverse hemolytic plaque assay) or a kinase receptor activation assay (KIRA).

96. The method of any of paragraphs 55 to 95, wherein the subject is a mammalian subject.

97. The method of any of paragraphs 55 to 96, wherein the subject is a human subject.

98. A kit for measuring a cell mediated immune (CMI) response to a target antigen polypeptide in a biological sample from a subject, the kit comprising a fusion polypeptide comprising a portion of a LF polypeptide lacking LF enzymatic activity but sufficient to promote transmembrane delivery of said fusion polypeptide to a cell, fused to a target antigen polypeptide or fragment thereof.

99. The kit of paragraph 98 wherein said portion of a LF polypeptide comprises at least the 60 carboxy-terminal amino acids of SEQ ID NO: 3, or a conservative substitution variant thereof that promotes transmembrane delivery.

100. The kit of any one of paragraphs 98 or 99, wherein said portion of a LFn polypeptide comprises at least the 80 carboxy-terminal amino acids of SEQ ID NO: 3, or a conservative substitution variant thereof that promotes transmembrane delivery.

101. The kit of any one of paragraphs 98 to 100, wherein said portion of a LFn polypeptide comprises at least the 104 carboxy-terminal amino acids of SEQ ID NO: 3, or a conservative substitution variant thereof that promotes transmembrane delivery.

102. The kit of any of paragraphs 98 to 101, wherein the portion of a LFn polypeptide comprises the amino acid sequence corresponding to SEQ ID NO: 3 or a conservative substitution variant thereof that promotes transmembrane delivery.

103. The kit of any one of paragraphs 98 to 102, wherein the kit comprises a panel of said fusion polypeptides, wherein said panel of fusion polypeptides is comprised of substantially contiguous target antigen fragments which together substantially cover the full-length of the target antigen polypeptide.

104. The kit of paragraph 103, wherein the panel of fusion polypeptides is at least 2 fusion polypeptides.

105. The kit of paragraph 103, wherein the panel of fusion polypeptides is at between 2 and 5 fusion polypeptides.

106. The kit of paragraph 103, wherein the panel of fusion polypeptides is at between 6 and 10 fusion polypeptides.

107. The kit of paragraph 103, wherein the panel of fusion polypeptides is at between 11 and 15 fusion polypeptides.

108. The kit of paragraph 103, wherein the panel of fusion polypeptides is at between 16 and 20 or more fusion polypeptides.

109. The kit of paragraph 103, wherein the panel of fusion polypeptides comprises at least two said fusion polypeptides, comprising different target antigen polypeptide fragments, said fragments selected from the group consisting of: SEQ ID NO: 8 to SEQ ID NO: 29.

110. The kit of paragraph 103, wherein the panel of fusion polypeptides comprises at least two said fusion polypeptides, comprising different target antigen polypeptide fragments said fragments selected from the group consisting of: SEQ ID NO: 30 to SEQ ID NO: 46.

111. A kit for measuring a cell mediated immune (CMI) response to a target antigen polypeptide in a biological sample from a subject, the kit comprising:
   a. a portion of a LF polypeptide lacking LF enzymatic activity but sufficient to promote transmembrane delivery of said fusion polypeptide to a cell;
   b. reagents to conjugate the portion of a LF polypeptide to a target antigen polypeptide or fragment thereof; and
   c. antibody-based detection means to detect at least one cytokine released from the biological sample.

112. A kit for measuring a cell mediated immune (CMI) response to a TB antigen polypeptide of a biological sample from a subject, the kit comprising:
   (a) a portion of a LF polypeptide lacking LF enzymatic activity but sufficient to promote transmembrane delivery of said fusion polypeptide to a cell, fused to a TB-specific antigen polypeptide; and
   (b) antibody-based detection means to detect at least one cytokine released from the biological sample.

113. The kit of any of paragraphs 98 to 112, optionally further comprising positive and negative biological sample controls, wherein a positive sample elicits a CMI response to the target antigen, and a negative biological sample elicits no CMI response.

114. The kit of paragraph 112, wherein the TB-specific antigen polypeptide is TB1 (CFP) polypeptide of SEQ ID NO: 7 or a fragment thereof.

115. The kit of paragraph 112, wherein the target antigen polypeptide is TB2 (ESAT) polypeptide of SEQ ID NO: 6 or a fragment thereof.

116. The kit of any of paragraphs 98, 106, or 112, wherein the fragment of said target antigen polypeptide is selected from the group consisting of; SEQ ID NO: 8 to SEQ ID NO: 29.

117. The kit of any of paragraphs 98, 106, or 112, wherein the fragment of said target antigen polypeptide is selected from the group consisting of; SEQ ID NO: 30 to SEQ ID NO: 46.

EXAMPLES

Materials and Methods

Blood Stimulation Procedure:

Blood sample. Blood is withdrawn from the subject to be tested with the diagnostic assay as disclosed herein. Typically enough blood is obtained from the subject for 1 ml per treatment, and is subject to heparin as anti-coagulant treatment. Samples should generally be used for the assay within 16 hours.

Blood stimulation. Typically this is performed in a Biosafety hood/a regular hood with UV light. After sterilization of the area, an 10 µl aliquot of TB stimulator 1 & 2 is added into a 3 ml tube using suitable size pipette, according to the following volumes; PBS—20 µl, ConA (5 mg/ml)—20 µl, CFP (0.8 ug/ml)—10 µl and ESAT (0.8 ug/ml)—20 µl. Next, 1 ml of the sample to be tested (i.e. 1 ml of blood) is added into the same tube, the tube is capped and placed into a tube holder.

Blood incubation. The tube is mixed by being shaken vigorously for at least 5 seconds until frothing appears. The tubes are then immediately incubated in an upright position at 37° C., typically using a water bath. If the tubes cannot be immediately incubated at 37° C. they must be vigorously mixed again. The samples are incubated at 37° C. for 24 hrs. Following this incubation, the blood is decanted into a 1.5 ml tube and centrifuged at 10,000-13,000 RPM for 5 minutes. The supernatant is transferred into a new tube and centrifuged for a second time at 10,000-13,000 RPM for 5 minutes. If more blood cells are pelleted, transfer supernatant into new tube and re-centrifuge for a third time at 10,000-13,000 RPM for 5 minutes. Following removal of the blood cells, the supernatant can be stored at −20° C. or kept at 4° C. for at least 2 weeks before being assayed for cytokines, e.g., IFN-γ.

IFN-γ ELISA:

Solution and reagent preparation. The following reagents and solutions are useful in the methods of performing an IFN-γ ELISA:

Capture antibody: 1 mg/ml, Human IFN-γ MAb: Cat # M700A, from Thermo-Fisher/Pierce.

Detection antibody: 0.5 mg/ml, Human IFN-γ MAb-Biotin: Cat # M701B, from Thermo-Fisher/Pierce.

10× Coating solution: $Na_2CO_3$ (16 g), $NaHCO_3$ (29.3 g), Thimerosal (1 g), adjust volume to 1 L, adjust pH to 9.6, 0.22 µm filter sterilize, keep at 4° C. Dilute to 1× before use: 10× PBS, NaCl (80 g), KCL (2 g), $Na_2HPO_4·12 H_2O$ (14.4 g), $KH_2PO_4$ (2.4 g), Thimerosal (1 g), QS to 1 L, adjust pH to 7.4, 0.22 µm filter sterilize.

1×PBST: 0.05% Tween in PBS, 0.22 um filter sterilize

Blocking solution: 2% BSA, 2% FBS, 0.01% thimerosal in PBS, 0.22 µm filtered. BSA (20 g), FBS (20 ml), Thimerosal (1 g) adjust volume to 1 L, 0.22 µm filter sterilize.

Stopping solution ($2M H_2SO_4$): Slowly add 55.5 ml $H_2SO_4$ (95-98%) into $H_2O$, adjust volume to 500 ml.

Standard curve Stock solutions (IFN-γ): IFN-γ (50 ug/bottle, Cat# RIFNG50, Pierce). Stock IFN-γ solution (100 µg/ml IFNg): Add 500 µl PBS into 5Oug IFN-γ to get 100 µg/ml, then aliquot into 5 tubes (100 µl/tube) and store at −70° C. Working solution (1 µg/ml IFNg): Add 10 µl of the stock IFN-γ into 990 µl assay diluent to get 1 ug/ml of IFN-γ. Store at 4° C.

Standard curve preparation: Add 2.4 µl of IFN-γ (1 µg/ml) into 1 ml assay diluent for a 2.4 ng/ml solution. Aliquot 500 µl of 2.4 ng/ml into 500 µl assay diluent for a 1.2 ng/ml solution. Aliquot t 500 µl of 1.2 ng/ml into 500 µl assay diluent for 600 pg/ml. Aliquot 500 µl of 600 pg/ml into 500 µl assay diluent for 300 pg/ml, etc. . . . Typically, a standard curve can be the following dilutions: 600 pg/ml, 300 pg/ml, 150 pg/ml, 75 pg/ml, 37.5 pg/ml, 18.8 pg/ml, 9.4 pg/ml.

S-HRP preparation: S-HRP working solution: Add 5 ul of S-HRP to 5 ml HRP Stabilizer (Guardian Peroxidase Conjugate Stabilizer/Diluent, Cat# 37548, Pierce) to get 1:1000 dilution, keep at 4° C.

TMB solution: Solution A: Solution B=1:1

Example 1

IFN-γ ELISA Procedure. As an example, the following describes the procedure for 1 plate (96 wells), with calculations based on 100 wells.

Coating: 10 µl of capture antibody (stock 1 mg/ml) is added to 10 ml of coating solution in order to dilute the capture antibody to 1 ug/ml. 100 µl of capture antibody at 1 µg/ml added to each well of a 96 well plate and incubated at 4° C. overnight. Following this incubation at 4° C., the capture antibody is aspirated from the wells, and the wells washed with 250 µl PBST/well at least three times, preferably 5 times. Following the washing steps, the wells are blocked, using 250 µl blocking buffer in each well for 2 hrs at 37° C.

Washing step: The blocking solution is aspirated from the wells, followed by addition of 250 µl PBST/well. This process is repeated for at least 3 times, preferably 5 times.

Sampling step: 100 µl IFN-γ of each of the standard curve dilutions (i.e. from 300 pg/ml to 4.7 pg/ml, see "Standard curve preparation (IFN-γ)" for details) are added into separate wells. A volume of each sample to be tested is added to the free wells (i.e. the wells not containing the standard curve solutions). Typically, the volume of each sample is 100 µl. In some instances, the sample can be diluted before adding to the well, for example diluted 1:2, or 1:5, or 1:7 or 1:10, or 1:20, or 1:50, or 1:100 or 1:1000 or more. The samples and the standard curve solutions are incubated in the wells for at least 1hr at 37° C.

Washing step: The blocking solution is aspirated from the wells, followed by addition of 250 µl PBST/well. This process is repeated for at least 3 times, preferably 5 times.

Detection step: A 50 ng/ml detection antibody solution is prepared by adding 10 µl of the detection antibody (50 ug/ml by 1:10 dilution of the stock) to 10 ml assay diluent. After aspiration of the last wash solution, 100 µl/well of the detection antibody (at 50 ng/ml) is added to each well and incubated for at least 30 minutes at 37° C. Following the incubation, this step is followed by a washing step as follows: Washing step: The blocking solution is aspirated from the wells, followed by addition of 250 µl PBST/well. This process is repeated for at least 3 times, preferably 5 times.

S-HRP step: A 1:32,000 diluted solution of S-HRP is prepared by adding 313 µl of HRP working solution to 10 ml assay. Following aspiration of the last wash step, 100 µl of the 1:32,000 S-HRP is added into each well and incubated for at least 30 minutes at 37° C. Following the incubation, this step is followed by a washing step as follows: Washing step: The blocking solution is aspirated from the wells, followed by addition of 250 µl PBST/well. This process is repeated for at least 3 times, preferably 5 times.

TMB substrate solution: A TMB substrate solution is prepared by adding equal volumes of solution A to solution B for a 1:1 A:B working solution. Typically, 5 ml of solution A is added to 5 ml solution B. 100 µl/well of the A:B solution is added to each well and incubated at 37° C. for at least 10 minutes. During this period, the solution and samples are protected from direct exposure to intense light (for example, the plate is wrapped in foil or a light blocking material).

Stopping: Following the incubation of the samples with the A:B solution, the reaction is stopped by the addition of 100µl stopping solution to each well.

Reading: The analysis of the results of the ELISA is performed by reading the plate at 450 nm wavelength. Detection of IFN-γ is indicative of a CMI response to the target antigen in the individual from whom the sample was isolated. The amount of IFN-γ can be normalized to a reference, including, for example, IFN-γ measured in a blood sample from the same individual, that sample incubated in the absence of the LF polypeptide-target antigen fusion protein, and/or the IFN-γ measured in a standard taken from one or more reference (e.g., healthy control) individuals, where the levels are measured either separately or in a pooled sample. Generally, a statistically significant difference in cytokine level, e.g., IFN-γ, is indicative of a positive result in the CMI response assay; however, for the avoidance of doubt, a statistically significant difference that is at least 10% greater, preferably at least 25%, 50%, 75%, 100%, 2-fold, 5-fold, 10-fold, or more, greater than a reference level is indicative of a positive result.

Example 2

Confirmation of TB smear test using CMI response assay in vitro. Samples from 13 patients identited to be positive for TB via TB smear test were assayed for CMI response to TB using the diagnostic test described herein. The 13 samples were also assayed for positivity for TB using the culture test. INF-γ levels were assayed using an ELISA after incubation with a LFn-TB antigen. The results are shown in Tables 3 and 4.

Table 3 shows an example of the results of the CMI assay as disclosed herein as a diagnostic and prognostic identification of subject with TB by measuring INF-γ levels using ELISA assay to determine the INFγ protein level.

| SAMPLE ID | Sputum smear positive | sputum culture positve | postive control | negative control | VTI test sample |
|---|---|---|---|---|---|
| HLJ T1217-1 | + | + | 0.085 | 1.496 | 1.920 |
| HLJ T1217-2 | + | + | 0.074 | 2.277 | 0.240 |
| HLJ T1217-3 | + | − | 0.109 | 3.342 | 2.809 |
| HLJ T1217-4 | + | − | 0.065 | 2.933 | 0.641 |
| HLJ T1217-5 | + | + | 0.082 | 3.483 | 2.628 |
| HLJ T1217-6 | + | − | 0.071 | 3.408 | 2.020 |
| HLJ T1217-7 | + | − | 0.083 | 0.684 | 0.110 |
| HLJ T1217-8 | + | − | 0.078 | 0.825 | 2.861 |
| HLJ T1217-9 | + | + | 0.106 | 3.406 | 2.678 |
| HLJ T1217-10 | + | − | 0.079 | 3.245 | 2.043 |
| HLJ T1217-11 | + | − | 0.070 | 2.798 | 0.581 |
| HLJ T1217-12 | + | + | 0.118 | 3.088 | 1.328 |
| HLJ T1217-13 | + | − | 0.071 | 3.281 | 3.340 |

Samples in bold were identified to be positive for TB using both the TB smear test and the TB culture test. In this example, the assay was preformed using re-blocking plate, lot #20081217, GMP INF-γ (lot 20081001) for standard curve -1 mg/ml, dectection Ab Pierce, lot#IJ116994. HRP: Biosource, lot#1412548A; TMB: TopBio, lot#T3465; Stopping buffer: 2MH2SO4, GMP, lot#20080901.

Table 4 shows an example of the results of the CMI assay as disclosed herein as a diagnostic and prognostic identification of subject with TB by measuring INF-γ levels using ELISA assay to determine the INF-γ protein level.

| SAMPLE ID | Sputum smear positive | sputum culture positve | postive control | negative control | VTI test sample |
|---|---|---|---|---|---|
| HLJ T1217-14 | + | + | 0.097 | 3.462 | 2.533 |
| HLJ T1218-1 | + | − | 0.122 | 3.077 | 2.499 |
| HLJ T1218-2 | − | + | 0.123 | 3.155 | 0.549 |
| HLJ T1218-3 | + | − | 0.250 | 0.370 | 2.887 |
| HLJ T1218-4 | + | − | 0.123 | 3.128 | 3.062 |
| HLJ T1218-5 | + | − | 0.130 | 2.674 | 2.806 |
| HLJ T1218-6 | + | − | 0.133 | 2.657 | 1.751 |
| HLJ T1219-1 | + | − | 0.225 | 3.139 | 2.749 |

Samples in bold were identified to be positive for TB using both the TB smear test and the TB culture test. In this example, the assay was preformed using re-blocking plate, lot#20081223; VTI IFN-γ: GMP IFN-γ, lot#20081001, 1 mg/ml; Detection Ab: Pierce, lot#IJ116994.; HRP: Biosource, lot#1412548A; TMB: TopBio, lot#T3465; Stopping buffer: 2MH2SO4, GMP, lot#20080901. The assay was read at 450 nm.

Example 3

Figure 15:
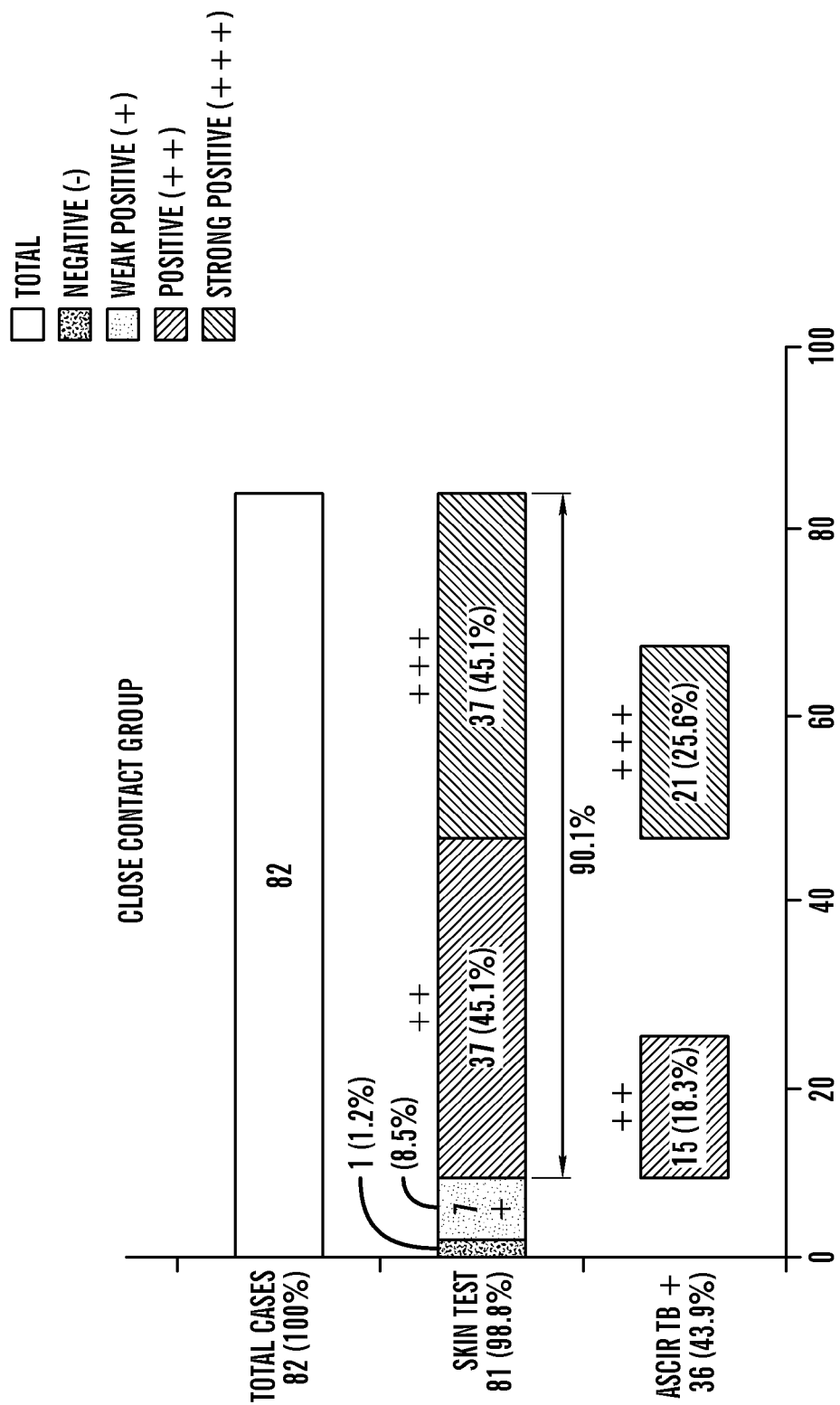
FIG. 15 shows the comparison of TB positive results of a total of 82 patients from the close contact group tested with either the skin test or the ASCIR TB test (VTI kit). Using the skin test, 90.1% of the subjects tested either positive (++) (45.1%) or strong positive (+++) (45.1%), whereas only 18.3% tested positive (++) and 25.6% tested strong positive (+++) with the ASCIR TB test.
Figure 16:
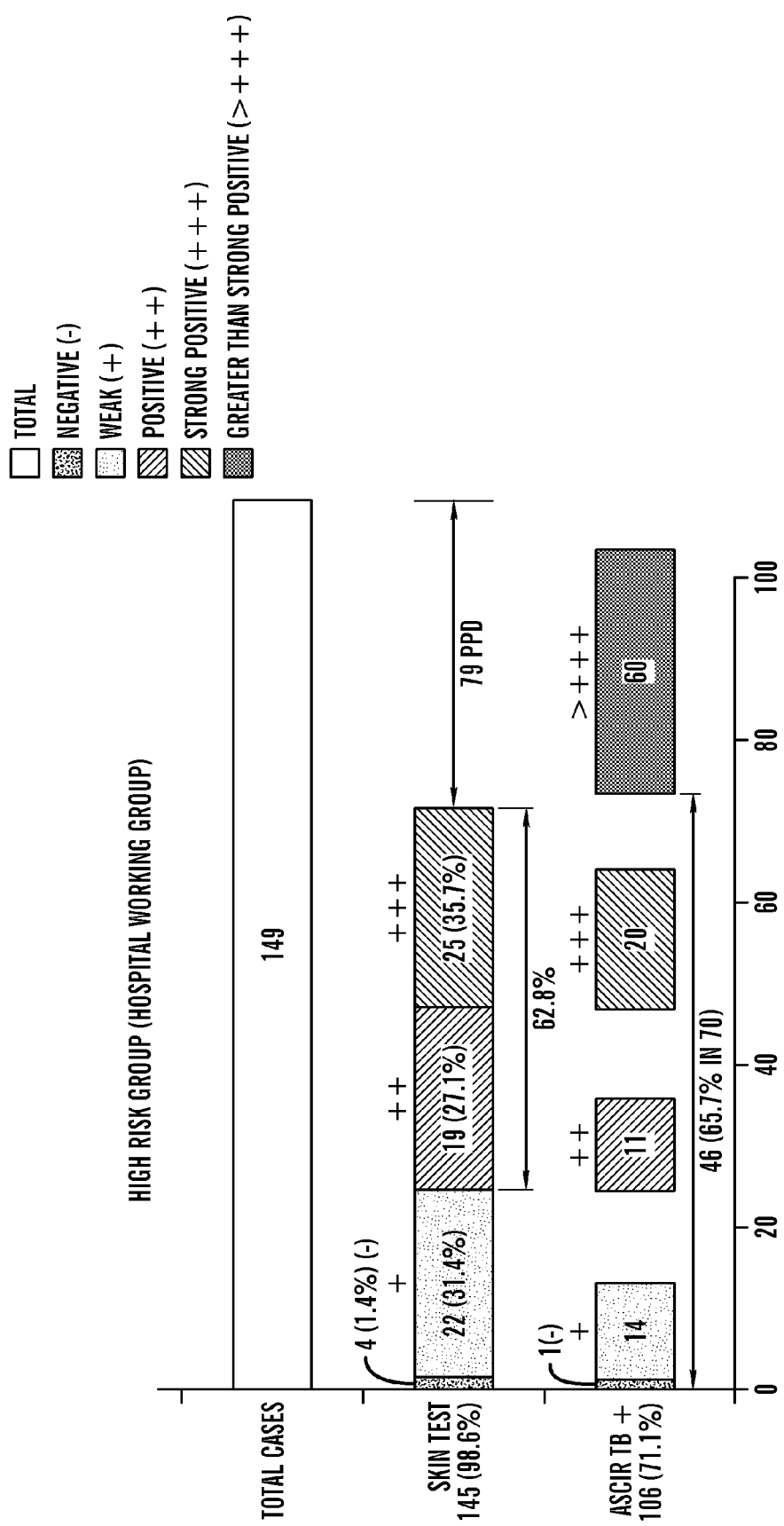
FIG. 16 shows the comparison of TB positive results of a total of 149 patients from the High Risk Group (of subjects working in the hospital) tested with either the skin test or the ASCIR TB test (VTI kit). Using the skin test, a total of 98.8% of subjects were TB positive, where 62.8% of the subjects tested either positive (++) (27.1%) or strong positive (+++) (35.7%) and 76 subjects had a greater than strong positive test. In comparison, 71.1% of the subjects were positive with the ASCIR TB test, with 11 subjects (7.4%) testing positive (++) and 20 subjects (13.4%) testing strong positive (+++) with the ASCIR TB test, with 60 subjects having a greater than strong positive test.

As demonstrated herein, the ASCIR TB Test is better at accurately determining a subject with TB as compared to conventional tests. For example, as shown in FIGS. 15-17, the ASCIR TB test reduces the false postives for TB subjects, as compared to skin tests. The tuberculosis skin test (also known as the tuberculin test or PPD test) is a test used to determine if someone has developed an immune response to the bacterium that causes tuberculosis (TB). This response can occur if someone currently has TB, if they were exposed to it in the past, (or if they received the BCG vaccine against TB, which is not performed in the U.S.). In the TB skin test performed in FIGS. 15-18, the PPD test restults were analysed according to the following scale: a skin reaction of between 0<5 mm is negative reaction, between 5 mm<10 mm is a weak positive reaction, between 10 mm<20 mm is a positive reaction, and >20 mm is a greater than strong reaction. Thus, the inventors demonstrated that the ASCIR TB test is more accurate in that it reduces the number of false postives identified as having TB.

For example, FIG. 15 compares the skin test and ASCIR test in a close contact group (e.g., subjects having come into close contact with TB patients), FIG. 16 compares the skin test with the ASCIR TB test a high risk group (e.g., subjects who work in hospitals who have had, or are at risk of contact with TB patients), and FIG. 17 compares the skin test with the ASCIR TB test in a group of college freshman (e.g., low risk group). In all groups examined, the ASCIR TB test resulted in fewer false postives.

Figure 17A:
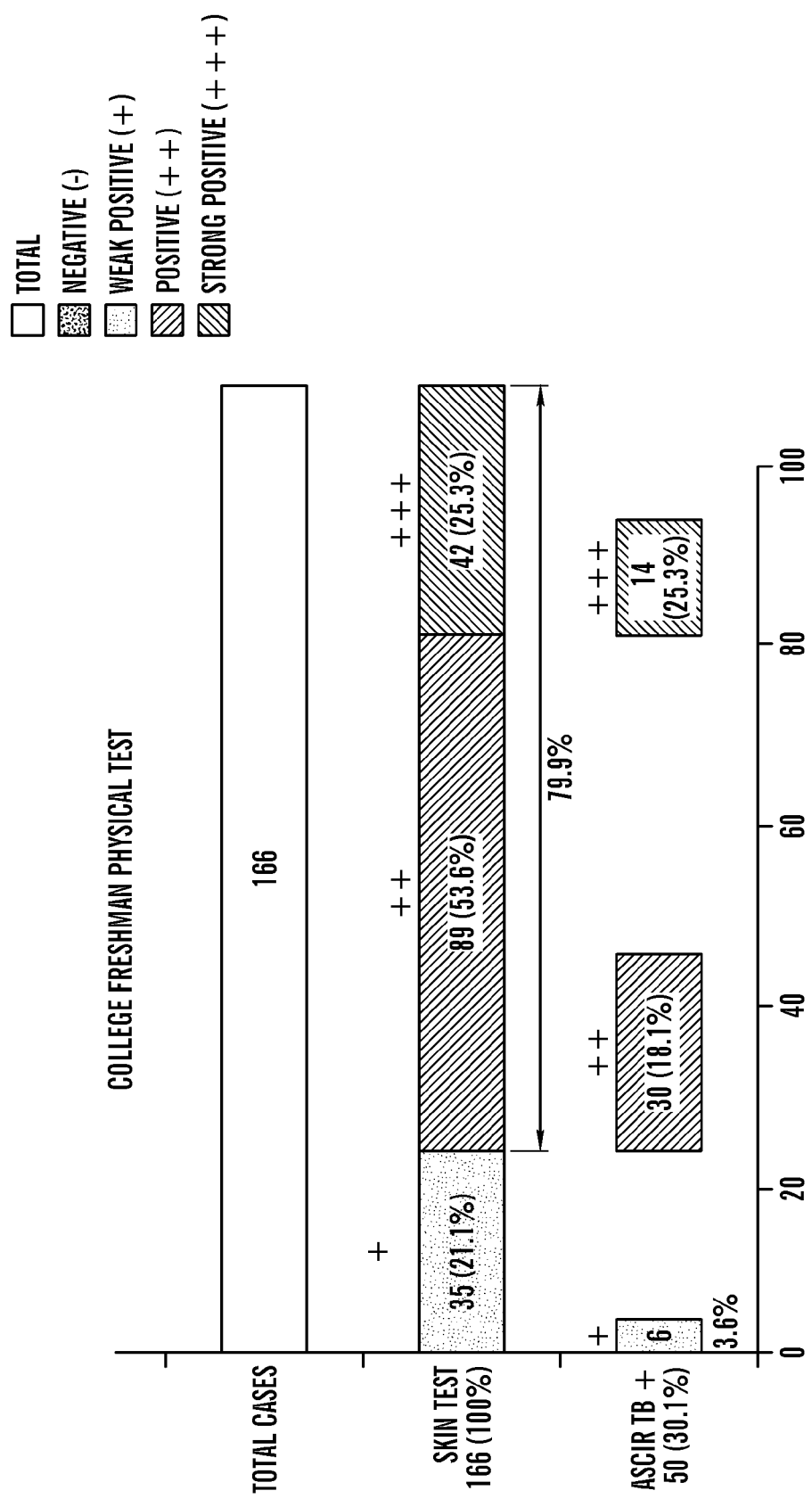
FIG. 17A-17B shows the comparison of TB positive results of a total of 166 subjects from the College Freshman Physical test which were tested with either the skin test or the ASCIR TB test (VTI kit).
Figure 17B:
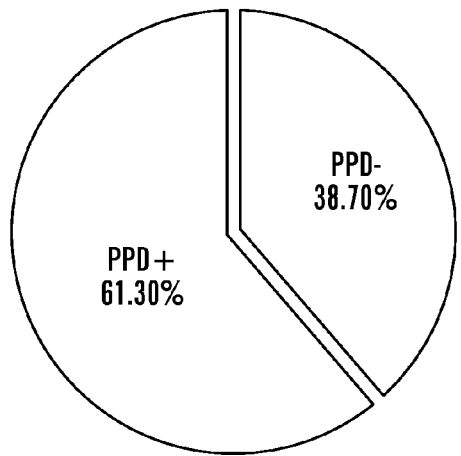

For example, analysis of the close contact group showed that 90.1% of the subjects tested either positive (++) (45.1%) or strong positive (+++) (45.1%) with the skin test, whereas only 18.3% tested positive (++) and 25.6% tested strong positive (+++) with the ASCIR TB test (FIG. 15). Analysis of the High Risk Group showed that 98.8% of subjects were TB positive with the skin test, with 62.8% positive (++) (27.1%) or strong positive (+++) (35.7%), whereas 71.1% of the subjects were positive with the ASCIR TB test, with 7.4% positive (++) and 13.4% strong positive (+++)(FIG. 16). In the analysis of the group of college freshman, 100% of the subjects were either weakly positive, positive or strong positive, with 79.9% positive (++)(53.6%) or strong positive (+++) (25.3%), whereas 30.1% of the subjects were positive with the ASCIR TB test, with 18.1% testing positive (++) and 25.3% testing strong positive (+++) with the ASCIR TB test (FIG. 17A). The inventors noted that of the total subjects tested in the College Freshman Physical test group, 38.7% of the subjects tested negative on the skin test (PPD1) (FIG. 17B). This demonstrates that the inventors test is more accurate and reduces the number of false postives as compared to the PPD skin test.

Figure 18:
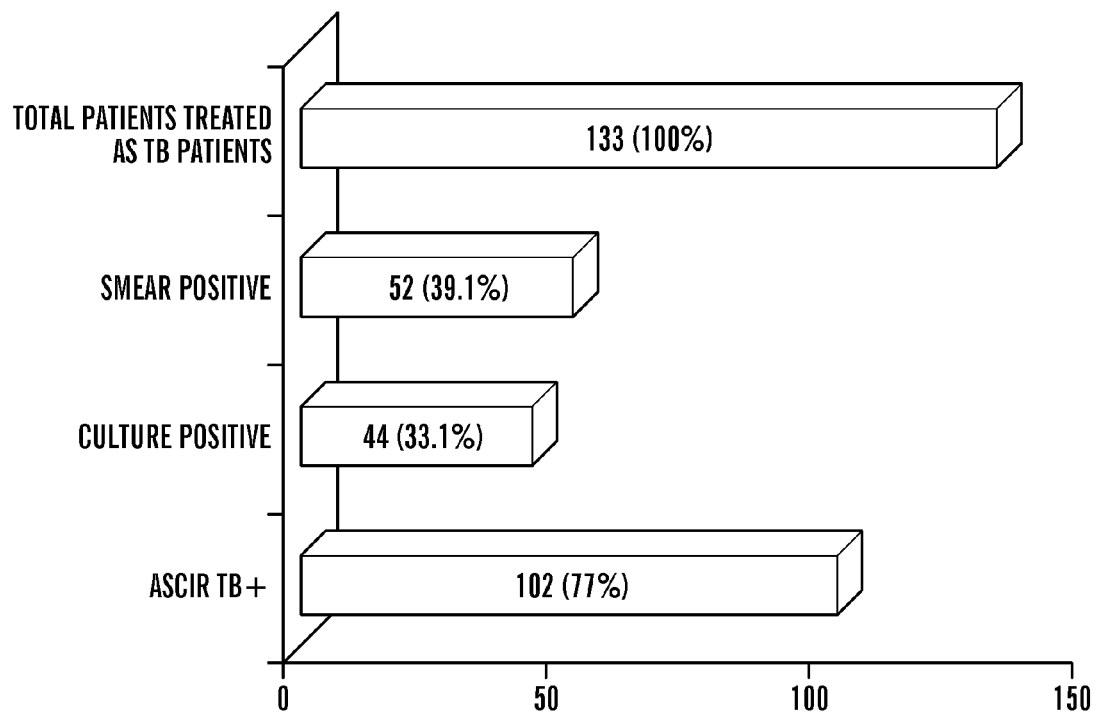
FIG. 18 shows a histogram of the comprison of TB patients tested with three different tests; smear test, culture positive test and ASCIR TB test. Of 133 subjects treated as TB patients, 52 (39.1%) were identified as being positive by the smear test, 44 (33.1%) were identified as being positive by the culture test, and 102 (77%) were identified as being positive by the ASCIR TB test as disclosed herein.

Additionally, the inventors demonstrated that of TB treated patients, the ASCIR TB test is more accurate than the smear test or the culture test and results in fewer false negatives. For example, as shown in FIG. 18, a comprison of patients (who have and are being treated for TB) were tested with the three different tests; smear test, culture positive test and ASCIR TB. A total of 102 subjects (77%) were identified as being positive by the ASCIR TB test, whereas only 52 subjects (39.1%) or 44 subjects (33.1%) were identified as being positive by the smear test or culture test, respectively. This demonstrates that the ASCIR TB test as disclosed herein is more accurate at reducing false negatives than the smear test or the skin test.

REFERENCES

All references and patent and patent applicaitons described herein in the specificaiton are incorporated herein in their entirety by reference.
1. Anderson, K. S., J. Alexander, M. Wei, and P. Cresswell 1993. Intracellular transport of class I MHC molecules in antigen processing mutant cell lines Journal of Immunology. 151:3407-19.
2. Androlewicz, M. J., K. S. Anderson, and P. Cresswell 1993. Evidence that transporters associated with antigen processing translocate a major histocompatibility complex class I-binding peptide into the endoplasmic reticulum in an ATP-dependent manner Proceedings of the National Academy of Sciences of the United States of America. 90:9130-4.
3. Ballard, J. D., A. M. Doling, K. Beauregard, R. J. Collier, and M. N. Starnbach 1998. Anthrax toxin-mediated delivery in vivo and in vitro of a cytotoxic T-lymphocyte epitope from ovalbumin Infection & Immunity. 66:615-9.
4. Borrow, P., H. Lewicki, B. H. Hahn, G. M. Shaw, and M. B. A. Oldstone 1994. Virus-specific CD8+ cytotoxic T-lymphocyte activity associated with control of viremia in primary human immunodeficiency virus type 1 infection J. Virol. 68:6103-6110.
5. Borrow, P., H. Lewicki, X. Wei, M. S. Horwitz, N. Peffer, H. Meyers, J. A. Nelson, J. E. Gairin, B. Hahn, M. B. Oldstone, and G. M. Shaw 1997. Antiviral pressure exerted by HIV-1-specific cytotoxic T lymphocytes (CTLs) during primary infection demonstrated by rapid selection of CTL escape virus Nature Medicine. 3:205-211.
6. Cao, H., P. Kanki, J.-L. Sankale, A. Dieng-Sarr, G. P. Mazzara, S. A. Kalams, B. Korber, S. MBoup, and B. D. Walker 1997. Cytotoxic T-lymphocyte cross-reactivity among different human immunodeficiency virus type 1 clades: implication for vaccine development J. Virol. 71:8615-23.
7. Cao, H., I. Mani, R. Vincent, R. Mugerwa, P. Mugyenyi, P. Kanki, J. Ellner, and B. D. Walker 2000. Cellular immunity to HIV-1 Clades: relevance to HIV-1 vaccine trials in Uganda J. Infec Dis. 182:1350-56.
8. Doling, A. M., J. D. Ballard, H. Shen, K. M. Krishna, R. Ahmed, R. J. Collier, and M. N. Starnbach 1999. Cytotoxic T-lymphocyte epitopes fused to anthrax toxin induce protective antiviral immunity Infection & Immunity. 67:3290-6.
9. Falk, K., O. Rotzchke, K. Deres, J. Metzger, G. Jung, and H.-G. Rammensee 1991. Identification of naturally processed viral nonapeptides allows their quantification in infected cells and suggests an allele-specific T cell epitope forecast. J. Exp. Med. 174:425-434.
10. Finbloom, D. S., J. Martin, and R. K. Gordon 1987. Endocytosis of particulate and soluble IgG immune complexes: differential effects of cytoskeletal modulating agents Clinical & Experimental Immunology. 67:205-10.
11. Geisow, M. J., P. D'Arcy Hart, and M. R. Young 1981. Temporal changes of lysosome and phagosome pH during phagolysosome formation in macrophages: studies by fluorescence spectroscopy Journal of Cell Biology. 89:645-52.
12. Goldberg, A. L., and K. L. Rock 1992. Proteolysis, proteasomes and antigen presentation Nature. 357:375-9.
13. Hanna, P. C., D. Acosta, and R. J. Collier 1993. On the role of macrophages in anthrax Proceedings of the National Academy of Sciences of the United States of America. 90:10198-201.
14. Harding, C. V., and R. Song 1994. Phagocytic processing of exogenous particulate antigens by macrophages for presentation by class I MHC molecules Journal of Immunology. 153:4925-33.
15. Howard, J. C. 1995. Supply and transport of peptides presented by class I MHC molecules Current Opinion in Immunology. 7:69-76.
16. Klaus, G. G. 1973. Cytochalasin B. Dissociation of pinocytosis and phagocytosis by peritoneal macrophages Experimental Eye Research. 79:73-8.
17. Koup, R. A., J. T. Safrit, Y. Cao, C. A. Andrews, G. McLeod, W. Borkowsky, C. Farthing, and D. D. Ho 1994. Temporal association of cellular immune responses with the initial control of viremia in primary human immunodeficiency virus type 1 syndrome J. Virol. 68:4650-4655.
18. Lalvani, A., R. Brookes, S. Hambleton, W. J. Britton, A. V. Hill, and A. J. McMichael 1997. Rapid effector function in CD8+ memory T cells Journal of Experimental Medicine. 186:859-65.
19. Lu, Y., R. Friedman, N. Kushner, A. Doling, L. Thomas, N. Touzjian, M. Starnbach, and J. Lieberman 2000. Genetically modified anthrax lethal toxin safely delivers whole HIV protein antigens into the cytosol to induce T cell immunity Proceedings of the National Academy of Sciences of the United States of America. 97:8027-32.
20. Man, S., R. D. Salter, and V. H. Engelhard 1992. Role of endogenous peptide in human alloreactive cytotoxic T cell responses International Immunology. 4:367-75.
21. Neefjes, J., F. Momberg, and G. Hammerling 1993. Selective and ATP-dependent translocation of peptides by the MHC-encoded transporter. Science. 261:769-771.
22. Ogg, G. S., X. Jin, S. Bonhoeffer, P. R. Dunbar, M. A. Nowak, S. Monard, J. P. Segal, Y. Cao, S. L. Rowland-Jones, v. Cerundolo, A. Hurley, M. Markowitz, D. D. Ho, D. F. Nixon, and A. J. McMichael 1998. Quantitation of HIV-1-specific cytotoxic T lymphocytes and plasma load of viral RNA Science. 279:2103-6.
23. Ohkuma, S., and B. Poole 1978. Fluorescence probe measurement of the intralysosomal pH in living cells and the perturbation of pH by various agents Proceedings of the National Academy of Sciences of the United States of America. 75:3327-31.
24. Ortmann, B., M. J. Androlewicz, and P. Cresswell 1994. MHC class I/beta 2-microglobulin complexes associate with TAP transporters before peptide binding Nature. 368:864-7.

25. Pfeifer, J. D., M. J. Wick, R. L. Roberts, K. Findlay, S. J. Normark, and C. V. Harding 1993. Phagocytic processing of bacterial antigens for class I MHC presentation to T cells Nature. 361:359-62.
26. Pinto, L. A., J. Sullivan, J. A. Berzofsky, M. Clerici, H. A. Kessler, A. L. Landay, and G. M. Shearer 1995. ENV-specific cytotoxic T lymphocyte responses in HIV seronegative health care workers occupationally exposed to HIV-contaminated body fluids J. Clin. Invest. 96:867-76.
27. Powis, S. J. 1997. Major histocompatibility complex class I molecules interact with both subunits of the transporter associated with antigen processing, TAP1 and TAP2 European Journal of Immunology. 27:2744-7.
28. Rowland-Jones, S., J. Sutton, K. Ariyoshi, T. Dong, F. Gotch, S. McAdam, D. Whitby, S. Sabally, A. Gallimore, T. Corrah, M. Takiguchi, T. Schultz, A. McMichael, and H. Whittle 1994. Resistance to HIV-1 infection- HIV-specific cytotoxic T lymphocytes in HIV-exposed but uninfected Gambian women Nature Medicine. in Press.
29. Sadasivan, B., P. J. Lehner, B. Ortmann, T. Spies, and P. Cresswell 1996. Roles for calreticulin and a novel glycoprotein, tapasin, in the interaction of MHC class I molecules with TAP Immunity. 5:103-14.
30. Solheim, J. C., M. R. Harris, C. S. Kindle, and T. H. Hansen 1997. Prominence of beta 2-microglobulin, class I heavy chain conformation, and tapasin in the interactions of class I heavy chain with calreticulin and the transporter associated with antigen processing Journal of Immunology. 158:2236-41.
31. Song, R., and C. V. Harding 1996. Roles of proteasomes, transporter for antigen presentation (TAP), and beta 2-microglobulin in the processing of bacterial or particulate antigens via an alternate class I MHC processing pathway Journal of Immunology. 156:4182-90.
32. Suh, W. K., M. F. Cohen-Doyle, K. Fruh, K. Wang, P. A. Peterson, and D. B. Williams 1994. Interaction of MHC class I molecules with the transporter associated with antigen processing Science. 264:1322-6.
33. Wei, M. L., and P. Cresswell 1992. HLA-A2 molecules in an antigen-processing mutant cell contain signal sequence-derived peptides. Nature. 356:443-6.
34. Yewdell, J. W., and J. R. Bennink 1989. Brefeldin A specifically inhibits presentation of protein antigens to cytotoxic T lymphocytes Science. 244:1072-5.

The invention claimed is:

1. A kit for measuring a cell mediated immune (CMI) response to a TB antigen polypeptide of a biological sample from a subject, the kit comprising:
   a. a panel of at least two fusion polypeptides wherein each fusion polypeptide comprises a portion of a LF polypeptide lacking LF enzymatic activity but sufficient to promote transmembrane delivery of said fusion polypeptide to a cell, fused to a TB-specific antigen polypeptide,
   wherein said portion of a LF polypeptide comprises at least the 60 carboxy-terminal amino acids of SEQ ID NO: 3, or a conservative substitution variant thereof that promotes transmembrane delivery,
   wherein the panel of at least two fusion polypeptides comprises at least two different TB-specific antigen polypeptides,
   wherein one of the TB-specific antigen polypeptide is TB1 (CFP) polypeptide of SEQ ID NO: 7 and wherein one of the TB-specific antigen polypeptide is TB2 (ESAT) polypeptide of SEQ ID NO: 6; and
   b. antibody-based detection means to detect INF-γ released from the biological sample.

2. The kit of claim 1, wherein said portion of a LF polypeptide is a N-terminal lethal factor (LFn) polypeptide of at least the 104 carboxy-terminal amino acids of SEQ ID NO: 3, or a conservative substitution variant thereof that promotes transmembrane delivery.

3. The kit of claim 1, wherein the portion of a LF polypeptide is a N-terminal lethal factor (LFn) polypeptide of the amino acid sequence corresponding to SEQ ID NO: 3 or a conservative substitution variant thereof that promotes transmembrane delivery.

4. A kit for measuring a cell mediated immune (CMI) response to a TB antigen polypeptide of a biological sample from a subject, the kit comprising:
   a. a panel of at least two fusion polypeptides wherein each fusion polypeptide comprises a portion of a LF polypeptide lacking LF enzymatic activity but sufficient to promote transmembrane delivery of said fusion polypeptide to a cell, fused to a TB-specific antigen polypeptide,
   wherein said portion of a LF polypeptide comprises at least the 60 carboxy-terminal amino acids of SEQ ID NO: 3,
   wherein the panel of at least two fusion polypeptides comprises at least two different TB-specific antigen polypeptides,
   wherein the at least two different TB-specific antigen polypeptides are selected from the group consisting of: SEQ ID NO: 8 to SEQ ID NO: 29; and
   b. antibody-based detection means to detect INF-Y released from the biological sample.

5. A kit for measuring a cell mediated immune (CMI) response to a TB antigen polypeptide of a biological sample from a subject, the kit comprising:
   a. a panel of at least two fusion polypeptides wherein each fusion polypeptide comprises a portion of a LF polypeptide lacking LF enzymatic activity but sufficient to promote transmembrane delivery of said fusion polypeptide to a cell, fused to a TB-specific antigen polypeptide,
wherein said portion of a LF polypeptide comprises at least the 60 carboxy-terminal amino acids of SEQ ID NO: 3,
wherein the panel of at least two fusion polypeptides comprises at least two different TB-specific antigen polypeptides,
wherein the at least two different TB-specific antigen polypeptides are selected from the group consisting of: SEQ ID NO: 30 to SEQ ID NO: 46; and
b. antibody-based detection means to detect INF-Y released from the biological sample.

6. The kit of claim 4, wherein said portion of a LFn polypeptide comprises at least the 104 carboxy-terminal amino acids of SEQ ID NO: 3, or a conservative substitution variant thereof that promotes transmembrane delivery.

7. The kit of claim 4, wherein the portion of a LFn polypeptide comprises the amino acid sequence corresponding to SEQ ID NO: 3, or a conservative substitution variant thereof that promotes transmembrane delivery.

8. The kit of claim 4, wherein the panel of fusion polypeptides comprises between 3-20 fusion polypeptides.

9. The kit of claim 5, wherein said portion of a LFn polypeptide comprises at least the 104 carboxy-terminal amino acids of SEQ ID NO: 3, or a conservative substitution variant thereof that promotes transmembrane delivery.

10. The kit of claim 5, wherein the portion of a LFn polypeptide comprises the amino acid sequence corresponding to SEQ ID NO: 3, or a conservative substitution variant thereof that promotes transmembrane delivery.

11. The kit of claim 5, wherein the panel of fusion polypeptides comprises between 3-20 fusion polypeptides.

* * * * *